US010100335B2

(12) United States Patent
Prather et al.

(10) Patent No.: US 10,100,335 B2
(45) Date of Patent: Oct. 16, 2018

(54) MICROBIAL PRODUCTION OF BRANCHED MEDIUM CHAIN ALCOHOLS, SUCH AS 4-METHYLPENTANOL

(71) Applicant: Massachusetts Institute of Technology, Cambridge, MA (US)

(72) Inventors: Kristala Lanett Jones Prather, Milton, MA (US); Micah James Sheppard, Arlington, MA (US); Aditya Kunjapur, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 2 days.

(21) Appl. No.: 14/530,540

(22) Filed: Oct. 31, 2014

(65) Prior Publication Data
US 2015/0132816 A1    May 14, 2015

Related U.S. Application Data

(60) Provisional application No. 61/899,129, filed on Nov. 1, 2013.

(51) Int. Cl.
| | | |
|---|---|---|
| C12P 7/02 | (2006.01) | |
| C12N 15/00 | (2006.01) | |
| C12N 1/20 | (2006.01) | |
| C12N 9/02 | (2006.01) | |
| C12N 9/88 | (2006.01) | |
| C12N 9/10 | (2006.01) | |
| C07H 21/04 | (2006.01) | |
| C12P 7/04 | (2006.01) | |
| C12N 15/09 | (2006.01) | |
| C12N 9/04 | (2006.01) | |
| C12N 9/24 | (2006.01) | |

(52) U.S. Cl.
CPC ............... *C12P 7/04* (2013.01); *C12N 9/001* (2013.01); *C12N 9/0006* (2013.01); *C12N 9/0008* (2013.01); *C12N 9/2402* (2013.01); *C12N 9/88* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 7,399,323 | B2 | 7/2008 | Renninger et al. |
| 8,361,760 | B2 | 1/2013 | Martin et al. |
| 8,669,379 | B2 | 3/2014 | Dhamankar et al. |
| 2008/0249336 | A1 | 10/2008 | Singleton et al. |
| 2013/0183728 | A1 | 7/2013 | Botes et al. |
| 2014/0364629 | A1 | 12/2014 | Dhamankar et al. |

OTHER PUBLICATIONS

Peplinski et al., Investigations on the microbial catabolism of the organic sulfur compounds TDP and DTDP in Ralstonia eutropha H16 employing DNA microarrays. Appl Microbiol Biotechnol. Nov. 2010;88(5):1145-59. doi: 10.1007/s00253-010-2915-6. Epub Oct. 6, 2010.

(Continued)

*Primary Examiner* — Yong D Pak
(74) *Attorney, Agent, or Firm* — Wolf, Greenfield & Sacks, P.C.

(57) ABSTRACT

The invention relates to recombinant cells and their use in in the production of branched medium-chain alcohols such as 4-methyl-1-pentanol.

21 Claims, 26 Drawing Sheets

Specification includes a Sequence Listing.

(56) References Cited

OTHER PUBLICATIONS

Akhtar et al., Carboxylic acid reductase is a versatile enzyme for the conversion of fatty acids into fuels and chemical commodities. Proc Natl Acad Sci U S A. Jan. 2, 2013;110(1):87-92. doi: 10.1073/pnas.1216516110.
Atsumi et al., Acetolactate synthase from Bacillus subtilis serves as a 2-ketoisovalerate decarboxylase for isobutanol biosynthesis in Escherichia coli. Appl Environ Microbiol. Oct. 2009;75(19):6306-11. doi: 10.1128/AEM.01160-09.
Atsumi et al., Engineering the isobutanol biosynthetic pathway in Escherichia coli by comparison of three aldehyde reductase/alcohol dehydrogenase genes. Appl Microbiol Biotechnol. Jan. 2010;85(3):651-7. doi: 10.1007/s00253-009-2085-6.
Atsumi et al., Metabolic engineering for advanced biofuels production from Escherichia coli. Gun Opin Biotechnol. Oct. 2008;19(5):414-9. doi:10.1016/j.copbio.2008.08.008.
Atsumi et al., Metabolic engineering of Escherichia coli for 1-butanol production. Metab Eng. Nov. 2008;10(6):305-11.
Atsumi et al., Non-fermentative pathways for synthesis of branched-chain higher alcohols as biofuels. Nature. Jan. 3, 2008;451(7174):86-9. doi: 10.1038/nature06450.
Bachmann, Biosynthesis: is it time to go retro? Nat Chem Biol. Jun. 2010;6(6):390-3. doi: 10.1038/nchembio.377.
Bond-Watts et al., Enzyme mechanism as a kinetic control element for designing synthetic biofuel pathways. Nat Chem Biol. Apr. 2011;7(4):222-7. doi: 10.1038/nchembio.537.
Chan et al., Current understanding of fatty acid biosynthesis and the acyl carrier protein. Biochem J. Aug. 15, 2010;430(1):1-19. doi:10.1042/BJ20100462. Review. Erratum in: Biochem J. Aug. 27, 2010;430(3):559.
Chao et al., Heats of Combustion, Formation, and Isomerization of Nineteen Alkanols. J. Chem. Eng. Data. 1965;10(4):374-379.
Choi et al., Cloning of the Alcaligenes latus polyhydroxyalkanoate biosynthesis genes and use of these genes for enhanced production of Poly(3-hydroxybutyrate) in Escherichia coli. Appl Environ Microbiol. Dec. 1998;64(12):4897-903.
Cracan et al., IcmF is a fusion between the radical B12 enzyme isobutyryl-CoA mutase and its G-protein chaperone. J Biol Chem. Jan. 1, 2010;285(1):655-66. doi: 10.1074/jbc.M109.062182.
Crosby et al., System-wide studies of N-lysine acetylation in Rhodopseudomonas palustris reveal substrate specificity of protein acetyltransferases. J Biol Chem. May 4, 2012;287(19):15590-601. doi: 10.1074/jbc.M112.352104.
Dahiyat et al., De novo protein design: fully automated sequence selection. Science. Oct. 3, 1997;278(5335):82-7.
De Smidt et al., the alcohol dehydrogenases of Saccharomyces cerevisiae: a comprehensive review. FEMS Yeast Res. Nov. 2008;8(7):967-78. doi: 10.1111/j.1567-1364.2008.00387.x.
Dehesh et al., Production of high levels of 8:0 and 10:0 fatty acids in transgenic canola by overexpression of Ch FatB2, a thioesterase cDNA from Cuphea hookeriana. Plant J. Feb. 1996;9(2):167-72.
Dekishima et al., Extending carbon chain length of 1-butanol pathway for 1-hexanol synthesis from glucose by engineered Escherichia coli. J Am Chem Soc. Aug. 3, 2011;133(30):11399-401. doi:10.1021/ja203814d.
Dellomonaco et al., Engineered reversal of the β-oxidation cycle for the synthesis of fuels and chemicals. Nature. Aug. 10, 2011;476(7360):355-9. doi: 10.1038/nature10333.
Dennis et al., Formation of poly(3-hydroxybutyrate-co-3-hydroxyhexanoate) by PHA synthase from Ralstonia eutropha. J Biotechnol. Oct. 8, 1998;64(2-3):177-86.
Dickson, Thematic review series: sphingolipids. New insights into sphingolipid metabolism and function in budding yeast. J Lipid Res. May 2008;49(5):909-21. doi: 10.1194/jlr.R800003-JLR200.
Dugar et al., Relative potential of biosynthetic pathways for biofuels and bio-based products. Biotechnol. Dec. 8, 2011;29(12):1074-8. doi:10.1038/nbt.2055.

Ferrandez et al., Molecular characterization of PadA, a phenylacetaldehyde dehydrogenase from Escherichia coli. FEBS Lett. Apr. 7, 1997;406(1-2):23-7.
Fontaine et al., Molecular characterization and transcriptional analysis of adhE2, the gene encoding the NADH-dependent aldehyde/alcohol dehydrogenase responsible for butanol production in alcohologenic cultures of Clostridium acetobutylicum ATCC 824. J Bacteriol. Feb. 2002;184(3):821-30.
Goenaga et al., Effect of Temperature on Thermophysical Properties of Ethanol + Aliphatic Alcohols (C4-C5) Mixtures. Monatsh. Chem. 2007;138: 403-436. doi:10.1007/s00706-007-0623-4.
Hales et al., Liquid densities from 293 to 490 K of nine aliphatic alcohols. J Chem Thermo. Dec. 1976;8(12):1177-1184.
Handke et al., Application and engineering of fatty acid biosynthesis in Escherichia coli for advanced fuels and chemicals. Metab Eng. Jan. 2011;13(1):28-37. doi: 10.1016/j.ymben.2010.10.007.
Hansen et al., De novo biosynthesis of vanillin in fission yeast (Schizosaccharomyces pombe) and baker's yeast (Saccharomyces cerevisiae). Appl Environ Microbiol. May 2009;75(9):2765-74. doi: 10.1128/AEM.02681-08.
Hoffmeister et al., Mitochondrial trans-2-enoyl-CoA reductase of wax ester fermentation from Euglena gracilis defines a new family of enzymes involved in lipid synthesis. J Biol Chem. Feb. 11, 2005;280(6):4329-38.
Hopwood et al., Molecular Genetics of Polyketides and its Comparison to Fatty Acid Biosynthesis. Annu. Rev. Genet. 1990;24:37-66.
Howard et al., Synthesis of customized petroleum-replica fuel molecules by targeted modification of free fatty acid pools in Escherichia coli. Proc Natl Acad Sci U S A. May 7, 2013;110(19):7636-41. doi:10.1073/pnas.1215966110.
Huang et al., Analysis of biofuels production from sugar based on three criteria: Thermodynamics, bioenergetics, and product separation. Energy Environ. Sci. 2011;4:784-792. doi:10.1039/C0EE00069H.
Hussein et al., Densities and Kinematic Viscosities of Ten Binary 1-Alkanol Liquid Systems at Temperatures of (293.15 and 298.15) K. J. Chem. Eng. Data. 2009;54(10):2948-2952.
Inoue et al., Gene cloning and expression of Leifsonia alcohol dehydrogenase (LSADH) involved in asymmetric hydrogen-transfer bioreduction to produce (R)-form chiral alcohols. Biosci Biotechnol Biochem. Feb. 2006;70(2):418-26.
Inoue et al., Purification and characterization of a novel alcohol dehydrogenase from Leifsonia sp. strain 5749: a promising biocatalyst for an asymmetric hydrogen transfer bioreduction. Appl Environ Microbiol. Jul. 2005;71(7):3633-41.
Jo et al., Cloning, expression, and characterization of an aldehyde dehydrogenase from Escherichia coli K-12 that utilizes 3-Hydroxypropionaldehyde as a substrate. Appl Microbiol Biotechnol. Nov. 2008;81(1):51-60. doi: 10.1007/s00253-008-1608-x.
Jörnvall et al., Characteristics of alcohol/polyol dehydrogenases. The zinc-containing long-chain alcohol dehydrogenases. Eur J Biochem. Sep. 1, 1987;167(2):195-201.
Kawashima et al., Characterization and functional analyses of R-specific enoyl coenzyme A hydratases in polyhydroxyalkanoate-producing Ralstonia eutropha. Appl Environ Microbiol. Jan. 2012;78(2):493-502. doi: 10.1128/AEM.06937-11.
Kim et al., Dihydrolipoamide dehydrogenase mutation alters the NADH sensitivity of pyruvate dehydrogenase complex of Escherichia coli K-12. J Bacteriol. Jun. 2008;190(11):3851-8. doi: 10.1128/JB.00104-08.
Kurihara et al., A novel putrescine utilization pathway involves gamma-glutamylated intermediates of Escherichia coli K-12. J Biol Chem. Feb. 11, 2005;280(6):4602-8.
Larroy et al., Characterization of the Saccharomyces cerevisiae YMR318C (ADH6) gene product as a broad specificity NADPH-dependent alcohol dehydrogenase: relevance in aldehyde reduction. Biochem J. Jan. 1, 2002;361(Pt 1):163-72.
Lee et al., Metabolic engineering of microorganisms for biofuels production: from bugs to synthetic biology to fuels. Curr Opin Biotechnol. Dec. 2008;19(6):556-63. doi:10.1016/j.copbio.2008.10.014.

(56) References Cited

OTHER PUBLICATIONS

Lennen et al., Microbial production of fatty acid-derived fuels and chemicals. Curr Opin Biotechnol. Dec. 2013;24(6):1044-53. doi:10.1016/j.copbio.2013.02.028.
Li et al., Purification, characterization, and properties of an aryl aldehyde oxidoreductase from *Nocardia* sp. strain NRRL 5646. J Bacteriol. Jun. 1997;179(11):3482-7.
Lichtenthaler et al., Two independent biochemical pathways for isopentenyl diphosphate and isoprenoid biosynthesis in higher plants. Physiologia Plantarum. 1997;101:643-652. doi:10.1111/j.1399-3054.1997.tb01049.x.
Lim et al., Fundamental relationship between operon organization and gene expression. Proc Natl Acad Sci U S A. Jun. 28, 2011;108(26):10626-31. doi:10.1073/pnas.1105692108.
Machado et al., Cyanobacterial biofuel production. J Biotechnol. Nov. 30, 2012;162(1):50-6. doi: 10.1016/j.jbiotec.2012.03.005.
Magnuson et al., Regulation of fatty acid biosynthesis in *Escherichia coli*. Microbiol Rev. Sep. 1993;57(3):522-42.
Marcheschi et al., A synthetic recursive "+1" pathway for carbon chain elongation. ACS Chemical Biology. 2012;7(4): 689-697. DOI: 10.1021/cb200313e.
Martin et al., A platform pathway for production of 3-hydroxyacids provides a biosynthetic route to 3-hydroxy-γ-butyrolactone. Nat Commun. 2013;4:1414. doi: 10.1038/ncomms2418. Erratum in: Nat Commun. 2013;4:1933.
McMahon et al., Functional screening and in vitro analysis reveal thioesterases with enhanced substrate specificity profiles that improve short-chain fatty acid production in *Escherichia coli*. Appl Environ Microbiol. Feb. 2014;80(3):1042-50. doi: 10.1128/AEM.03303-13.
Moon et al., Production of glucaric acid from a synthetic pathway in recombinant *Escherichia coli*. Appl Environ Microbiol. Feb. 2009;75(3):589-95. doi: 10.1128/AEM.00973-08. Erratum in: Appl Environ Microbiol. Jul. 2009;75(13):4660.
Nielsen et al., Engineering alternative butanol production platforms in heterologous bacteria. Metab Eng. Jul.-Sep. 2009;11(4-5):262-73. doi: 10.1016/j.ymben.2009.05.003.
Niu et al., Microbial synthesis of the energetic material precursor 1,2,4-butanetriol. J Am Chem Soc. Oct. 29, 2003;125(43):12998-9.
Pfeifer et al., Biosynthesis of complex polyketides in a metabolically engineered strain of *E. coli*. Science. Mar. 2, 2001;291(5509):1790-2.
Prather et al., De novo biosynthetic pathways: rational design of microbial chemical factories. Curr Opin Biotechnol. Oct. 2008;19(5):468-74. doi:10.1016/j.copbio.2008.07.009.
Ragauskas et al., The path forward for biofuels and biomaterials. Science. Jan. 27, 2006;311(5760):484-9.
Rodríguez-Zavala et al., Characterization of *E. coli* tetrameric aldehyde dehydrogenases with atypical properties compared to other aldehyde dehydrogenases. Protein Sci. Jun. 2006;15(6):1387-96.
Shen et al., Driving forces enable high-titer anaerobic 1-butanol synthesis in *Escherichia coli*. Appl Environ Microbiol. May 2011;77(9):2905-15. doi: 10.1128/AEM.03034-10.
Steen et al., Metabolic engineering of *Saccharomyces cerevisiae* for the production of n-butanol. Microb Cell Fact. Dec. 3, 2008;7:36. doi: 10.1186/1475-2859-7-36.
Taguchi et al., A microbial factory for lactate-based polyesters using a lactate-polymerizing enzyme. Proc Nati Acad Sci U S A. Nov. 11, 2008;105(45):17323-7. doi: 10.1073/pnas.0805653105.
Torella et al., Tailored fatty acid synthesis via dynamic control of fatty acid elongation. Proc Natl Acad Sci U S A. Jul. 9, 2013;110(28):11290-5. doi: 10.1073/pnas.1307129110.
Tseng et al., Biosynthesis of chiral 3-hydroxyvalerate from single propionate-unrelated carbon sources in metabolically engineered *E. coli*. Microb Cell Fact. Nov. 27, 2010;9:96. doi: 10.1186/1475-2859-9-96.
Tseng et al., Controlled biosynthesis of odd-chain fuels and chemicals via engineered modular metabolic pathways. Proc Natl Acad Sci U S A. Oct. 30, 2012;109(44):17925-30. doi: 10.1073/pnas.1209002109.
Tseng et al., Metabolic engineering of *Escherichia coli* for enhanced production of (R)- and (S)-3-hydroxybutyrate. Appl Environ Microbiol. May 2009;75(10):3137-45. doi:10.1128/AEM.02667-08.
Tucci et al., A novel prokaryotic trans-2-enoyl-CoA reductase from the spirochete Treponema denticola. FEBS Lett. Apr. 17, 2007;581(8):1561-6.
Venkitasubramanian et al., Reduction of carboxylic acids by Nocardia aldehyde oxidoreductase requires a phosphopantetheinylated enzyme. J Biol Chem. Jan. 5, 2007;282(1):478-85.
Voelker et al., Alteration of the specificity and regulation of fatty acid synthesis of *Escherichia coli* by expression of a plant medium-chain acyl-acyl carrier protein thioesterase. J Bacteriol. Dec. 1994;176(23):7320-7.
Wallner et al., Analytical Assessment of C2-C8 Alcohols as Spark-Ignition Engine Fuels. Proceedings FISITA 2012 World Automotive Congress. 3;15-26.
Wang et al., Aqueous solubility prediction based on weighted atom type counts and solvent accessible surface areas. J Chem Inf Model. Mar. 2009;49(3):571-81. doi: 10.1021/ci800406y.
Wenzel et al., Recent developments towards the heterologous expression of complex bacterial natural product biosynthetic pathways. Curr Opin Biotechnol. Dec. 2005;16(6):594-606.
White et al., The structural biology of type II fatty acid biosynthesis. Annu Rev Biochem. 2005;74:791-831.
Withers et al., Identification of isopentenol biosynthetic genes from Bacillus subtilis by a screening method based on isoprenoid precursor toxicity. Appl Environ Microbiol. Oct. 2007;73(19):6277-83.
Yamanaka et al., Thermostable aldehyde dehydrogenase from psychrophile, *Cytophaga* sp. KUC-1: enzymological characteristics and functional properties. Biochem Biophys Res Commun. Nov. 15, 2002;298(5):632-7.
Youngquist et al., Free fatty acid production in *Escherichia coli* under phosphate-limited conditions. Appl Microbiol Biotechnol. Jun. 2013;97(11):5149-59. doi: 10.1007/s00253-013-4911-0.
Zhang et al., A synthetic metabolic pathway for production of the platform chemical isobutyric acid. ChemSusChem. Aug. 22, 2011;4(8):1068-70. doi: 10.1002/cssc.201100045.
Zhang et al., Efficient free fatty acid production in *Escherichia coli* using plant acyl-ACP thioesterases. Metab Eng. Nov. 2011;13(6):713-22. doi: 10.1016/j.ymben.2011.09.007.
Zhang et al., Expanding metabolism for biosynthesis of nonnatural alcohols. Proc Natl Acad Sci U S A. Dec. 30, 2008;105(52):20653-8. doi: 10.1073/pnas.0807157106.
Zor et al., Linearization of the Bradford protein assay increases its sensitivity: theoretical and experimental studies. Anal Biochem. May 1, 1996;236(2):302-8.
Sheppard et al., Retro-biosynthetic screening of a modular pathway design achieves selective route for microbial synthesis of 4-methylpentanol. Nat Commun. Sep. 24, 2014;5:5031. doi: 10.1038/ncomms6031.

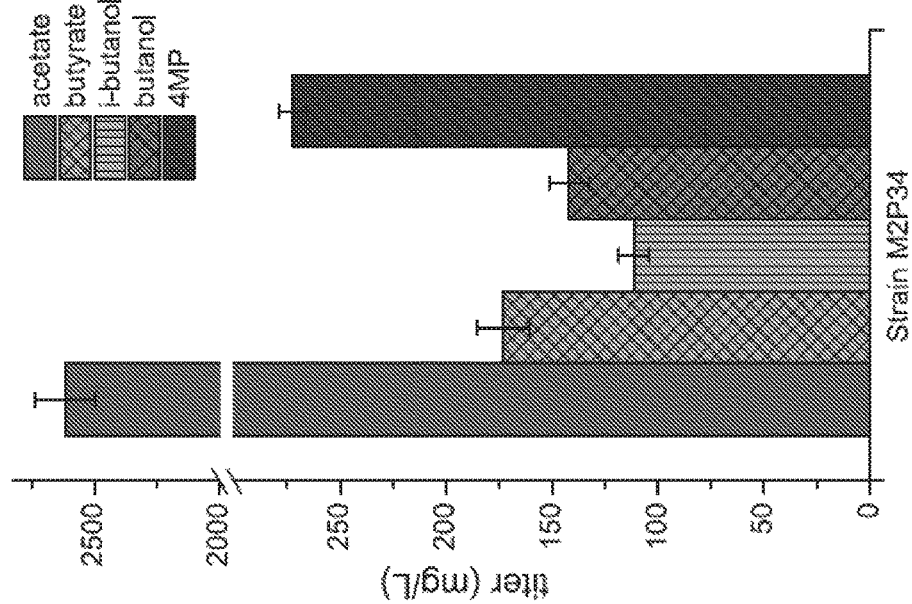
FIG. 2C
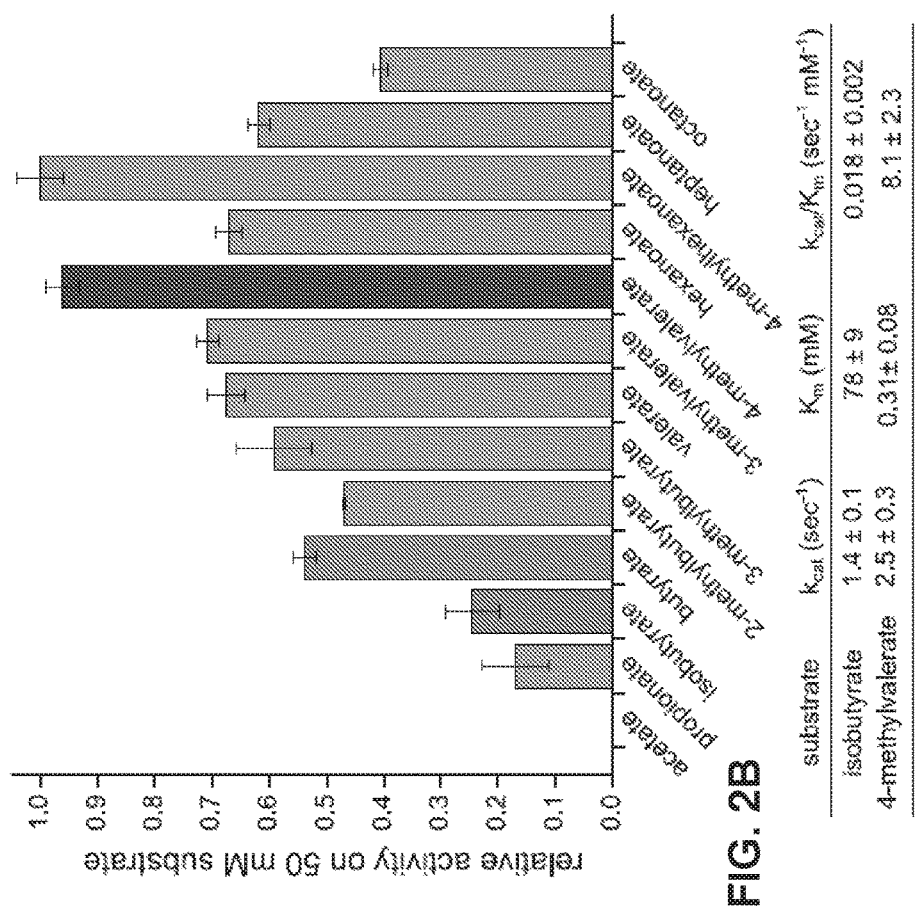
FIG. 2A
FIG. 2B

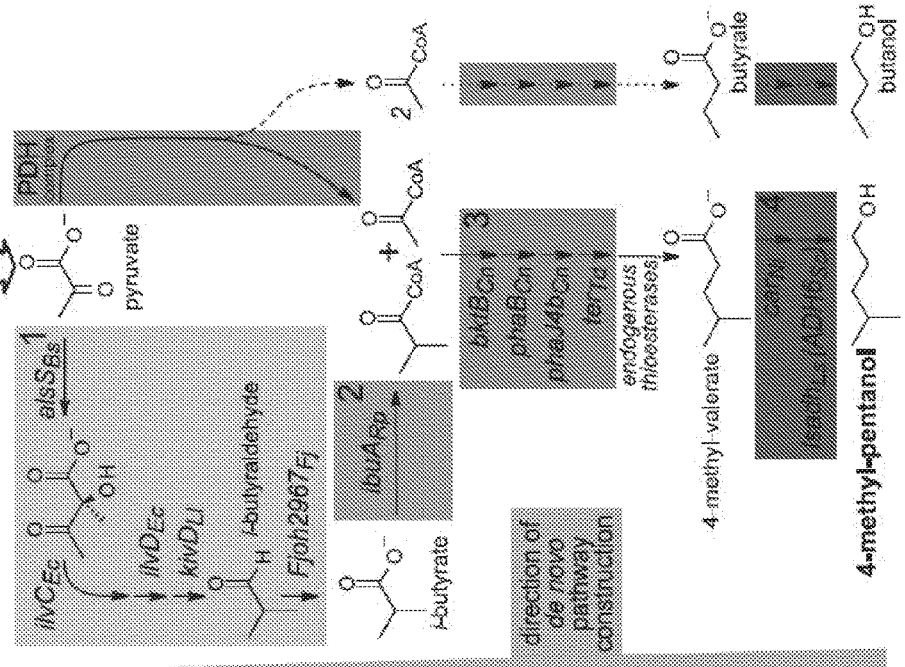
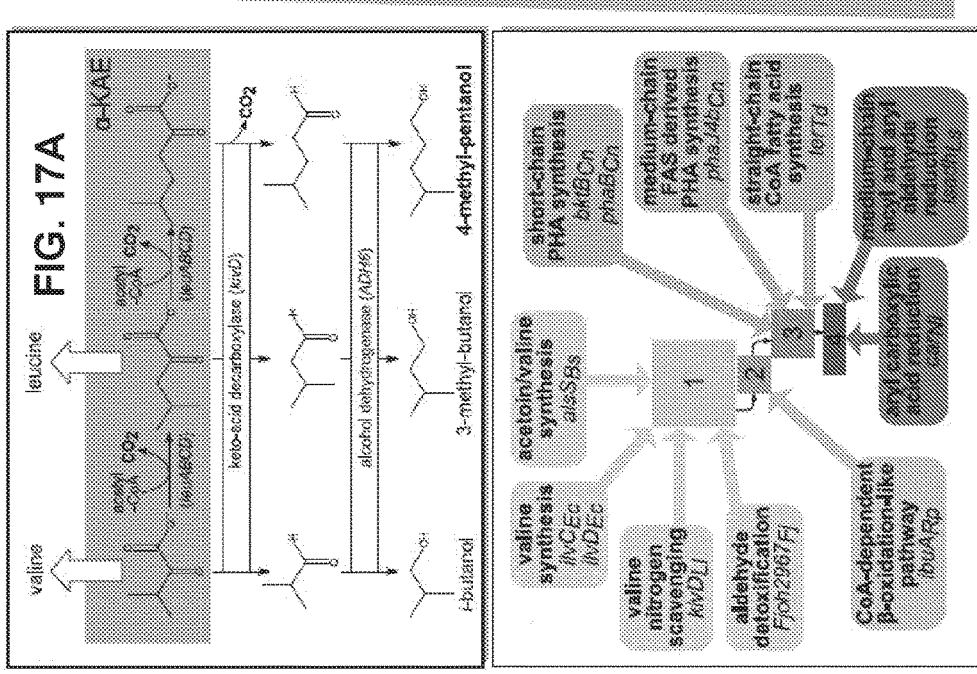

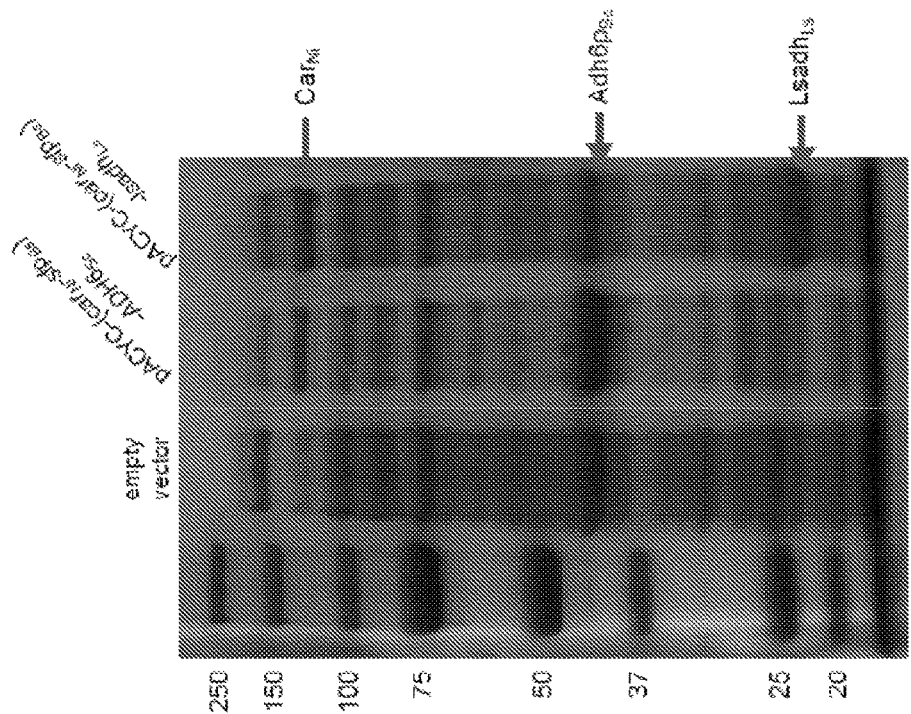
FIG. 26A
FIG. 26B
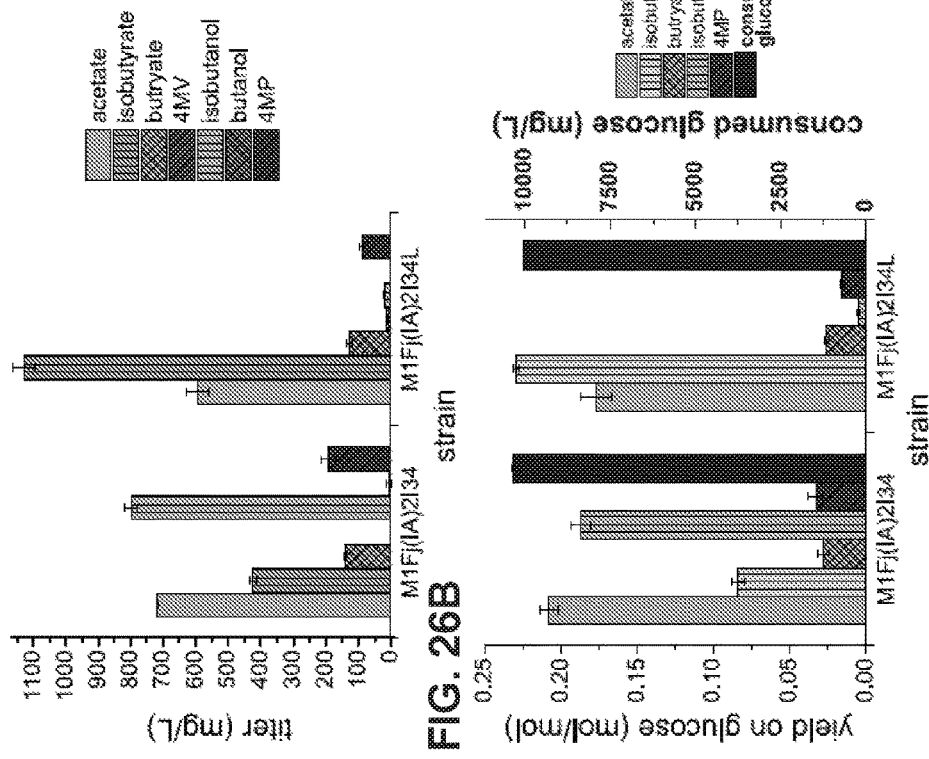
FIG. 26C

```
SEQUENCE LISTING

<160> NUMBER OF SEQ ID NOS: 68

<210> SEQ ID NO 1
<211> LENGTH: 1080
<212> TYPE: DNA
<213> ORGANISM: artificial sequence
<220> FEATURE:
<223> OTHER INFORMATION: synthetic polynucleotide

<400> SEQUENCE: 1
atgagctacc cggaaaagtt cgagggtatt gctattcagt cccatgagga ctggaagaac      60
ccgaagaaaa ccaagtatga tccgaagccg ttctacgacc acgacatcga catcaaaatc     120
gaagcgtgcg gcgtgtgcgg tagcgatatc cactgcgcag cgggccactg gggtaacatg     180
aaaatgccac tggtggtggg ccatgagatt gtcggtaagg tggtgaaact gggcccgaag     240
agcaacagcg gcctgaaagt tggtcagcgt gtgggtgttg gtgcgcaagt ctttagctgt     300
ttggaatgtg atcgctgtaa aacgataat gaaccgtatt gcacgaagtt tgttaccacc     360
tattcgcaac cttatgagga tggttacgtc agccaaggcg gttatgcaaa ctatgtgcgc     420
gttcacgagc acttcgttgt gccgattccg gagaatatcc cgagccatct ggcagcaccg     480
ctgctgtgtg gcggtctgac ggtctactcc cgctggtcc gcaatggttg cggtccgggc     540
aagaaagtgg gcattgttgg tctgggtggc atcggttcta tgggcacgtt gatttcgaag     600
gccatgggtg cggagactta cgtcatctct cgttctagcc gcaaacgtga ggacgcgatg     660
aagatgggtg ccgatcacta cattgcgacc ctggaagagg gtgactgggg cgagaaatac     720
tttgacacct tcgatctgat tgttgtgtgc gcgagcagcc tgacggatat tgactttaac     780
attatgccaa aagccatgaa agtcggtggc cgcatcgttt ccattagcat ccctgaacag     840
cacgagatgc tgagcctgaa gccgtacggt ctgaaggcag ttagcattag ctacagcgct     900
ctgggctcca tcaaagaact gaatcagctg ctgaaattgg tgagcgaaaa agacatcaag     960
atctgggttg aaaccctgcc ggtgggtgag gcaggtgtcc acgaggcctt tgagcgtatg    1020
gaaaaaggcg atgtgcgtta tcgtttcacc ctggttggtt acgataaaga attcagcgac    1080

<210> SEQ ID NO 2
<211> LENGTH: 3525
<212> TYPE: DNA
<213> ORGANISM: artificial sequence
<220> FEATURE:
<223> OTHER INFORMATION: synthetic polynucleotide

<400> SEQUENCE: 2
atggctgtgg actcgccgga tgaacgcctg caacgccgta tcgcccaact gtttgccgaa      60
gatgaacaag tgaaagctgc ccgcccgctg gaagcagtta gcgcggccgt ctctgcaccg     120
ggtatgcgtc tggctcagat cgcagctacg gtgatggctg gttatgcgga tcgtccggcg     180
gcgggccagc gtgctttcga actgaatacc gatgacgcaa ccggccgtac cagcctgcgt     240
ctgctgccgc gttttgaaac cattacgtac cgcgaactgt ggcagcgtgt cggcgaagtg     300
gcagctgcgt ggcatcacga cccggaaaac ccgctgcgtg cgggtgattt tgtggccctg     360
```

```
ctgggcttca ccagcattga ttatgcaacg ctggatctgg ctgacatcca tctgggtgcg    420
gttaccgtgc cgctgcaagc gagcgcggcg gtgtcccaac tgattgcaat cctgaccgaa    480
acgagtccgc gcctgctggc gtccaccccg gaacatctgg atgctgcggt ggaatgcctg    540
ctggcaggca ccacgccgga acgtctggtg gttttcgatt atcacccgga agatgacgat    600
cagcgcgccg catttgaaag tgcgcgtcgc cgtctggcag atgcaggttc cctggtgatc    660
gttgaaaccc tggacgcggt gcgtgcgcgt ggccgtgatc tgccggctgc gccgctgttt    720
gtcccggata ccgacgatga cccgctggcg ctgctgattt atacgtcagg ttcgaccggc    780
acgccgaaag gtgccatgta caccaatcgt ctggccgcaa cgatgtggca gggcaactca    840
atgctgcaag gcaacagcca acgcgttggc attaacctga attatatgcc gatgagtcat    900
attgcgggtc gtatctccct gttcggcgtg ctggcgcgtg gcggcaccgc atactttgct    960
gcgaaatcag acatgagcac cctgtttgaa gatattggcc tggttcgccc gaccgaaatc   1020 ttttcgttc cgcgtgtctg tgacatggtg tttcagcgct atcaaagcga actggatcgc   1080
cgttctgtcg ctggtgcgga tctggacacc ctggaccgca agtgaaagc ggatctgcgt   1140 cagaattacc tgggcggtcg cttcctggtt gcagtcgtgg gctcggctcc gctggccgca   1200
gaaatgaaaa cgtttatgga aagcgtgctg gacctgccgc tgcatgatgg ttatggcagt   1260
accgaagccg gcgcatccgt tctgctggat aaccagatcc aacgtccgcc ggtcctggac   1320
tataaactgg tcgatgtgcc ggaactgggt tactttcgca cggatcgtcc gcacccgcgt   1380
ggcgaactgc tgctgaaagc agaaaccacg attccgggtt attacaaacg cccggaagtt   1440
acggcggaaa tctttgatga agacggcttc tataaaaccg cgatattgt ggccgaactg   1500 gaacatgacc gcctggttta cgtggatcgt cgtaacaatg ttctgaaact gtcccagggc   1560
gaatttgtga ccgttgcgca cctggaagct gtgttcgcga gcagcccgct gatccgtcaa   1620
atttttatct atggtagttc gaacgcagt tacctgctgg ccgtcattgt gccgaccgat   1680
gacgcactgc gtgccgcgga taccgctacg ctgaaaagcg ctctggcgga atctattcag   1740
cgtatcgcca aagacgcaaa tctgcaaccg tatgaaattc gcgcgatttt tctgatcgaa   1800
accgaaccgt tcacgattgc caatggcctg ctgagcggta tcgcaaaact gctgcgcccg   1860
aacctgaaag aacgttatgg tgcgcagctg gaacaaatgt acaccgacct ggctacgggc   1920
caggcagatg aactgctggc cctgcgccgt gaagctgcgg atctgccggt gctgaaaacc   1980
gttagccgtg ccgcaaaagc gatgctgggt gtggcaagcg cggatatgcg tccggacgca   2040
cattttaccg atctgggcgg tgacagcctg tctgcactga gttttccaa cctgctgcac   2100 gaaatcttcg gtgttgaagt cccggtgggt gttgtcgtgt ctccggcaaa cgaactgcgt   2160
gatctggcga attatattga agccgaacgc aacagtggcg caaaacgtcc gaccttcacg   2220
tcagtgcatg gcggtggctc ggaaattcgt gctgcggatc tgaccctgga caaatttatc   2280
gatgcacgca cgctggccgc agctgattct attccgcacg cccggtgcc ggcacagacc   2340 gttctgctga cgggtgcgaa tggctatctg ggtcgttttcc tgtgcctgga atggctggaa   2400
cgcctggata aaaccggcgg cacccctgatt tgtgttgtcc gtggtagcga cgcggcggcg   2460
gcacgtaaac gtctggattc agcctttgat agcggcgatc cgggcctgct ggaacattat   2520
cagcaactgg cagcacgtac cctggaagtg ctggcaggcg atattggtga cccgaacctg   2580
ggcctggatg acgcgacctg gcagcgtctg cagaaacgg tcgatctgat tgtgcatccg   2640
gcagctctgg tgaatcacgt tctgccgtac acccagctgt ttggcccgaa cgtggttggc   2700
accgcggaaa ttgtgcgcct ggctatcacc gcgcgtcgta aaccagtgac ctatctgtct   2760
```

| | | |
|---|---|---|
| acggttggcg tcgcagatca ggttgacccg gctgaatacc aagaagatag cgatgtgcgt | 2820 | |
| gaaatgtctg cggtgcgtgt cgtgcgcgaa agctatgcca acggttacgg caattctaaa | 2880 | |
| tgggctggtg aagtgctgct gcgcgaagcg catgatctgt gcggtctgcc ggtggcagtt | 2940 | |
| tttcgttcag atatgattct ggcacactcg cgctatgctg gtcagctgaa tgtccaagat | 3000 | |
| gtgttcaccc gtctgattct gtcactggtt gctacgggca tcgcgccgta ttcgttttac | 3060 | |
| cgcaccgatg cagacggtaa ccgtcagcgc gcccattacg atggtctgcc ggcagatttc | 3120 | |
| accgcggcgg cgattacggc gctgggtatc caggccaccg aaggctttcg cacgtatgat | 3180 | |
| gtgctgaatc cgtatgatga cggtattagt ctggacgaat tgttgattg gctggtcgaa | 3240 | |
| tccggccatc cgattcagcg tatcacggat tattcagact ggtttcaccg cttcgaaacc | 3300 | |
| gccatccgtg cactgccgga aaaacagcgt caagccagcg tgctgccgct gctggatgca | 3360 | |
| taccgtaacc cgtgtccggc cgttcgcggt gcaattctgc cggctaaaga atttcaggct | 3420 | |
| gcggtccaaa ccgcgaaaat tggcccggaa caggatattc cgcacctgag tgccccgctg | 3480 | |
| attgataaat acgtgtctga cctggaactg ctgcaactgc tgtaa | 3525 | |

<210> SEQ ID NO 3
<211> LENGTH: 675
<212> TYPE: DNA
<213> ORGANISM: artificial sequence
<220> FEATURE:
<223> OTHER INFORMATION: synthetic polynucleotide

<400> SEQUENCE: 3

| | | |
|---|---|---|
| atgaaaatct atggcattta catggatcgt ccgctgagtc aggaagaaaa cgaacgcttt | 60 | |
| atgaccttca tcagcccgga aaaacgtgaa aaatgccgtc gctttatca taaagaagat | 120 | |
| gcacaccgca cgctgctggg cgatgtgctg gttcgtagcg tgatctctcg ccagtatcag | 180 | |
| ctggataaat ctgatattcg tttcagtacc caggaatacg gtaaaccgtg tattccggat | 240 | |
| ctgccggatg cacattttaa tatcagccac tctggccgct gggttattgg tgcgttcgat | 300 | |
| tctcagccga ttggtatcga tattgaaaaa cgaaaccga tcagtctgga aattgccaaa | 360 | |
| cgtttcttta gcaaaaccga atattctgat ctgctggcaa aagataaaga tgaacagacg | 420 | |
| gattactttt accatctgtg gagtatgaaa gaatcttta tcaaacagga aggcaaaggt | 480 | |
| ctgagcctgc cgctggatag ttttagcgtg cgcctgcatc aggatggcca ggtttctatc | 540 | |
| gaactgccgg attctcacag tccgtgctat attaaaacct acgaagttga tccgggctat | 600 | |
| aaaatggccg tttgtgcggc ccacccggat ttcccggaag atattacgat ggtgagctac | 660 | |
| gaagaactgc tgtaa | 675 | |

<210> SEQ ID NO 4
<211> LENGTH: 756
<212> TYPE: DNA
<213> ORGANISM: artificial sequence
<220> FEATURE:
<223> OTHER INFORMATION: synthetic polynucleotide

<400> SEQUENCE: 4

| | | |
|---|---|---|
| atggcccagt atgatgttgc agatcgtagc gcaattgtta ccggtggtgg tagcggtatt | 60 | |
| ggtcgtgcag ttgcactgac cctggcagca agcggtgcag cagttctggt taccgatctg | 120 | |
| aatgaagaac atgcacaggc agttgttgca gaaattgaag cagccggtgg taaagcagca | 180 | |
| gcactggctg gtgatgtgac cgatccggca tttggtgaag caagcgttgc cggtgcaaat | 240 | |

```
gcactggcac cgctgaaaat tgcagttaat aatgcaggta ttggtggtga agccgcaacc    300
gttggtgatt attcactgga tagctggcgt accgttattg aagttaatct gaatgccgtg    360
ttttatggta tgcagccgca gctgaaagca atggcagcaa atggtggtgg tgccattgtt    420
aatatggcaa gcattctggg tagcgttggt tttgcaaata gcagcgccta tgttaccgca    480
aaacatgcac tgctgggcct gacacagaat gcagccctgg aatatgcagc agataaagtt    540
cgtgttgttg ccgttggtcc gggttttatt cgtacaccgc tggttgaagc aaatctgagc    600
gcagatgccc tggcatttct ggaaggtaaa catgccctgg gtcgtctggg tgaaccggaa    660
gaagttgcaa gcctggttgc ctttctggca agtgatgcag caagctttat taccggtagc    720
tatcatctgg ttgatggtgg ttataccgca cagtaa                              756
```

```
<210> SEQ ID NO 5
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 5
atataggatc cgatgatcat caaacctaga attcg                               35

<210> SEQ ID NO 6
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 6
atatagcggc cgcttagatt tgaatgaagt ctgtttctac                           40

<210> SEQ ID NO 7
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 7
atataggatc cgatgattat caaacccaaa attcg                               35

<210> SEQ ID NO 8
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 8
atatagcggc cgcttaaagc tcaatcacat cgaactc                             37

<210> SEQ ID NO 9
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 9
atataggatc cgatcatcaa accgcgcgt                                      29
```

```
<210> SEQ ID NO 10
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 10
atatacttaa gttactggat caggttggcg at                                    32

<210> SEQ ID NO 11
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 11
atataggatc cgatggccat cattcatcct a                                     31

<210> SEQ ID NO 12
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 12
atatacttaa gttacagctc gacgcagtc                                        29

<210> SEQ ID NO 13
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 13
atataccatg gggatgaaga cctacgagaa catcg                                 35

<210> SEQ ID NO 14
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 14
atatagcggc cgccttatg                                                   19

<210> SEQ ID NO 15
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 15
atataccatg gggatgcctt ttgtacccgt cg                                    32

<210> SEQ ID NO 16
<211> LENGTH: 36
<212> TYPE: DNA
<213> ORGANISM: Artificial Sequence
<220> FEATURE:
<223> OTHER INFORMATION: Synthetic Polynucleotide
```

<400> SEQUENCE: 16
atatagcggc cgcttacacg aaacacaacg tcaaag          36

<210> SEQ ID NO 17
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 17 ataticcatg gggatgccat tcgtacccgt ag              32

<210> SEQ ID NO 18
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 18
atatagcggc cgctcagacg aagcagaggc t               31

<210> SEQ ID NO 19
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 19
aaaaaagatc tcatgacaaa agcaacaaaa ga              32

<210> SEQ ID NO 20
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 20
ggtgattcct cgtgctagag agctttcgtt ttcat           35

<210> SEQ ID NO 21
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 21
cacgaggaat cacc                                  14

<210> SEQ ID NO 22
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 22
catactttat ttactcccag ttaacccgca acag            34

<210> SEQ ID NO 23
<211> LENGTH: 20

```
<212> TYPE: DNA
<213> ORGANISM: Artificial Sequence
<220> FEATURE:
<223> OTHER INFORMATION: Synthetic Polynucleotide

<400> SEQUENCE: 23
ctgggagtaa ataaagtatg                                           20

<210> SEQ ID NO 24
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 24
aaaaagacgt cttaaccccc cagtt                                     25

<210> SEQ ID NO 25
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 25
aaaaaggatc cgatgacgcg tgaagtg                                   27

<210> SEQ ID NO 26
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 26
aaaaagcggc cgcttatttt ttcagtccca                                30

<210> SEQ ID NO 27
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 27
aaaaacatat ggggatgaag acc                                       23

<210> SEQ ID NO 28
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 28
aaaaacctag gtcagcccat gtgc                                      24

<210> SEQ ID NO 29
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 29
```

```
aaaaaggatc cgatgacgcg tgaagtg                                          27

<210> SEQ ID NO 30
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 30
caatcattat atctccttct ttcagatacg ctcgaag                               37

<210> SEQ ID NO 31
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 31
aagaaggaga tataatgatt gtgaaaccga tg                                    32

<210> SEQ ID NO 32
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 32 aaaagcggc cgctcaaata cggtcaaagc gttc                                   34

<210> SEQ ID NO 33
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 33
aaaaaggatc cgatgcctaa gtaccgttcc                                       30

<210> SEQ ID NO 34
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 34
caatcattat atctccttct tttaaccccc cagtttc                               37

<210> SEQ ID NO 35
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 35
aagaaggaga tataatgatt gtggaaaccg atg                                   33

<210> SEQ ID NO 36
<211> LENGTH: 34
<212> TYPE: DNA
<213> ORGANISM: Artificial Sequence
```

```
<220> FEATURE:
<223> OTHER INFORMATION: Synthetic Polynucleotide

<400> SEQUENCE: 36
aaaaagcggc cgctcaaata cggtcaaagc gttc                              34

<210> SEQ ID NO 37
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 37
tttttagatc tatggctaac tacttcaata c                                 31

<210> SEQ ID NO 38
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 38
caccctcact ccttattaac ccgcaacag                                    29

<210> SEQ ID NO 39
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 39
taaggagtga gggtgatgac aaaagcaaca aa                                32

<210> SEQ ID NO 40
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 40
tttttgacgt cctagagagc tttcgtttt                                    29

<210> SEQ ID NO 41
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 41
aaaaaggatc cgatgagaaa agtagaaatc attac                             35

<210> SEQ ID NO 42
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 42
catactttat ttcctcccag ttattttttc agtcccat                          38
```

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
ctgggaggaa ataaagtatg                                          20

<210> SEQ ID NO 44
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 44
aaaaagcggc cgcttaaccc cccagtt                                  27

<210> SEQ ID NO 45
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 45
aaaaaggatc cgatgagcaa cacccat                                  27

<210> SEQ ID NO 46
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 46
catactttat ttcctcccag tcaagctgca gaagaa                        36

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 47
ctgggaggaa ataaagtatg                                          20

<210> SEQ ID NO 48
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 48
aaaaagcggc cgcttaaccc cccagtt                                  27

<210> SEQ ID NO 49
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 49
tttttggatc cgatgtatac agtaggagat tacc                          34

<210> SEQ ID NO 50
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 50
tttttgcggc cgcttatgat ttattttgtt cag                           33

<210> SEQ ID NO 51
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 51
aaaaaagcgg ccgctaataa aaggagatat accatgaaaa tctatggcat ttacat   56

<210> SEQ ID NO 52
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 52
aaatttctta agttacagca gttcttcgta gct                           33

<210> SEQ ID NO 53
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 53
aaaaaagcgg ccgctaataa aaggagatat accatgaaaa tctatggcat ttacat   56

<210> SEQ ID NO 54
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 54
aaatttctta agttacagca gttcttcgta gct                           33

<210> SEQ ID NO 55
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 55
aaaaacccgg gaatatttgc tcatgagccc                               30

<210> SEQ ID NO 56

<210> SEQ ID NO 56
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 56
gctagcccaa aaaaacg                                                  17

<210> SEQ ID NO 57
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 57
gtttttttgg gctagcaata aggagtgagg gtgatg                              36

<210> SEQ ID NO 58
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 58
aaaaagcggc cgcctagaga gctttcgttt tcatg                               35

<210> SEQ ID NO 59
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 59
aaaaagcggc cgccgaagtt cctattctct agaaag                              36

<210> SEQ ID NO 60
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 60
aaaaacccgg gccttcaccg tttggac                                        27

<210> SEQ ID NO 61
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 61
ctcgtatgtt gtgtggaatt gtgagcggat aacaatttca cacaggaaac agcttacggc    60
cccaaggtcc                                                          70

<210> SEQ ID NO 62
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 62
gcttatcccg gtcgtttatt tcgcgaataa cccgacaagg aacgccagcc ttggcttcag    60
ggatgagg    68

<210> SEQ ID NO 63
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 63
ggttagcctt gcgctcgaga ggggagaatt c    31

<210> SEQ ID NO 64
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 64
taagtataag aaggagatat acat    24

<210> SEQ ID NO 65
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 65
aaaagaagga gatata    16

<210> SEQ ID NO 66
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 66
aagaaggaga tata    14

<210> SEQ ID NO 67
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 67
taaggagtga gggtg    15

<210> SEQ ID NO 68
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 68
ctgggagtaa ataaagt    17

US 10,100,335 B2

MICROBIAL PRODUCTION OF BRANCHED MEDIUM CHAIN ALCOHOLS, SUCH AS 4-METHYLPENTANOL

CROSS REFERENCE TO RELATED APPLICATIONS

This application claims the benefit under 35 U.S.C. § 119(e) of U.S. provisional application no. 61/899,129, filed Nov. 1, 2013, which is incorporated by reference herein in its entirety.

FEDERALLY SPONSORED RESEARCH

This invention was made with government support under W911NF-09-D-0001 awarded by the Army Research Office. The government has certain rights in this invention.

FIELD OF THE INVENTION

The invention relates to the production of branched medium chain alcohols such as 4-methyl-1-pentanol through recombinant gene expression.

BACKGROUND OF INVENTION

Recent interest in microbial production of fuels was bolstered by synthesis of a variety of "next-generation" fuels with improved properties (Atsumi, 2008). Shen, et al. (2010) *Appl. Environ Microbiol*; Tseng, et al. (2012) *PNAS*; Bond-Watts, et al. (2011) *Nat. Chem. Biol.*; Withers, et al. (2007) *Appl. Environ. Microbiol.*). Most "next generation" fuel targets are either C5 or smaller alcohols or long chain fatty acids/methyl esters. While longer chain acids or isoprenoid derived fuels may serve as potential biodiesel or jet fuels, gasoline alternatives for spark ignition engines would preferably fall in the C6-C7 range. Such medium-chain length alcohols achieve energy density equal to that of petroleum derived gasoline with reduced costs of downstream separation. Branched alcohols have the additional property of improved octane rating (Huang, et al. (2011) *Energy and Environ. Sci.*; Dugar, et al. (2011) *Nat. Biotech.*).

SUMMARY OF INVENTION

Previously described pathways for the production of next generation fuels either cannot generate C6/C7 alcohols or are not well equipped to do so. Described herein is a novel method for production of branched medium-chain alcohol, such as 4-methyl-1-pentanol. 4-methyl-1-pentanol is miscible with many organic solvents and could potentially be used for a variety of chemical reactions or extractions. Additionally, 4-methyl-1-pentanol represents a viable liquid fuel replacement for gasoline with high energy density and branches which improve the octane rating of the fuel; hence, there is much value in large scale production of the compound.

Aspects of the invention relate to a cell that recombinantly expresses a gene encoding a thiolase, a gene encoding an acetoacetyl-CoenzymeA (CoA) reductase, a gene encoding an acyl dehydratase, a gene encoding an enoyl-CoA reductase, and a gene encoding a carboxylic acid reductase.

In some embodiments, the gene encoding a thiolase is a bktB gene, the gene encoding an acetoacetyl-CoenzymeA (CoA) reductase is a phaB gene, the gene encoding an acyl dehydratase is a phaJ4b gene, the gene encoding an enoyl-CoA reductase is a ter gene, and the gene encoding a carboxylic acid reductase a car gene. In some embodiments, the cell further recombinantly expresses one or both of a gene encoding an alcohol dehydrogenase and a gene encoding an aldo-keto reductase. In some embodiments, the gene encoding an alcohol dehydrogenase is an ADH6 gene and the gene encoding an aldo-keto reductase is a yeaE gene. In some embodiments, the alcohol dehydrogenase is an lsadh gene.

In some embodiments, the cell further recombinantly expresses one or more of a gene encoding an acetolactate synthase, a gene encoding an acetohydroxy acid isomeroreductase, a gene encoding a dihydroxy acid dehydratase, a gene encoding a decarboxylase, and one or both of a gene encoding a phenylacetaldehyde dehydrogenase and a gene encoding an aldehyde dehydrogenase. In some embodiments, the gene encoding an acetolactate synthase is an alsS gene, the gene encoding an acetohydroxy acid isomeroreductase is an ilvC gene, the gene encoding a dihydroxy acid dehydratase is an ilvD gene, the gene encoding a decarboxylase is a kivD gene, the gene encoding a phenylacetaldehyde dehydrogenase is a feaB gene and the gene encoding an aldehyde dehydrogenase is a puuC gene.

In some embodiments, the cell further recombinantly expresses one or both of a gene encoding a propionyl-CoA transferase and a gene encoding an isobutyryl-CoA ligase. In some embodiments, the gene encoding a propionyl-CoA transferase is a pct gene and the a gene encoding an isobutyryl-CoA ligase is an ibuA gene. In some embodiments, the cell further expresses a gene encoding a thioesterase.

In some embodiments, the cell is a bacterial cell, a fungal cell, a plant cell, an insect cell, or an animal cell. In some embodiments, the cell is a bacterial cell. In some embodiments, the bacterial cell is an *Escherichia coli* cell.

In some embodiments, one or more of the btkB, phaB and phaJ4b genes is a *Cupriavidus* gene, optionally a *Cupriavidus necator* gene. In some embodiments, the ter gene is a *Treponema* gene, optionally a *Treponema denticola* gene. In some embodiments, the car gene is a *Nocardia* gene, optionally a *Nocardia iowensis* gene. In some embodiments, the ADH6 gene is a *Saccharomyces* gene, optionally a *Saccharomyces cerevisiae* gene. In some embodiments, the yeaE gene is an *Escherichia* gene, optionally an *Escherichia coli* gene. In some embodiments, the alsS gene is a *Bacillus* gene, optionally a *Bacillus subtilis* gene. In some embodiments, one or more of the ilvC gene, the ilvD gene, the feaB gene and the puuC gene is an *Escherichia* gene, optionally an *Escherichia coli* gene. In some embodiments, the kivD gene is a *Lactococcus* gene, optionally a *Lactococcus lactis* gene. In some embodiments, the pct gene is a *Megasphaera* gene, optionally a *Megasphaera elsdenii* gene. In some embodiments, the ibuA gene is a *Rhodopseudomonas* gene, optionally a *Rhodopseudomonas palustris* gene.

In some embodiments, the gene encoding a thioesterase is expressed endogenously. In other embodiments, the gene encoding a thioesterase is recombinantly expressed. In some embodiments, the gene encoding a thioesterase is a tesB gene or a ydiI gene.

In some embodiments, one or more of bktB, phaB, phaJ4b, ter, car, ADH6, yeaE, alsS, ilvC, ilvD, kivD, feaB, puuC, pct, ibuA, tesB and ydiI is expressed from a plasmid. In some embodiments, at least one copy of one or more of bktB, phaB, phaJ4b, ter, car, ADH6, yeaE, alsS, ilvC, ilvD, kivD, feaB, puuC, pct, ibuA, tesB and ydiI is integrated into the genome of the cell. In some embodiments, expression of one or more of bktB, phaB, phaJ4b, ter, car, ADH6, yeaE, alsS, ilvC, ilvD, kivD, feaB, puuC, pct, ibuA, tesB and ydiI is regulated by one or more inducible promoter(s).

In some embodiments, the cell produces a branched medium-chain alcohol. In some embodiments, the branched medium chain alcohol is 4-methyl-1-pentanol.

Aspects of the invention relate to a cell culture or supernatant collected from culturing one or more cell(s) of any one of cells described herein.

Aspects of the invention relate to a method involving culturing the cell of any one of the cells described herein, in cell culture medium. In some embodiments, glucose is added to the cell culture medium. In some embodiments, isobutyrate is added to the cell culture medium. In some embodiments, the cell culture or supernatant contains at least 10 mg/L 4-methyl-1-pentanol. In some embodiments, the 4-methyl-1-pentanol is further purified from the cell culture or supernatant.

Further aspects of the invention relate to a method for producing 4-methyl-1-pentanol comprising culturing any of cells described herein.

Aspects of the invention relate to a method involving recombinantly expressing in a cell a gene encoding a thiolase, a gene encoding an acetoacetyl-CoenzymeA (CoA) reductase, a gene encoding an acyl dehydratase, a gene encoding an enoyl-CoA reductase, and a gene encoding a carboxylic acid reductase.

In some embodiments, the gene encoding a thiolase is a bkB gene, the gene encoding an acetoacetyl-CoenzymeA (CoA) reductase is a phaB gene, the gene encoding an acyl dehydratase is a phaJ4b gene, the gene encoding an enoyl-CoA reductase is a ter gene, and the gene encoding a carboxylic acid reductase a car gene. In some embodiments, the cell further recombinantly expresses one or both of a gene encoding an alcohol dehydrogenase and a gene encoding an aldo-keto reductase. In some embodiments, the gene encoding an alcohol dehydrogenase is an ADH6 gene and the gene encoding an aldo-keto reductase is a yeaE gene. In some embodiments, the alcohol dehydrogenase is an lsadh gene.

In some embodiments, the cell further recombinantly expresses one or more of a gene encoding an acetolactate synthase, a gene encoding an acetohydroxy acid isomeroreductase, a gene encoding a dihydroxy acid dehydratase, a gene encoding a decarboxylase, and one or both of a gene encoding a phenylacetaldehyde dehydrogenase and a gene encoding an aldehyde dehydrogenase. In some embodiments, the gene encoding an acetolactate synthase is an alsS gene, the gene encoding an acetohydroxy acid isomeroreductase is an ilvC gene, the gene encoding a dihydroxy acid dehydratase is an ilvD gene, the gene encoding a decarboxylase is a kivD gene, the gene encoding a phenylacetaldehyde dehydrogenase is afeaB gene and the gene encoding an aldehyde dehydrogenase is a puuC gene.

In some embodiments, the cell further recombinantly expresses one or both of a gene encoding a propionyl-CoA transferase and a gene encoding an isobutyryl-CoA ligase. In some embodiments, the gene encoding a propionyl-CoA transferase is a pct gene and the a gene encoding an isobutyryl-CoA ligase is an ibuA gene. In some embodiments, the cell further expresses a gene encoding a thioesterase.

In some embodiments, the cell is a bacterial cell, a fungal cell, a plant cell, an insect cell, or an animal cell. In some embodiments, the cell is a bacterial cell. In some embodiments, the bacterial cell is an *Escherichia coli* cell.

In some embodiments, one or more of the btkB, phaB and phaJ4b genes is a *Cupriavidus* gene, optionally a *Cupriavidus necator* gene. In some embodiments, the ter gene is a *Treponema* gene, optionally a *Treponema denticola* gene. In some embodiments, the car gene is a *Nocardia* gene, optionally a *Nocardia iowensis* gene. In some embodiments, the ADH6 gene is a *Saccharomyces* gene, optionally a *Saccharomyces cerevisiae* gene. In some embodiments, the lsadh gene is a *Leifsonia* gene, optionally a *Leifsonia* sp. Strain S749 gene. In some embodiments, the yeaE gene is an *Escherichia* gene, optionally an *Escherichia coli* gene. In some embodiments, the alsS gene is a *Bacillus* gene, optionally a *Bacillus subtilis* gene. In some embodiments, one or more of the ilvC gene, the ilvD gene, the feaB gene and the puuC gene is an *Escherichia* gene, optionally an *Escherichia coli* gene. In some embodiments, the fjoh2967 gene is a *Flavobacterium* gene, optionally a *Flavobacterium johnsonaie* gene. In some embodiments, the kivD gene is a *Lactococcus* gene, optionally a *Lactococcus lactis* gene. In some embodiments, the pct gene is a *Megasphaera* gene, optionally a *Megasphaera elsdenii* gene. In some embodiments, the ibuA gene is a *Rhodopseudomonas* gene, optionally a *Rhodopseudomonas palustris* gene.

In some embodiments, the gene encoding a thioesterase is expressed endogenously. In other embodiments, the gene encoding a thioesterase is recombinantly expressed.

In some embodiments, the gene encoding a thioesterase is a tesB gene or a ydiI gene.

In some embodiments, one or more of bktB, phaB, phaJ4b, ter, car, ADH6, yeaE, alsS, ilvC, ilvD, kivD, feaB, puuC, pct, ibuA, tesB, lsadh, fjoh2967, and ydiI is expressed from a plasmid. In some embodiments, at least one copy of one or more of bktB, phaB, phaJ4b, ter, car, ADH6, yeaE, alsS, ilvC, ilvD, kivD, feaB, puuC, pct, ibuA, tesB lsadh, fjoh2967, and ydiI is integrated into the genome of the cell. In some embodiments, expression of one or more of bktB, phaB, phaJ4b, ter, car, ADH6, yeaE, alsS, ilvC, ilvD, kivD, feaB, puuC, pct, ibuA, tesB lsadh, fjoh2967 and ydiI is regulated by one or more inducible promoter(s).

In some embodiments, the cell produces a branched medium-chain alcohol. In some embodiments, the branched medium chain alcohol is 4-methyl-1-pentanol.

Aspects of the invention relate to a cell that recombinantly expresses a module that condenses acetyl CoA and isobutyryl-CoA and reduces the product to form 4-methyl valeryl-CoA and a module that reduces 4-methyl valerate to 4-methyl-1-pentanol. In some embodiments, the cell further recombinantly expresses a module that converts pyruvate to isobutyrate. In some embodiments, the cell further recombinantly expresses a module that activates isobutyrate to isobutyryl-CoA. In some embodiments, the cell expresses a thioesterase that hydrolyzes 4-methyl valeryl-CoA to 4-methyl valerate.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 depicts tuning of pathway selectivity by the carboxylic acid reductase $Car_{Ni}$. FIG. 2A shows in vitro analysis of his-purified $Car_{Ni}$ that reveals a dependence on acid primary-chain length with maximum activity at a chain length of five and six carbons. In some embodiments, branching at the C4 position is preferred over straight acid species. The potential substrates for byproduct formation, butyrate and isobutyrate, are seen to have 56% and 25% of the observed activity on 4-methyl-valerate, respectively. FIG. 2B depicts Michaelis-Menton kinetics for isobutyrate and 4-methyl-valerate, revealing that $Car_{Ni}$ has a strong preference for the latter intermediate. FIG. 2C reveals how the substrate preference of $Car_{Ni}$ influences product selectivity in vivo, generating 1.9 times as much 4-methyl-pentanol (272 mg/L, 2.7 mM) as butanol (142 mg/L, 1.9 mM) in strains supplied with both glucose and isobutyrate. Even though 10 mM isobutyrate is supplied to the cultures of Strain M2P34 only 111 mg/L (1.5 mM) isobutanol is observed.

FIG. 4 reveals identification of Module 3 enzymes.

FIG. 7A shows that when cultures are supplemented with 1.2% glucose, pentanol is only observed with the $car_{Ni}$-$sfp_{Bs}$-$ADH6_{Sc}$ Module 4, presumably due to the inactivity of $adhE_{Ca}$ under aerobic conditions. Strain M1Pr3Cn4csA produces the highest butanol (475±21 mg/L) and pentanol (96±24 mg/L) titers under the conditions tested. M1Pr3Ca4csA produces 283±52 mg/L of butanol and 40±15 mg/L of pentanol. FIG. 7B shows that with 1.2% glycerol supplementation, the same trend for choice of Module 4 holds with pentanol, observed only with $car_{Ni}$-$sfp_{Bs}$-$ADH6_{Sc}$. Selectivity of the pathway is enhanced for both Strains M1Pr3Ca4csA and M1Pr3Cn4csA. Strain M1Pr3Ca4csA generates a butanol titer of 195±33 mg/L and a pentanol titer of 101±16 mg/L. The combination of $phaB_{Cn}$, $phaJ4b_{Cn}$, $car_{Ni}$-$sfp_{Bs}$, and $ADH6_{Sc}$ in Strain M1Pr3Cn4csA actually leads to pentanol as the preferred alcohol product with a butanol titer of 132±12 mg/L and a pentanol titer of 165±32 mg/L.

FIG. 11 depicts balancing of upstream pathway flux by controlling $alsS_{Bs}$ expression.

FIG. 17 shows a non-limiting example of a 4-methyl-pentanol (4MP) pathway schematic and alternative biofuel pathways. FIG. 17A shows the α-ketoacid elongation (αKAE) pathway was previously used to synthesize 4-methyl-1-pentanol among other products. The αKAE route utilizes relatively inefficient single-carbon extension and non-specific decarboxylation and reduction of upstream precursors resulting in a redox imbalance and a mix of products, three of which are shown. FIG. 17B depicts the CoA-dependent pathway to 4-methyl-1-pentanol assembled with genes from 9 organisms taken from 10 different pathway contexts. Pathway genes are shown with known native pathways or putative metabolic roles. Selectivity for 4-methyl-1-pentanol was achieved while requiring enzymes for Modules 3 and 4 to act on noncognate substrates. FIG. 17C shows that the 4-methyl-1-pentanol pathway can be organized into 4 modules which were used to identify better performing enzymes for individual steps and validate portions of the overall pathway independently in vivo: Module 1, modified valine biosynthesis to isobutyrate; Module 2, isobutyrate activation to isobutyryl-CoA; Module 3, CoA-dependent condensation and reduction of isobutyryl-CoA and acetyl-CoA to 4-methyl-valerate; Module 4, reduction of 4-methyl-valerate to 4-methyl-1-pentanol. Genes in italics were overexpressed from plasmid sets. Modules were constructed working backwards from the 4-methyl-1-pentanol product. A potential byproduct shunt to butyrate and butanol was monitored during pathway construction.

FIG. 18 shows 4-methyl-1-pentanol synthesis from glucose is improved through aldehyde dehydrogenase selection.

FIG. 19 shows improved alcohol dehydrogenase selectivity with lsadh$_{Ls}$.

FIG. 20 shows energy density and research octane number (RON) of short- and medium-chain primary alcohols.

FIG. 22 depicts results from assays for carboxylic acid reductase selectivity.

FIG. 23 shows initial 4-methyl-valerate and 4-methyl-1-pentanol synthesis from glucose using pct$_{Me}$ as Module 2.

FIG. 24 shows improved pathway performance through gene expression constructs.

FIG. 26 shows product profiles of high 4-methyl-1-pentanol producer and selective producer. FIG. 26A shows strains M1Fj(IA)2I34 and M1Fj(IA)2I34L express the full pathway using the Fjoh2967$_{Fj}$ aldehyde dehydrogenase and ibuA$_{Rp}$ isobutyryl-CoA synthetase with either the ADH6$_{Sc}$ (M1Fj(IA)2I34) or lsadh$_{Ls}$ (M1Fj(IA)2I34L) alcohol dehydrogenase. The broadly active ADH6$_{Sc}$ leads to production of 193±23 mg/L of 4MP and 797±20 mg/L of isobutanol while the contextually specific lsadh$_{Ls}$ produces 90±7 mg/L of 4-methyl-1-pentanol and 21±3 mg/L isobutanol. Isobutanol titers with lsadh$_{Ls}$ are similar to those observed with strains not overexpressing an alcohol dehydrogenase (M1P2P3, M1F2P3. M1F(IA)2I34a). FIG. 26B shows molar yields calculated for major products from both Strain M1Fj(IA)2I34 and Strain M1Fj(IA)2I34L. Both strains consumed 10 g/L glucose. The dominant byproducts acetate, isobutyrate, and isobutanol from Strain M1Fj(IA)2I34 account for 37.5% of the moles of glucose consumed. Isobutyrate and acetate from Strain M1Fj(IA)2I34L account for 31.8% of the moles of glucose consumed. FIG. 26C shows Module 4 enzymes expressed from pACYC-(car$_{Ni}$-sfp$_{Bs}$)-ADH6$_{Sc}$ and pACYC-(car$_{Ni}$-sfp$_{Bs}$)-lsadh$_{Ls}$ in the production strain MG1655(DE3) endA recA. Both alcohol dehydrogenases Adh6p$_{Sc}$ (42.5 KD, merges with background protein band) and Lsadh$_{Ls}$ (25 KD) were overexpressed well in MG1655 (DE3) endA recA. The reduction in 4-methyl-1-pentanol titer with Lsadh$_{Ls}$ likely results from lower levels of the required cofactor NADH under the aerobic conditions used. Adh6p$_{Sc}$ requires NADPH.

DETAILED DESCRIPTION OF INVENTION

Figures 1A, 1B, 1C, 1D:
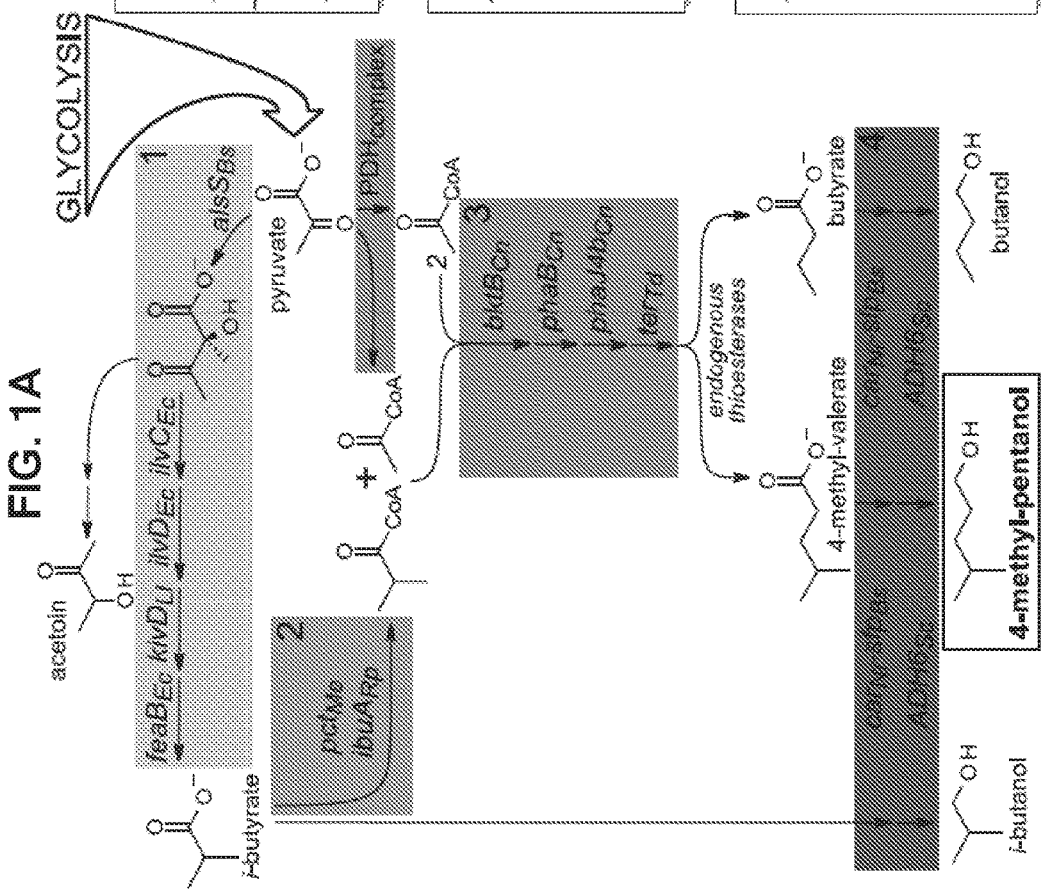
FIG. 1A schematically presents a non-limiting embodiment of a pathway described herein for production of 4-methyl-1-pentanol, organized into 4 modules that were used to identify enzymes for individual steps and validate portions of the overall pathway independently in vivo. Genes in italics were overexpressed from plasmid sets while the alsS gene was integrated into the genome for independent control of expression.
FIG. 1B schematically shows the α-ketoacid elongation (αKAE) pathway which utilizes relatively inefficient single-carbon extension and non-specific decarboxylation and reduction of upstream precursors.
FIG. 1C schematically depicts how use of the fatty acid biosynthesis pathway generally relies on recombinant thioesterases with longer chain specificity to siphon off growing fatty acyl-ACP intermediates.
FIG. 1D schematically shows that the isoprenoid biosynthesis can be used to generate the C5 alcohol isopentenol or longer chain compounds in multiples of five carbons.

Described herein is the surprising discovery that branched medium-chain alcohols can be produced by a biological process involving metabolic engineering through recombinant gene expression in cells. Methods and compositions of the invention relate to the production of 4-methyl-1-pentanol in a cell that recombinantly expresses genes encoding a thiolase, an acetoacetyl-CoA reductase, an acyl dehydratase, an enoyl-CoA reductase, and a carboxylic acid reductase. Rather than a simple transfer of a single recombinant pathway, the novel pathway herein comprises enzymes from multiple organisms and multiple natural metabolic pathways. A primary advantage of such a pathway is the ability to select enzymes that extend carbon chains to specific lengths, like medium-chain and branched species, helping to improve extension specificity.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations of thereof herein, is meant to encompass the items listed thereafter and equivalents thereof as well as additional items.

Methods and compositions described herein relate to the development of a novel pathway to produce branched medium-chain alcohols, such as 4-methyl-1-pentanol, from sugar substrates. In some embodiments the number of carbon molecules in the chain is 5, 6, or 7. In some embodiments the product of the pathway is a primary alcohol. In other embodiments, the product is a secondary or tertiary alcohol. In some embodiments, the branched medium-chain alcohol produced is 4-methyl-1-pentanol. As used herein, "4-methyl-pentanol," "4MP" and "4-methyl-1-pentanol" are used interchangeably and all refer to 4-methyl-1-pentanol.

The 4-methyl-1-pentanol Pathway

A schematic of the novel pathway for production of 4-methyl-1-pentanol described herein is depicted in FIG. 1. In methods and compositions associated with the invention, the 4-methyl-1-pentanol pathway can be divided into at least four modules. As used herein, a "module" refers to a combination of one or more components. In some embodiments, the components of the modules pertain to nucleic acid. In some embodiments the nucleic acid is a gene encoding a protein, specifically an enzyme with a desired function. In some embodiments the enzymes within a module function sequentially to process a molecule. In some embodiments, the biosynthetic pathway is divided into modules to aid in assessing the efficiency of each portion of the pathway. In some embodiments, the biosynthetic pathway is divided into modules to aid in selection of enzymes with desired functions. In some embodiments, all four modules depicted in FIG. 1 are expressed in a cell. In other embodiments, fewer than all four modules are expressed in a cell. For example, one, two, three or four modules as described herein, and as depicted in FIG. 1, can be expressed in a cell.

In Module 1, pyruvate, generated by the glycolytic pathway, is converted into α-ketoisovalerate (α-KIV) and then further converted to isobutyrate. In some embodiments, α-KIV is produced using enzymes that are naturally involved in an amino acid biosynthesis pathway. In some embodiments, the enzymes are naturally involved in the valine biosynthesis pathway. In some embodiments, pyruvate is converted to α-KIV through the activity of an acetolactate synthase, an acetohydroxy acid isomeroreductase, and a dihydroxy acid dehydratase. In some embodiments, the acetolactate synthase activity is performed by an enzyme encoded by an alsS gene. In some embodiments, the acetohydroxy acid isomeroreductase activity is performed by an enzyme encoded by an ilvC gene. In some embodiments the dihydroxy acid dehydratase activity is performed by an enzyme encoded by an ilvD gene. α-KIV is further converted to isobutyrate. In some embodiments α-KIV is converted to isobutyrate through the activities of a decarboxylase and an aldehyde dehydrogenase. In other embodiments α-KIV is converted to isobutyrate through the activities of a decarboxylase and a phenylacetaldehyde dehydrogenase. In some embodiments, the decarboxylase activity is performed by an enzyme encoded by the kivD gene. In some embodiments, the aldehyde dehydrogenase activity is performed by an enzyme encoded by the puuC gene. In some embodiments, the phenylacetaldehyde dehydrogenase activity is performed by an enzyme encoded by the feaB gene. In some embodiments, the aldehyde dehydrogenase activity is performed by an enzyme encoded by the Fjoh2967 gene.

In some embodiments, isobutyrate from Module 1 is used as a substrate for Module 2. In other embodiments, isobutyrate supplied in the culture medium is used as a substrate for Module 2. In Module 2 isobutyrate is converted into isobutyryl-CoA. As used herein, isobutyryl-CoA is referred to as "activated" isobutryate, and the process used to generate isobutyryl-CoA from isobutyrate is referred to as "activation". In some embodiments, isobutyrate is activated to isobutyryl-CoA by a propionyl-CoA transferase and an isobutyryl-CoA ligase. In some embodiments, the propionyl-CoA transferase activity is performed by an enzyme encoded by the pct gene. In some embodiments, the isobutyryl-CoA ligase activity is performed by an enzyme encoded by the ibuA gene. In some embodiments isobutyryl-CoA produced by Module 2 will function as the substrate for Module 3.

Acetyl-CoA is provided to Module 3 through the activity of the pyruvate decarboxylase complex. In some embodiments, one or more components of the pyruvate decarboxylase complex is expressed endogenously. In some embodiments one or more components of the pyruvate decarboxylase complex is recombinantly expressed. In Module 3, acetyl-CoA is condensed with isobutyryl-CoA and further reduced to produce 4-methyl-valeryl-CoA. In some embodiments, acetyl-CoA is condensed with isobutyryl-CoA to form a branched 3-keto-4-methylvaleryl-CoA intermediate. In some embodiments, the branched 3-keto-4-methylvaleryl-CoA intermediate is produced by an enzyme with thiolase activity. In some embodiments, the thiolase activity is performed by an enzyme encoded by the bktB gene. The branched 3-keto-4-methylvaleryl-CoA intermediate is reduced to form 4-methyl-valeryl-CoA by sequential activity of an acetoacetyl-CoA reductase, an acyl dehydratase, and an enoyl-CoA reductase. In some embodiments, the acetoacetyl-CoA reductase activity is performed by an enzyme encoded by the phaB gene. In some embodiments, the acyl dehydratase reductase activity is performed by an enzyme encoded by the phaJ4b gene. In some embodiments, the enoyl-CoA reductase activity is performed by an enzyme encoded by the ter gene.

In some embodiments, the 4-methyl-valeryl-CoA produced by Module 3 will be further processed to generate 4-methyl-valerate. In some embodiments, 4-methyl-valerate is produced by an enzyme with thioesterase activity. The enzyme with thioesterase activity can be endogenously and/or recombinantly expressed. In some embodiments, the enzyme with thioesterase activity is encoded by the tesB or ydiI genes.

4-methyl-valerate is reduced to 4-methyl-1-pentanol in Module 4. In some embodiments, 4-methyl-valerate is reduced by enzymes with carboxylic acid reductase activity and alcohol dehydrogenase activity. In other embodiments 4-methyl-valerate is reduced by enzymes with carboxylic acid reductase activity and aldo-ketoreductase activity. The carboxylic acid reductase activity can be performed by an enzyme encoded by the car gene. In some embodiments the alcohol dehydrogenase activity is performed by an enzyme encoded by the ADH6 gene. In some embodiments the aldo-ketoreductase activity is performed by an enzyme encoded by the yeaE gene.

In preferred embodiments, a cell comprises Module 3, such that 4-methyl-valerate is produced from the substrates acetyl-CoA and isobutyryl-CoA that may be present in the cell. In other embodiments, a cell additionally comprises Module 4, such that 4-methyl-1-pentanol is produced from 4-methyl-valerate. In other embodiments, the cell further expresses either one or both of Module 1 and Module 2 in addition to Module 3 and Module 4. In such embodiments, glucose may be the substrate for production of 4-methyl-1-pentanol. In some embodiments, the cell comprises a thioesterase.

Any intermediate molecule produced in any of Modules 1-4 may be quantified to assess the function of a given Module(s). In some embodiments, 4-methyl-valerate production is measured to assess the function of Module 3. In some embodiments, 4-methyl-valerate production is measured to assess the function of Modules 1-3. In other embodiments. 4-methyl-1-pentanol is quantified to assess the function of Module 4. In other embodiments, 4-methyl-1-pentanol is quantified to assess the function of Modules 1-4. In some embodiments, one or more desired or undesired products may be quantified to assess the function or selectivity of one or more modules. In some embodiments, the product is butanol. In some embodiments, the product is pentanol. In some embodiments, the enzymes of a given module are selected based on the ratio of the amount of 4-methyl-1-pentanol to another desired or undesired product produced.

According to aspects of the invention, cell(s) that recombinantly express one or more genes associated with the invention, and the use of such cells in producing branched medium chain alcohols, such as 4-methyl-1-pentanol, are provided. It should be appreciated that the genes associated with the invention can be obtained from a variety of sources. In some embodiments, the btkB, phaB, and phaJ4b genes are obtained from a strain of *Cupriavidus necator*, such as *Cupriavidus necator* H16, the ter gene is obtained from a strain of *Treponema denticola*, such as *Treponema denticola* ATCC-35405, the car gene is obtained from a strain of *Nocardia iowensis*, such as *Nocardia iowensis* DSM 45197, the ADH6 gene is obtained from a strain of *Saccharomyces cerevisiae*, such as *Saccharomyces cerevisiae* S288c, the yeaE, ilvC, ilvD, feaB, puuC, ydiI, and tesB genes are obtained from a strain of *Escherichia coli*, such as *Escherichia coli MG1655, the kivD gene is obtained from a strain of *Lactococcus lactis*, such as a *Lactococcus lactis* subsp. *lactis* KF147, the pct gene is obtained from a strain of *Megasphaera elsedenii*, such as a *Megasphaera elsedenii* BE2-2083, the ibuA gene is obtained from a strain of *Rhodopseudomonoas palustris*, such as *Rhodopseudomonoas palustris* CGA009. It should be appreciated that any of the nucleic acids and/or polypeptides described herein can be codon-optimized and expressed recombinantly in a codon-optimized form.

As one of ordinary skill in the art would be aware, homologous genes for these enzymes could be obtained from other species and could be identified by homology searches, for example through a protein BLAST search, available at the National Center for Biotechnology Information (NCBI) internet site (ncbi.nlm.nih.gov). Genes associated with the invention can be PCR amplified from DNA from any source of DNA which contains the given gene. In some embodiments, genes associated with the invention are synthetic. Any means of obtaining a gene encoding the enzymes associated with the invention are compatible with the instant invention.

The invention thus involves recombinant expression of genes encoding enzymes discussed above, functional modifications and variants of the foregoing, as well as uses relating thereto. Homologs and alleles of the nucleic acids associated with the invention can be identified by conventional techniques. Also encompassed by the invention are nucleic acids that hybridize under stringent conditions to the nucleic acids described herein. The term "stringent conditions" as used herein refers to parameters with which the art is familiar. Nucleic acid hybridization parameters may be found in references which compile such methods, e.g. Molecular Cloning: A Laboratory Manual, J. Sambrook, et al., eds., Fourth Edition, Cold Spring Harbor Laboratory Press, Cold Spring Harbor, N.Y., 2012, or Current Protocols in Molecular Biology. F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH2PO4 (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/ 0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity and/or at least 90% amino acid identity to the sequences of nucleic acids and polypeptides, respectively, in some instances will share at least 90% nucleotide identity and/or at least 95% amino acid identity and in still other instances will share at least 95% nucleotide identity and/or at least 99% amino acid identity. The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention embraces variants of polypeptides. As used herein, a "variant" of a polypeptide is a polypeptide which contains one or more modifications to the primary amino acid sequence of the polypeptide. Modifications which create a variant can be made to a polypeptide 1) to reduce or eliminate an activity of a polypeptide; 2) to enhance a property of a polypeptide; 3) to provide a novel activity or property to a polypeptide, such as addition of an antigenic epitope or addition of a detectable moiety; or 4) to provide equivalent or better binding between molecules (e.g., an enzymatic substrate). Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence. One of skill in the art will be familiar with methods for predicting the effect on protein conformation of a change in protein sequence, and can thus "design" a variant of a polypeptide according to known methods. One example of such a method is described by Dahiyat and Mayo in Science 278:82 87, 1997, whereby proteins can be designed de novo. The method can be applied to a known protein to vary only a portion of the polypeptide sequence. By applying the computational methods of Dahiyat and Mayo, specific variants of a polypeptide can be proposed and tested to determine whether the variant retains a desired conformation.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., E. coli, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides. i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, N.Y., 2012, or Current Protocols in Molecular Biology, F. M. Ausubel, et al., eds., John Wiley & Sons. Inc., New York. Exemplary functionally equivalent variants of polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, 20 residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of a polypeptide to produce functionally equivalent variants of the polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488-492, 1985), or by chemical synthesis of a gene encoding a polypeptide.

The invention encompasses any type of cell that recombinantly expresses genes associated with the invention, including prokaryotic and eukaryotic cells. In some embodiments the cell is a bacterial cell, such as Escherichia spp., Streptomyces spp., Zymonas spp., Acetobacter spp., Citrobacter spp., Synechocystis spp., Rhizobium spp., Clostridium spp., Corynebacterium spp., Streptococcus spp., Xanthomonas spp., Lactobacillus spp., Lactococcus spp., Bacillus spp., Alcaligenes spp., Pseudomonas spp., Aeromonas spp., Azotobacter spp., Comamonas spp., Mycobacterium spp., Rhodococcus spp., Gluconobacter spp., Ralstonia spp., Acidithiobacillus spp., Microlunatus spp., Geobacter spp., Geobacillus spp., Arthrobacter spp., Flavobacterium spp., Serratia spp., Saccharopolyspora spp., Thermus spp., Stenotrophomonas spp., Chromobacterium spp., Sinorhizobium spp., Saccharopolyspora spp., Agrobacterium spp. and *Pantoea* spp. The bacterial cell can be a Gram-negative cell such as an *Escherichia coli* (*E. coli*) cell, or a Gram-positive cell such as a species of *Bacillus*. In other embodiments the cell is a fungal cell such as yeast cells, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments the cell is an algal cell, a plant cell, or a mammalian cell. It should be appreciated that some cells compatible with the invention may express an endogenous copy of one or more of the genes associated with the invention as well as a recombinant copy. In some embodiments if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of 4-methyl-1-pentanol.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., j-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, Fourth Edition, Cold Spring Harbor Laboratory Press, 2012. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production 4-methyl-1-pentanol, is demonstrated in the Examples section using *E. coli*. As one of ordinary skill in the art would appreciate, the novel method for producing 4-methyl-1-pentanol can also be expressed in other bacterial cells, archaeal cells, fungi (including yeast cells), mammalian cells, plant cells, etc.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction. ATCC Trace Mineral Supplement, glycolate and propionate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of branched medium-chain alcohols such as 4-methyl-1-pentanol. In some embodiments the concentration and amount of a supplemental component may be optimized. In some embodiments, how often the media is supplemented with one or more supplemental components, and the amount of time that the media is cultured before harvesting 4-methyl-1-pentanol is optimized.

According to aspects of the invention, high titers of 4-methyl-1-pentanol are produced through the recombinant expression of genes associated with the invention, in a cell. As used herein, "high titer" refers to a titer in the milligrams per liter (mg $L^{-1}$) scale. The titer produced for a given product will be influence by multiple factors including the choice of media.

In some embodiments, the titer of 4-methyl-1-pentanol is at least 10 mg $L^{-1}$. For example, the titer can be at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more than 300 mg $L^{-1}$. In some embodiments, the titer of 4-methyl-1-pentanol is less than 10 mg $L^{-1}$. For example, the titer can be approximately 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3.9.4, 9.5, 9.6, 9.7, 9.8 or 9.9 mg $L^{-1}$.

Any liquid culture medium that allows growth of the cells can be used for the invention. In some embodiments the growth medium is Luria Broth (LB). In some embodiments of the methods associated with the invention, the growth medium is supplemented with glucose. In some embodiments the growth medium is supplemented with 1% glucose. In some embodiments, the growth medium is supplemented with isobutyrate. In certain embodiments, the growth medium is supplemented with approximately 10 mM isobutyrate. In some embodiments both glucose and isobuyrate are used to supplement the growth medium.

The liquid cultures used to grow cells associated with the invention can be housed in any of the culture vessels known and used in the art. In some embodiments large scale production in an aerated reaction vessel such as a stirred tank reactor can be used to produce large quantities of branched medium-chain alcohols like 4-methyl-1-pentanol.

Aspects of the invention include strategies to optimize production of 4-methyl-1-pentanol from a cell. Optimized production of 4-methyl-1-pentanol refers to producing a higher amount of 4-methyl-1-pentanol following pursuit of an optimization strategy than would be achieved in the absence of such a strategy. One strategy for optimization is to increase expression levels of one or more genes associated with the invention through selection of appropriate promoters and/or ribosome binding sites. In some embodiments, this may include the selection of high-copy number plasmids, or low or medium-copy number plasmids. In some embodiments, the plasmid is medium-copy number plasmid such as pETDuet. The step of transcription termination can also be targeted for regulation of gene expression, through the introduction or elimination of structure such as stem-loops.

In some embodiments, it may be advantageous to use a cell that has been optimized for production of 4-methyl-1-pentanol. In some embodiments, screening for one or more mutations that lead to enhanced production of 4-methyl-1-pentanol may be conducted through random mutagenesis, or through screening of known mutations. In some embodiments, shotgun cloning of genomic fragments can be used to identify genomic regions that lead to an increase in production of 4-methly-1-pentanol, through screening cells or organisms that have these fragments for production of 4-methyl-1-pentanol. In some cases on or more mutation may be combined in the same cell or organism.

Optimization of production of 4-methyl-1-pentanol can involve optimizing selection of bacterial strains for expression of recombinant pathways described herein. In some embodiments, use of a bacterial strain that is close to wild-type, meaning a strain that has not been substantially genetically modified, may lead to increased titers of 4-methyl-1-pentanol. For examples, in some embodiments, use of a bacterial strain which expresses recA and/or endA genes, such as E. coli strain MG1655 (DE3) leads to increased titers of 4-methyl-1-pentanol. In some embodiments use of E. coli MG1655 (DE3) recA$^-$ endA$^-$ leads to increased titers of 4-methyl-1-pentanol.

Optimization of protein expression may also require in some embodiments that a gene encoding an enzyme be modified before being introduced into a cell such through codon optimization for expression in a bacterial cell. Codon usages for a variety of organisms can be accessed in the Codon Usage Database (kasusa.or.jp/codon/).

In some embodiments, protein engineering can be used to optimize expression or activity of one or more enzymes associated with the invention. In certain embodiments a protein engineering approach could include determining the 3D structure of an enzyme or constructing a 3D homology model for the enzyme based on the structure of a related protein. Based on 3D models, mutations in an enzyme can be constructed and incorporated into a cell or organism, which could then be screened for an increase production of 4-methyl-1-pentanol. In some embodiments, production of 4-methyl-1-pentanol in a cell could be increase through manipulation of enzymes that act in the same pathway as the enzymes associated with the invention. For example in some embodiments it may be advantageous to increase expression of an enzyme or other factor that acts upstream of a target enzyme such as an enzyme associated with the invention. This could be achieved by over-expression of the upstream factor using any standard method.

The methods and compositions described herein for the production of 4-methyl-1-pentanol have widespread applications and value. Previous methods for the production of branched medium-chain alcohols have focused on modifying natural pathways, for example the α-keto-acid elongation pathway, fatty acid synthases or isoprenoid synthesis. These approaches have resulted in moderate yields of branched medium-chain alcohols, at best, making the use these molecules as a fuel source non-viable. The success of the novel modular synthetic pathway described herein for the production of 4-methyl-1-pentanol in a cell demonstrates that this is an attractive and economical method for the production of medium branched chain alcohols.

There are currently no processes for large volume production of the target alcohol described above. A small number of "fine" and "rare" chemical suppliers list 4-methyl-1-pentanol as a commercially available product. In addition some plants, such as Dimocarpus longan, are known to naturally produce small quantities of these and similar volatile alcohols in their fruit (Contis et al., 1997). Zhang et al. have also described an engineered pathway for production of 4-methyl-1-pentanol in E. coli with modest titers. The pathway described by Zhang utilizes engineered proteins of the aketoacid elongation pathway coupled to a ketoacid decarboxylase and alcohol dehydrogenase (Zhang et al., (2008) PNAS 105(52):20653-20658). The ketoacid decarboxylase pathway has lower theoretical yields from glucose compared to the pathway of the current description due to the loss of more carbon dioxide units during the extension of the branched amino acid pathway precursors during α-ketoacid elongation and an inbalance in the reducing equivalents produced and consumed in the pathway. The synthesis in the current description has the potential for higher yields of 4-methyl-pentanol, equal to those observed for ethanol, in large scale microbial fermentation.

4-methyl-1-pentanol is miscible with many organic solvents and could be used as a solvent for a variety of chemical reactions or extractions. US Patent Publication No. US2008/0249336A1 describes the use of C8 single branched primary alcohols as precursors for sulfation or epoxylation to form biodegradable detergents (Singleton et al., 2008). 4-methylpentanol can be used as a liquid fuel replacement for gasoline with high energy density and branches which improve octane rating.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1: Production of 4-Methyl-1-Pentanol in E. coli

Production of C4 and C5 straight- and branched-chain alcohols via the Ehrlich pathway utilizes the α-keto acids tailored for synthesis of specific amino acids. The valine intermediate, α-ketoisovalerate (α-KIV), is extended by one carbon using the α-keto-acid-elongation pathway (αKAE) to generate α-ketoisocaproate, a precursor of leucine. Further extension of α-ketoacids to make longer chain alcohols is rare in nature. αKAE has also been implicated as the pathway to medium-chain acids and alcohols in certain plant species (van der Hoeven 2000). Recently Zhang et al. used protein engineering to identify αKAE enzymes for the synthesis of medium-chain alcohols (Zhang 2008). However, the described αKAE pathway maintains preference for the synthesis of shorter intermediates and the overall pathway chemistry is inefficient, releasing one CO2 for every carbon added during elongation (FIG. 1B).

Contrarily, fatty acid synthases (FASs) prefer synthesis of long-chain fatty acids with pathway efficiency increasing with increasing chain length. Acyl-ACP thioesterases have been employed to terminate synthesis at shorter chain lengths in order to combat the tendency of FASs to extend to long chain lengths. Recently a multipronged approach of degrading fatty acid elongation ketosynthases in addition to expressing thioesterases was used in an attempt to shorten chain length even further (Silver, 2013). Such approaches, while innovative, are battling against a strong tendency of the natural pathway enzymes to generate longer products which has resulted in modest titers of desired products and much higher titers of related byproducts (FIG. 1C).

Isoprenoid synthesis is further limited by the use of isopentenyl diphosphate (IPP) as a C5 building block. IPP and its isomer dimethylallyl pyrophosphate (DMAPP), generated by the core mevalonate pathway, are strongly toxic intermediates requiring engineering to minimize intracellular concentrations (Whithers 2007). IPP and DMAPP from the mevalonate pathway can be used to produce C5 prenyl alcohol by a phosphatase reaction, while chain extension by condensation of IPP and DMAPP can generate C10 geranyl diphosphate and C15 farnesyl diphosphate as well as longer chain compounds (Withers 2007, U.S. Pat. No. 7,399,323 Renninger et al. Amyris) (FIG. 1D). The toxicity challenges and carbon structure limitations warrant exploration of alternative pathways to gasoline-like biofuels.

Fatty acid beta-oxidation-like pathways, first understood in the study of the ABE pathway of Clostridium acetobutylicum, are an intriguing alternative to those described above. CoA-dependent pathways which operate synthetically typically utilize acetyl-CoA building blocks and extend carbon chains through condensation reactions without release of CO2. The potential for generation of 2 reducing equivalents per acetyl-CoA generated from glycolysis perfectly balances with those consumed for reduction to a primary alcohol product. Reverse beta-oxidation has been demonstrated for synthesis of straight-chain acids and alcohols of a variety of chain lengths. An additional advantage of such pathways is the ability to select enzymes which extend carbon chains to specific lengths. Here we present the expansion of potential products of beta-oxidation-like pathways to branched alcohols of medium chain length. This novel 4-methylpentanol (4MP) pathway couples valine biosynthesis to CoA-dependent chain extension in a redox neutral manner (FIG. 1A). Importantly, the designed pathway is implemented using a thiolase and acid/aldehyde reductases with substrate preference for medium-chain and branched species helping to improve extension specificity. This 4-methyl-1-pentanol pathway does not rely on the simple transfer of a single recombinant pathway; rather it involves a patchwork of enzymes from multiple organisms and multiple natural pathways. FIG. 1 presents the overall pathway as a composite of 4 modules.

Results
Pathway Design for Medium-Chain Branched Alcohols

Figure 21:
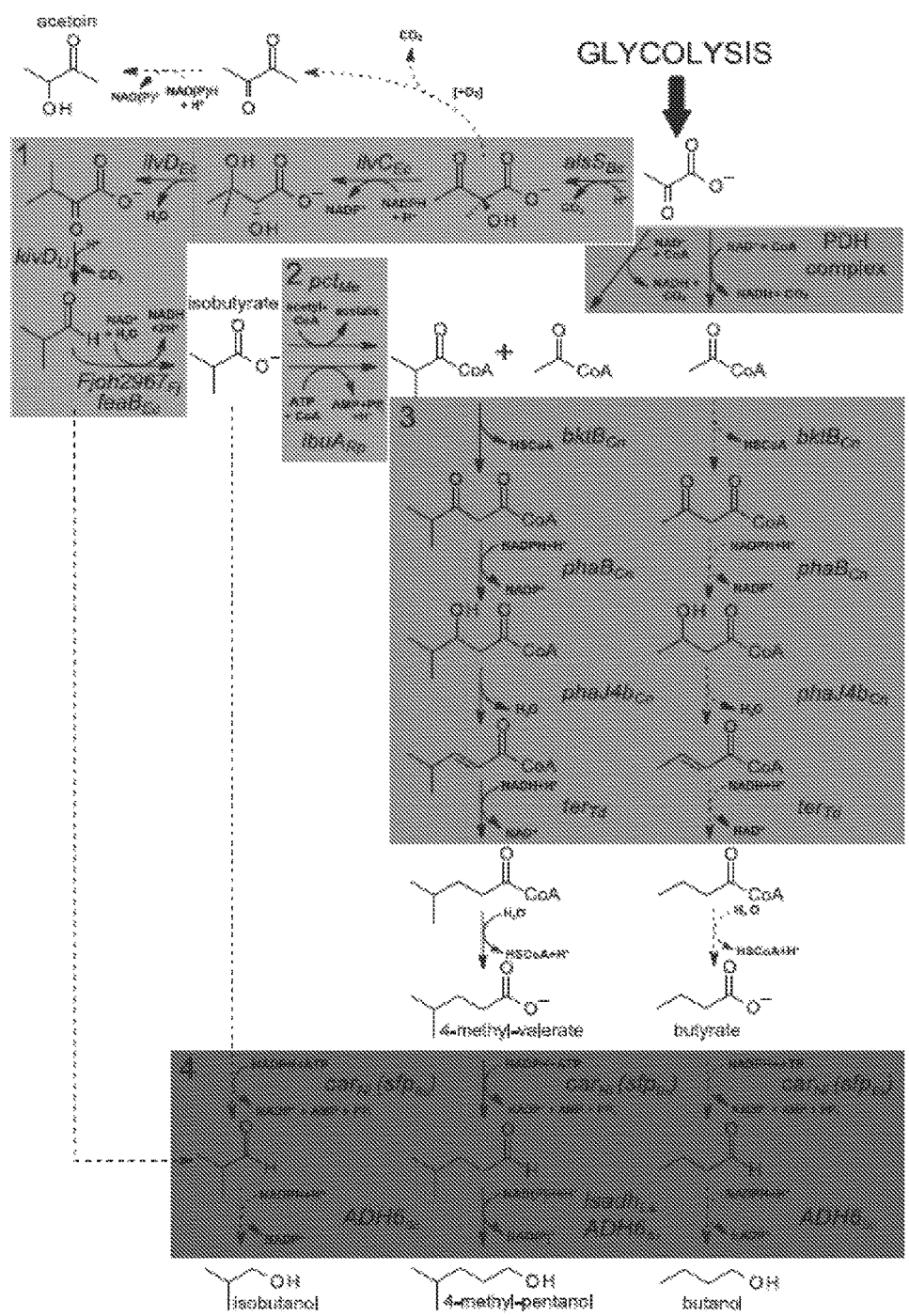
FIG. 21 shows a detailed schematic of non-limiting examples of modules of the full 4-methyl-1-pentanol pathway. Module 1 consists of *B. subtilis* acetolactate synthase alsS$_{Bs}$, *Escherichia coli* acetohydroxy acid isomeroreductase ilvC$_{Ec}$ and dihydroxy acid dehydratase ilvD$_{Ec}$, *Lactococcus lactis* α-ketoisovalerate decarboxylase kivD$_{Ll}$, and *Escherichia coli* aldehyde dehydrogenases feaB$_{Ec}$ or *Flavobacterium johnsoniae* aldehyde dehydrogenase Fjoh2967$_{Fj}$. Module 2 is one of two isobutyrate activators *Megasphaera elsdenii* propionyl-CoA transferase pct$_{Me}$ or *Rhodopseudomonas palustris* isobutyryl-CoA ligase ibuA$_{Rp}$. Module 3 contains the *Cupriavidus necator* thiolase bktB$_{Cn}$, 3-hydroxyacyl-CoA dehydrogenase phaB$_{Cn}$, and enoyl-CoA dehydratase phaJ4b$_{Cn}$ and *Treponema denticola* enoyl-CoA reductase ter$_{Td}$. Finally, Module 4 is composed of the *Nocardia iowensis* carboxylic acid reductase car$_{Ni}$ and *Saccharomyces cerevisiae* alcohol dehydrogenase ADH6$_{Sc}$ or *Leifsonia* sp. Strain S749 alcohol dehydrogenase lsadh$_{Ls}$.
Figure 22A:
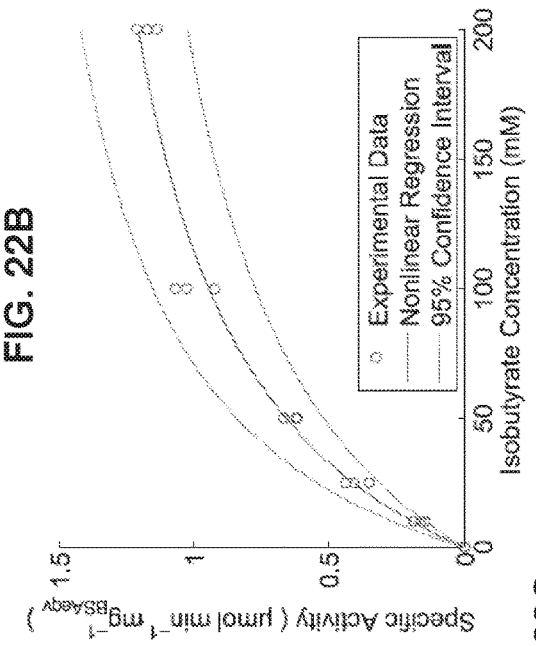
FIG. 22A shows results from an in vivo assay was developed to confirm Module 4 activity. Strain M4 expressing car-sfp-ADH6 was fed five different acids at 10 mM initial concentration. Selectivity was determined by measuring normalized titers 5 hours post induction of gene expression. As observed by in vitro analysis, the reduction rate appears to peak at species with a primary carbon chain length of 5 carbons. Transport and toxicity effects of the different acids are not decoupled from enzymatic activity effects in the in vivo assay. Michaelis-Menten curves for Car$_{Ni}$ with 4-methyl-valerate and isobutyrate were also found. Initial rates were measured by monitoring NADPH consumption by measuring absorption at 340 nm.
Figure 22B:
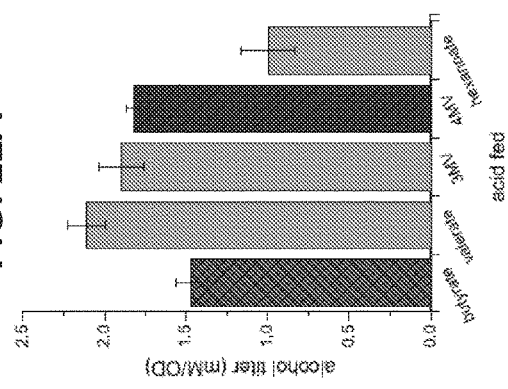
FIG. 22B presents rates for isobutyrate concentrations between 10 and 200 mM. The K$_m$ with isobutyrate was found to be 78±9 mM.
Figure 22C:
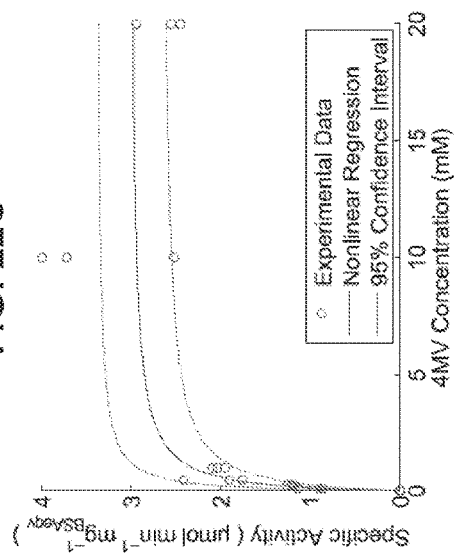
FIG. 22C presents rates for 4-methyl-valerate concentrations between 0.1 and 20 mM. The K$_m$ with 4MV was found to be 0.31±0.08 mM.

In a non-limiting embodiment, the 4-methyl-pentanol pathway design does not rely on the simple transfer of a single recombinant pathway; rather, it includes a patchwork of enzymes from multiple organisms and multiple natural pathways (FIG. 1A and FIG. 17C). FIG. 1A and FIG. 17 present a non-limiting examples of a pathway in which Module 1 converts pyruvate, from glycolysis, to α-ketoisovlaerate via valine biosynthesis using *Bacillus subtilis* acetolactate synthase alsS$_{Bs}$, *Escherichia coli* acetohydroxy isomeroreductase ilvC$_{Ec}$ and *E. coli* dihydroxy acid dehydratase ilvD$_{Ec}$. α-ketoisovlaerate is further converted to isobutyrate by the *Lactococcus lactis* decarboxylase kivD$_{Ll}$ and either the broad substrate accepting *E. coli* aldehyde dehydrogenase puuC$_{Ec}$ implicated in putrescine metabolism or the *E. coli* phenylacetaldehyde dehydrogenase feaB$_{Ec}$ (Jo 2008, Kurihara 2005, Ferrandez 1997, Zavala 2006). Alternatively. α-ketoisovlaerate is further converted to isobutyrate by the *Lactococcus lactis* decarboxylase kivD$_{Ll}$ and an isobutyraldehyde preferring aldehyde dehydrogenase from *Flavobacterium johnsonaie* Fjoh_2967 (Yamanaka 2002). Module 2 comprises two different activators which can be used to activate isobutyrate to isobutyryl-CoA: *Megasphaera elsdenii* propionyl-CoA transferase pct$_{Me}$ and *Rhodopseudomonas palustris* isobutyryl-CoA ligase ibuA$_{Rp}$. Alternatively, Module 2 can comprise the ATP-dependent activator *Rhodopseudomonas palustris* isobutyryl-CoA ligase IbuA$_{Rp}$, which converts isobutyrate to isobutyryl-CoA (Crosby 2012). Acetyl-CoA, generated by the endogenous pyruvate decarboxylase complex, condenses with isobutyryl-CoA in the first reaction of Module 3 conducted by the *Cupriavidus necator* thiolase bktB$_{Cn}$. The branched 3-keto-4-methylvaleryl-CoA intermediate is reduced to 4-methyl-valeryl-CoA by *C. necator* acetoacetyl-CoA reductase phaB$_{Cn}$, *C. necator* enoyl-CoA hydratase phaJ4b$_{Cn}$ and *T. denticola* enoyl-CoA reductase ter$_{Td}$ (Dennis 1998, Kawashima 2011, Hoffmeister 2005, Watts 2011, Tseng 2012, Martin 2013, Tucci 2007). Endogenous thioesterase activity, which can be derived from tesB and ydiI, generates free 4-methyl-valerate (McMahon 2014). In Module 4, the free 4-methyl-valerate can then be reduced to 4-methyl-1-pentanol by the *Nocardia iowensis* carboxylic acid reductase car$_{Ni}$ and either *Saccharomyces cerevisiae* alcohol dehydrogenase ADH6$_{Sc}$ or *Leifsonia* sp. Strain S749 alcohol dehydrogenase lsadh (Larroy 2002, Li 1997, Venkitasubramanian 2006, Inonue 2006, Inonue 2005). FIG. 21 presents enzyme cofactor requirements and byproduct reactions. Tables 1 and 5 present descriptions of strains used, and Table 6 presents relevant descriptions of enzymes used in pathway variants. Strain names indicate the modules present in the strain (i.e., M1F2I34 includes "M" for modules, "F" for Module 1 with feaB$_{Ec}$, "21" for Module 2 with ibuA$_{Rp}$, "3" for Module 3, and "4" for Module 4). Strain names with "( )" contain abbreviations for operon structure indicating the order of alsS$_{Bs}$ and ilvC$_{Ec}$ (i.e., M1F(IA)2I34 includes (IA) indicating an ilvC$_{Ec}$-alsS$_{Bs}$ operon order).

Identification of 3-Hydroxy-4-Methyl-Valeryl-CoA Dehydratases and 4-Methyl-Trans-2-Pentenyl-CoA Reductases (Module 3).

Figures 4A, 4B:
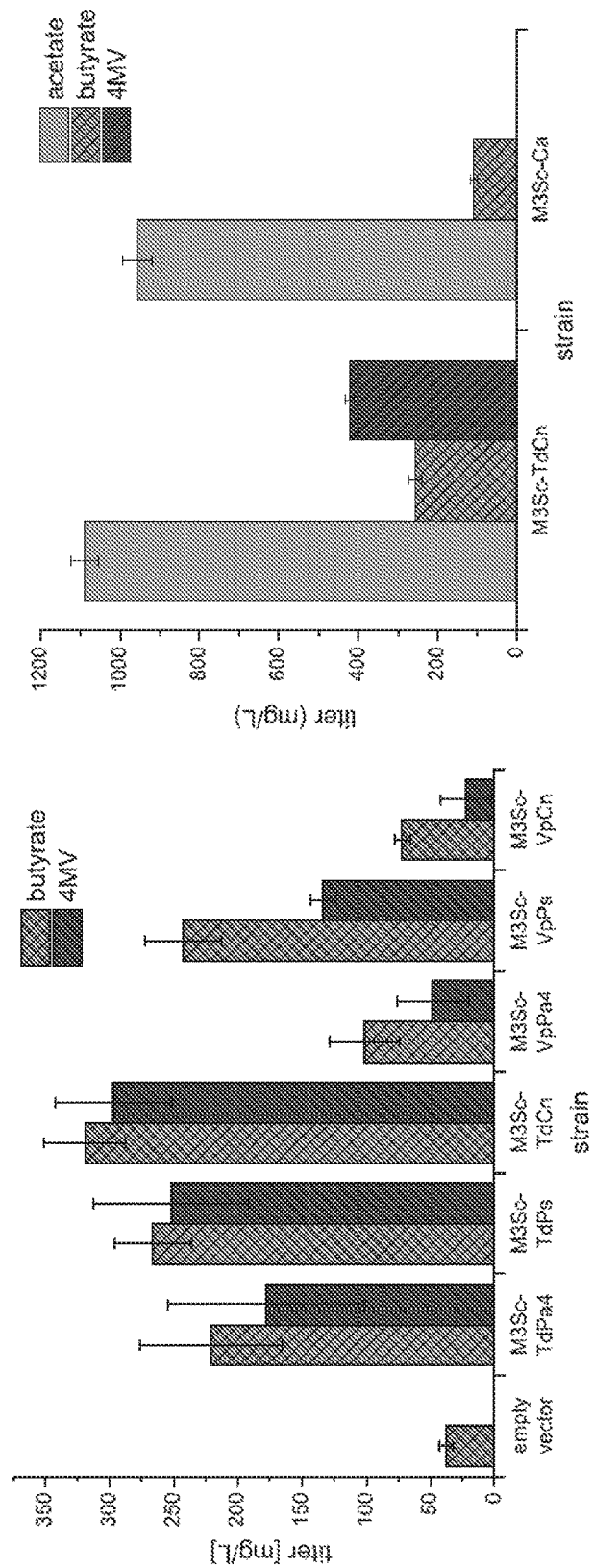
FIG. 4A demonstrates that of the 24 combinations of 3-hydroxyacyl-CoA dehydratases (phaJ) and trans-enoyl-CoA reductases (ter) tested in strains expressing pct, bktB, and phaB, six combinations show activity for 4-methyl-valerate production. The C. necator phaJ4b and T. denticola ter pair (M3Sc-TdCn) gave the highest 4-methyl-valerate titer.
FIG. 4B shows the indicated titers produced by M3Sc-TdC, compared to a construct expressing C. acetobutylicum hbd and crt (M3Sc-Ca) instead of $phaJ4b_{Cn}$ and $ter_{Td}$. While hbd and crt have previously been used for production of the straight-chain acids butyrate and valerate, no 4-methyl-valerate was detected previously.

Enzymes of the *Clostridium acetobutylicum* butanol pathway and enzymes from polyhydroxyalkanoate pathways have previously been used to synthesize straight chain butanol and pentanol (Bond-Watts 2011; Tseng 2012; Martin 2013). It was previously appreciated that the bktB$_{Cn}$/phaB$_{Cn}$ combination is capable of synthesizing 3-hydroxy-4-methylvaleryl-CoA from isobutyryl-CoA and acetyl-CoA (Martin 2013). At the time of this application, 3-hydroxy-acyl-CoA dehydratases and trans-enoyl reductases with activity on the subsequent branched intermediates have not been identified. An assay was developed to screen for enzymes with the desired activity by isolating Modules 2 and 3 of the synthetic pathway in vivo with different combinations of dehydratases and reductases. LB medium was supplemented with isobutyrate (10 mM) and glucose (1%), and active gene combinations were identified by detecting 4-methyl-valerate secretion. From enzymes documented to have activity on straight medium-chain CoA substrates, 4 phaJ and 6 ter homologs were selected (Table 1). The propionyl-CoA transferase from *Megasphera elsdenii*, pct$_{Me}$, was used to activate isobutyrate (Taguchi 2008). Of the 24 combinations tested, phaJ4 homologs from *Pseudomonas syringae*, *Pseudomonas aeruginosa*, and *C. necator* in combination with ter homologs from *Vibrio parahaemolyticus* and *T. denticola* produced 4-methyl-valerate (FIG. 4A) in these non-limiting embodiments. The high producer, *C. necator* phaJ4b$_{Cn}$/*T. denticola* ter$_{Td}$ (Strain M3Sc-TdCn), yielded 297±45 mg/L 4-methyl-valerate and was selected for Module 3 in future experiments. The dehydratase hbd$_{Ca}$ and reductase crt$_{Ca}$ from the *Clostridium acetobutylicum* butanol pathway were substituted in place of phaB$_{Cn}$ and phaJ4b$_{Cn}$ (Strain M3Sc-Ca) to confirm the involvement of the *C. necator* genes in branched acid production (FIG. 4B). While some butyrate was produced by Strain M3Sc-Ca, 4-methyl-valerate was not detected.

Identification of Branched Medium-Chain Specific Acid and Aldehyde Reductases (Module 4).

Adoption of a CoA-dependent synthesis route involved identification of pathways to link a saturated CoA thioester to the final alcohol product. The CoA thioester could be reduced by either a CoA-dependent aldehyde dehydrogenase or thioesterase/carboxylic acid reductase pairing. The resulting aldehyde could then be reduced by an alcohol dehydrogenase to generate the primary alcohol product. The wide array of identified alcohol dehydrogenases created a high probability that an alcohol dehydrogenase could be found for conversion to the final alcohol (Atsumi 2010; Jornvall 1987; De Smidt 2008). *S. cerevisiae* Adh6p$_{Sc}$ was initially selected because it was previously found to be a broad specificity alcohol dehydrogenase with high activity on medium- and branched-chain aliphatic aldehydes (Larroy 2002).

Candidate reductases for the conversion of 4-methyl-valerate to 4-methyl-1-pentanol were identified from the literature. From these previously identified enzymes, candidates with the potential to selectively convert 4MV to 4-methyl-valeraldehyde were explored. Recently a carboxylic acid reductase (Car) from *Mycobacterium marinum* was shown to convert a range of straight-chain fatty acids to fatty aldehydes, but with increasing catalytic activity ($k_{cat}/K_M$) for longer chain lengths (Car 2012). A previously studied homolog, Car from *N. iowensis*, was first thought to be an aryl acid reductase, but its activity on a range of aliphatic acids was not examined (Venkitasubramanian 2007). A carboxylic acid reductase with specificity for medium-chain branched acids was desired and Car$_{Ni}$ from *N. iowensis* was selected for further study to determine if it had specificity for targeted medium-chain branched acids. The aldehyde produced from an acid reductase can be further reduced by an alcohol dehydrogenase. A wide array of natural alcohol dehydrogenases have been identified, including a number in *E. coli* and many in yeast species (Atsumi 2010). *S. cerevisiae* ADH6$_{Sc}$ was previously found to be a broad specificity alcohol dehydrogenase with high activity on medium- and branched-chain aliphatic aldehydes and lower activity on shorter substrates (Larroy 2002). ADH6$_{Sc}$ was selected to complete Module 4 to enhance preferential reduction of branched medium-chain aldehydes.

Figure 5:
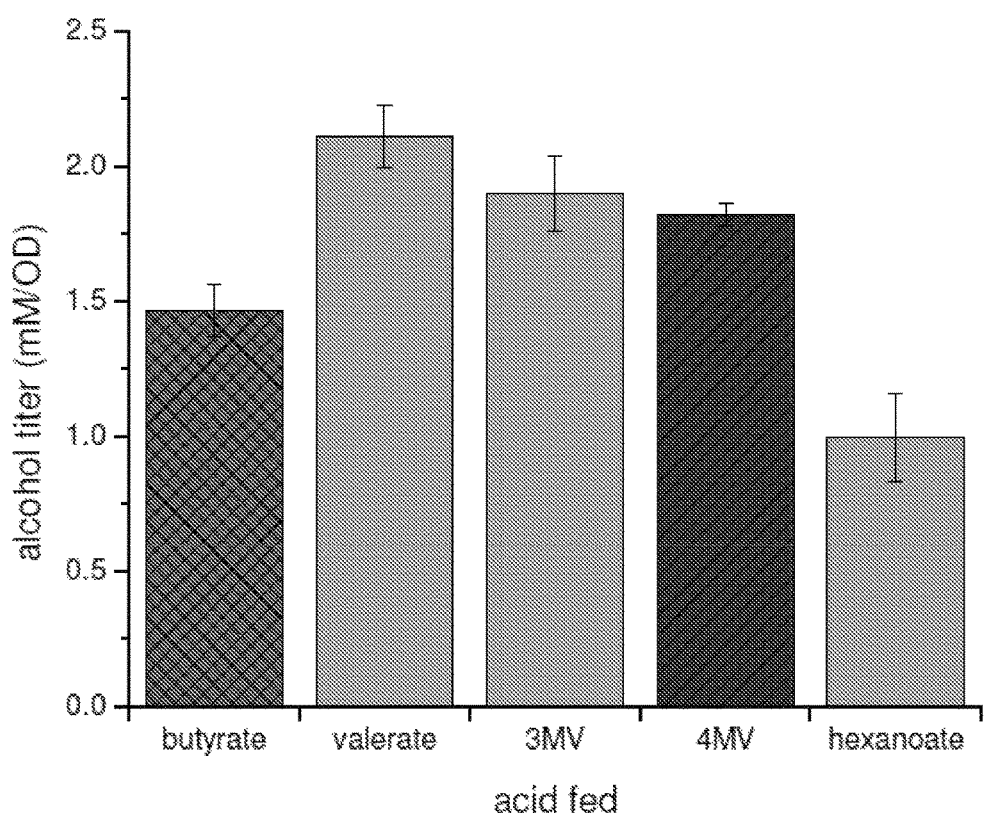
FIG. 5 shows results of an in vivo assay for Carboxylic Acid Reductase selectivity. Cultures of strain M4 expressing car-sfp-ADH6 were supplemented with five different acids at 10 mM initial concentration. Selectivity was determined by measuring normalized titers 5 hours post induction of gene expression. As observed by in vitro analysis, the reduction rate in this embodiment appears to peak at species with a primary carbon chain length of 5 carbons. Transport and toxicity effects of the different acids are not decoupled from enzymatic activity effects in the in vivo assay.

While Car$_{Ni}$ has previously been assayed with a wide range of natural metabolites, its activity on a range of aliphatic acids was not examined. Assays were devised to confirm activity on desired substrates in vitro and in vivo. In the first, N-terminal his-tagged Car$_{Ni}$ was purified and assayed by UV absorption of NADPH with 13 straight and branched acids from C2-C8. Unlike Car from *M. marinum*, Car$_{Ni}$ shows a peak in activity for aliphatic acids with a primary chain-length of 5-6 carbons (FIG. 2A). The medium-chain branched species 4-methyl-valerate and 4-methyl-hexanoate have the highest activity under the non-limiting conditions tested. Preference for 4-methyl-valerate and reduced activity on short-chain acids acetate, isobutyrate, and butyrate made Car$_{Ni}$ a logical selection within the context of the overall pathway. A complementary in vivo assay was designed to examine the effectiveness of the Module 4 pairing. Butyrate, valerate. 3-methyl-valerate, 4-methyl-valerate, and hexanoate were fed to *E. coli* cultures expressing Car$_{Ni}$/ADH6$_{Sc}$ and conversion was monitored by sampling the culture media and liquid chromatography (LC). OD$_{600}$-normalized conversions followed a trend similar to observed in vitro results with maximal conversion for substrates with C5 primary chain length (FIG. 5).

Strong specificity of Car$_{Ni}$ for 4-methyl-valerate over isobutyrate was desired because isobutyrate is produced as an upstream intermediate. The Michaels-Menton kinetics parameters of Car$_{Ni}$ were found with the pathway intermediates isobutyrate and 4-methyl-valerate (FIG. 2B). The k$_{cat}$/K$_m$ ratio with 4-methyl-valerate was found to be 450 times higher than with isobutyrate, quantifying CarNi's the preference of Car$_{Ni}$ for 4-methyl-valerate. With a K$_m$ of 78±9 mM with isobutyrate, Car$_{Ni}$ was expected to convert isobutyrate poorly under physiologically relevant concentrations, which limits shunting of the precursor to isobutaldehyde and isobutanol.

With Module 4 in vivo activity confirmed and in vitro data supporting the choice of Car$_{Ni}$, 4-methyl-1-pentanol production from glucose and isobutyrate was tested with a strain expressing Module 2, 3, and 4 genes (M2P34). As predicted by observed activities for Car$_{Ni}$ and ADH6Sc even while feeding 10 mM (870 mg/L) isobutyrate. Strain M2P34 preferentially produced 4-methyl-1-pentanol (272±7 mg/L) over isobutanol (111±7 mg/L) and butanol (142±9 mg/L) (FIG. 2C).

Demonstration of Modules 3 and 4 Medium-Chain Selectivity for Pentanol Synthesis.

Figure 6:
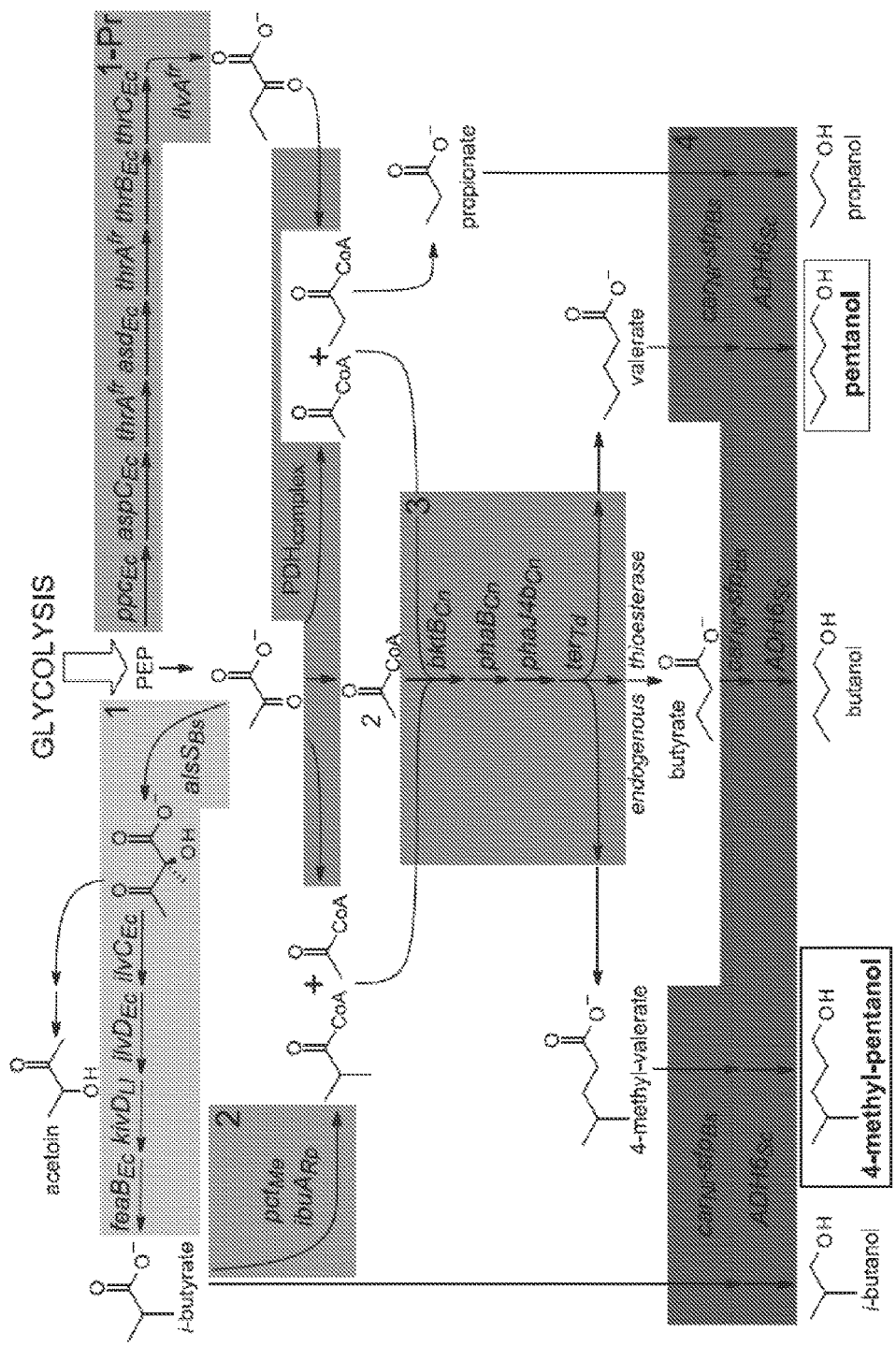
FIG. 6 schematically depicts the 4-methyl-1-pentanol and pentanol pathways. The pentanol pathway shown to the right includes an alternate Module 1 (1-Pr) which converts phosphoenolpyruvate to α-ketobutyrate via threonine biosynthesis. The native E. coli pyruvate dehydrogenase complex (PDH) can be used to convert α-ketobutyrate to propionyl-CoA. A previously implemented pentanol pathway (Tseng, 2012) utilized the aldehydealcohol dehydrogenase AdhE to convert valeryl-CoA to pentanol. AdhE could also act on propionyl-CoA diverting precursor flux to propanol. In some embodiments, Module 4, described herein, has no direct activity on propionyl-CoA and low activity on free propionate.

An analogous CoA-dependent pathway has been developed for production of pentanol (Tseng 2012). The design of the pentanol pathway utilized threonine biosynthesis intermediates to generate propionyl-CoA and relied on the flexibility of many of the natural *Clostridium acetobutylicum* butanol pathway enzymes to accept five carbon intermediates. The alternative Modules 3 and 4 described herein can also be used for pentanol synthesis and they may provide improved preference for medium chain pentanol over the shorter pentanol and butanol products observed when using butanol pathway enzymes (FIG. 6).

Figure 7A:
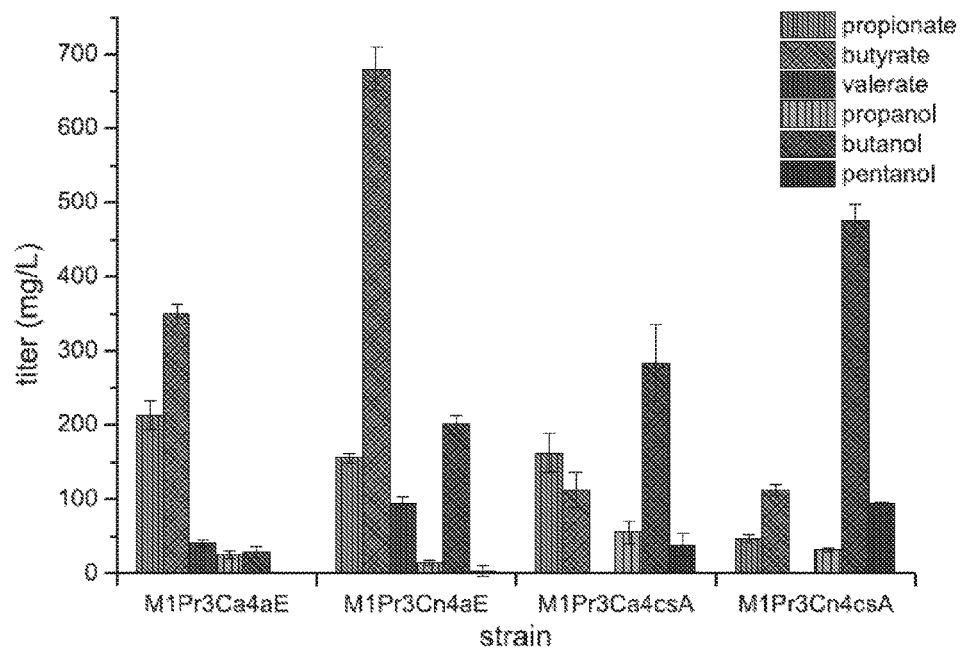
FIG. 7A and FIG. 7B demonstrate the selectivity of Modules 3 and 4 for medium-chain pentanol. Four strains are compared for pentanol production. All four strains overexpress a portion of the threonine pathway, as outlined in Module 1-Pr in FIG. 6. Different Module 3 and 4 enzyme combinations can be used. M1Pr3Ca4aE substitutes the C. acetobutylicum dehydrogenase $hbd_{Ca}$ and dehydratase $crt_{Ca}$ in Module 3 with a codon optimized C. acetobutylicum $adhE_{Ca}$ in place of Module 4 described herein. M1Pr3Cn4aE uses $phaBc_{Cn}$ and phaJ4bCn in Module 3, but also uses C. acetobutylicum adhECa for Module 4. M1Pr3Ca4csA uses $hbd_{Ca}$ and $crt_{Ca}$ while using a standard $car_{Ni}$-$sfp_{Bs}$-$ADH6_{Sc}$ Module 4. Strain M1Pr3Cn4csA uses the standard pathway shown in FIG. 6 with $phaB_{Cn}$-$phaJ4b_{Cn}$ and $car_{Ni}$-$sfp_{Bs}$-$ADH6_{Sc}$.

Four strains were constructed for pentanol production using either Module 3 enzyme pairs phaB$_{Cn}$/phaJ4b$_{Cn}$ or previously used hbd$_{Ca}$/crt$_{Ca}$ and either Module 4 enzymes car$_{Ni}$-sfp$_{Bs}$/ADH6$_{Sc}$, or previously used adhE$_{Ca}$ (Table 2). Cultures were grown in LB supplemented with either 1.2% m/v glucose or 1.2% v/v glycerol. All strains expressing adhE$_{Ca}$ (M1Pr3Cn4aE, M1Pr3Ca4aE) produce significantly reduced butanol titers and no detectable pentanol under the conditions tested (FIG. 7A). It is likely that adhE$_{Ca}$ has limited activity under the more aerobic conditions used in the current work and may also be limited by lower NADH concentrations.

Figure 7B:
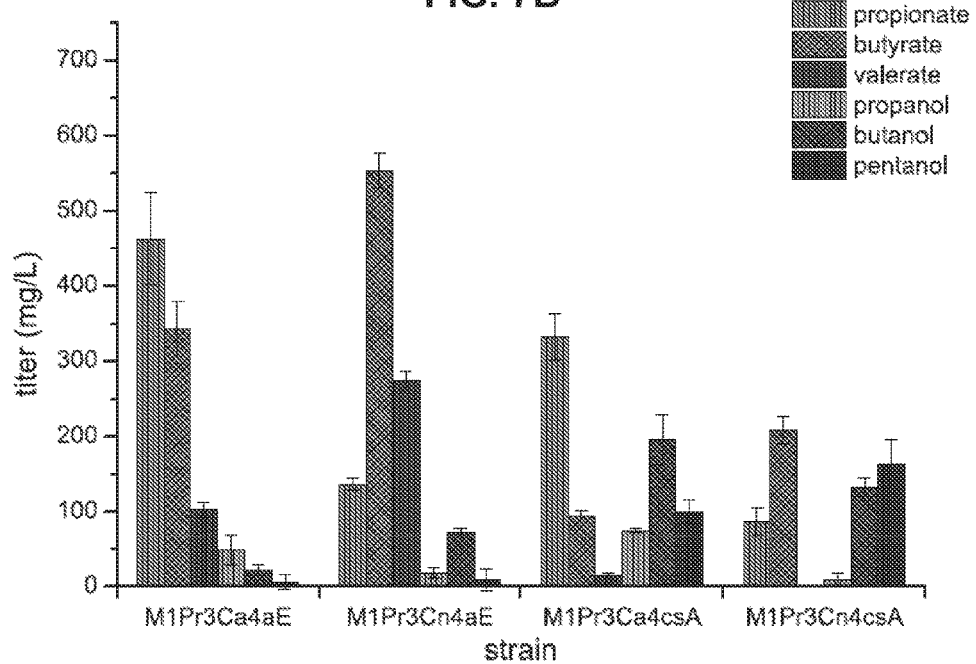

When car$_{Ni}$-sfp$_{Bs}$-ADH6$_{Sc}$ was used for Module 4, the phaB$_{Cn}$/phaJ4b$_{Cn}$ pairing (Strain M1Pr3Cn4csA) produced 163% (163±32 mg/L) of the pentanol produced by the hbd$_{Ca}$/crt$_{Ca}$ pairing (Strain M1Pr3Ca4csA, 100±16 mg/L) with glycerol supplementation. Strain M1Pr3Cn4csA also showed superior selectivity with a pentanol:butanol ratio of 1.2:1, 2.4 times higher than the ratio from Strain M1Pr3Ca4csA. Pentanol production from glucose was also higher for Strain M1Pr3Cn4csA (95±2 mg/L) than Strain M1Pr3Ca4csA (39±14 mg/L), but selectivity was reduced relative to production from glycerol, presumably due to reduced flux to the propionyl-CoA precursor relative to acetyl-CoA (FIG. 7). In some embodiments, the best strain from the previous *C. acetobutylicum*-derived pathway produced a maximum of 116±14 mg/L pentanol with pentanol:butanol and pentanol:propanol ratios below 1:1 even with additional host engineering and the use of microaerobic culture conditions (Tseng 2012). Together these results highlight the ability of the PhaJ4b dehydratase and Car$_{Ni}$ acid reductase to aid in synthesis of medium-chain alcohols. Incorporation of a Pathway to Isobutyryl-CoA (Modules 1 & 2).

Combining isobutyrate synthesis with CoA activation supplies the isobutyryl-CoA precursor for 4-methyl-1-pentanol synthesis from glucose or other simple carbon sources. Previously, Zhang et al. synthesized isobutyrate in *E. coli* by combining valine biosynthesis with the *L lactis* kivD decarboxylase and various native aldehyde dehydrogenases, including PuuC and FeaB (Zhang 2011). The *M. elsdenii* transferase Pct had been previously utilized for CoA activation of carboxylic acids including isobutyrate (Martin 2013). The ATP-dependent isobutyryl-CoA ligase (IbuA$_{Rp}$) from *R. palustris* provided an alternative activation mechanism for Module 2, which creates a redox neutral overall pathway (Crosby 2012).

Figure 8:
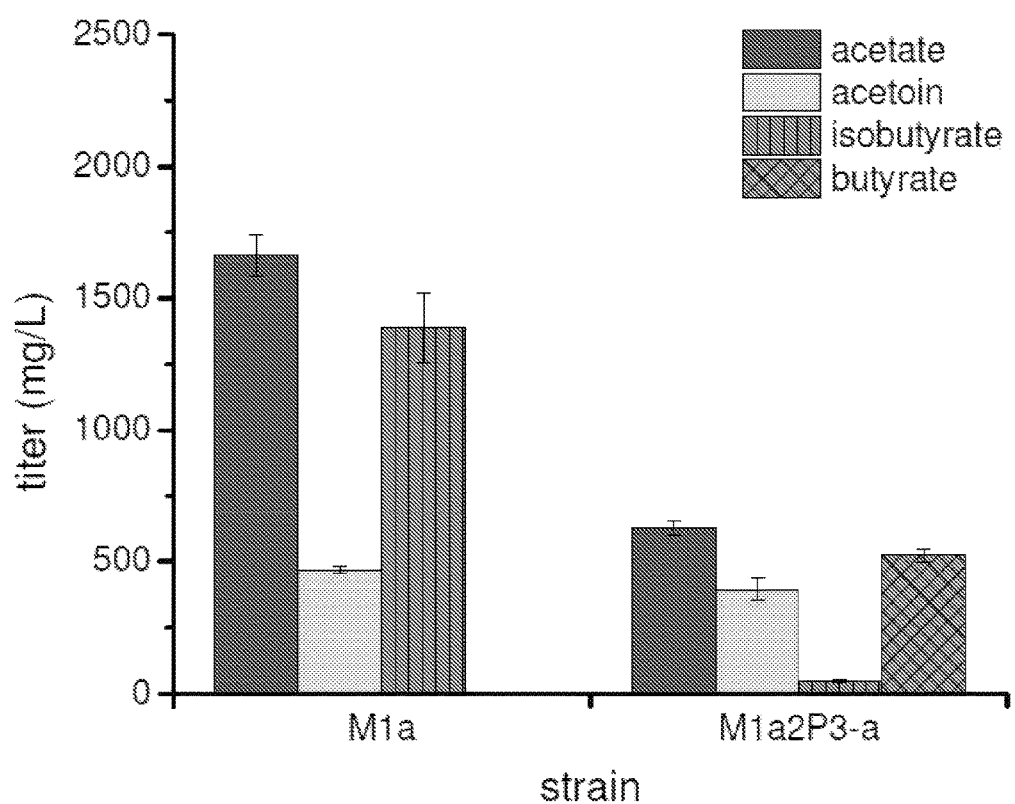
FIG. 8 depicts the observed limitation in some embodiments of the minimal Module 1 pathway to isobutyrate. 48 hour titers of isobutyrate with only $alsS_{Bs}$ and $ilvCD_{Ec}$ expressed (Strain M1a) exceed 1 g/L, but when expressed with Modules 2P and 3 no 4-methyl-valerate and very little isobutyrate is observed. Butyrate production confirms functional Module 3 expression.
Figure 9:
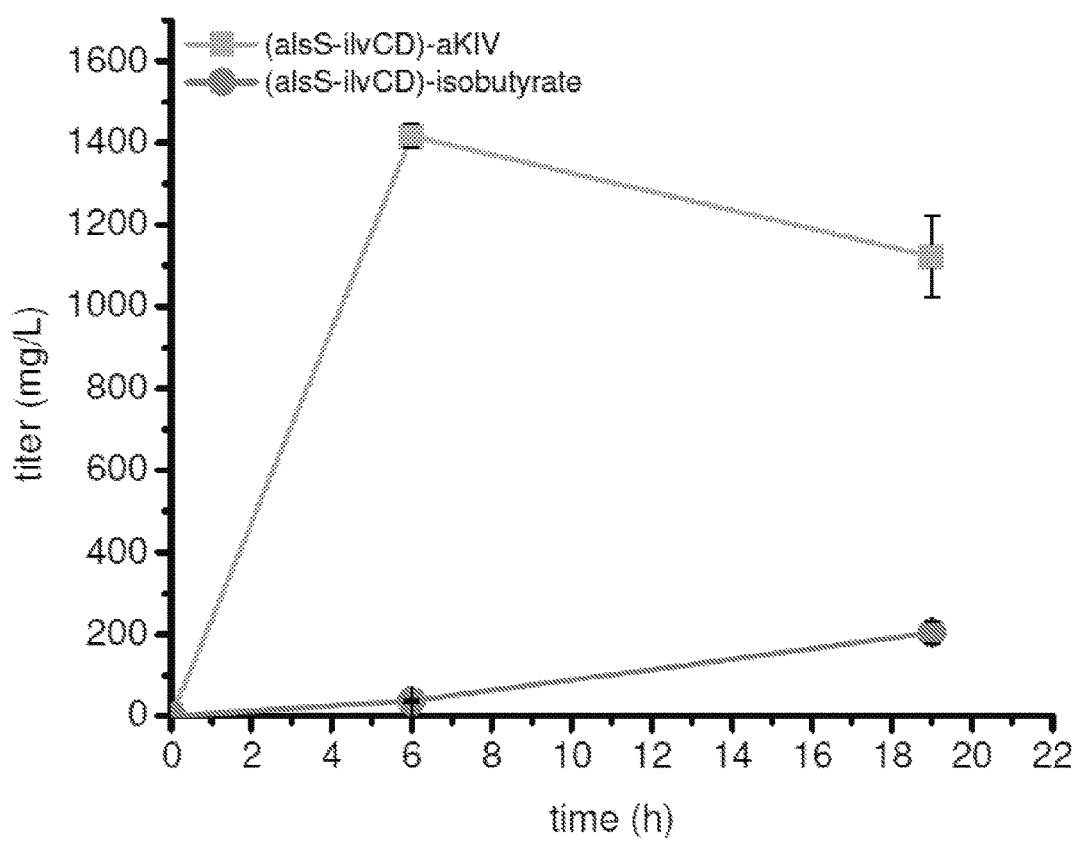
FIG. 9 shows the kinetic limitation in some embodiments of AlsSBs α-KIV decarboxylase activity. Reliance of α-KIV decarboxylase activity of B. subtilis AlsS causes a buildup of α-KIV before slow conversion to isobutyrate.
Figure 10:
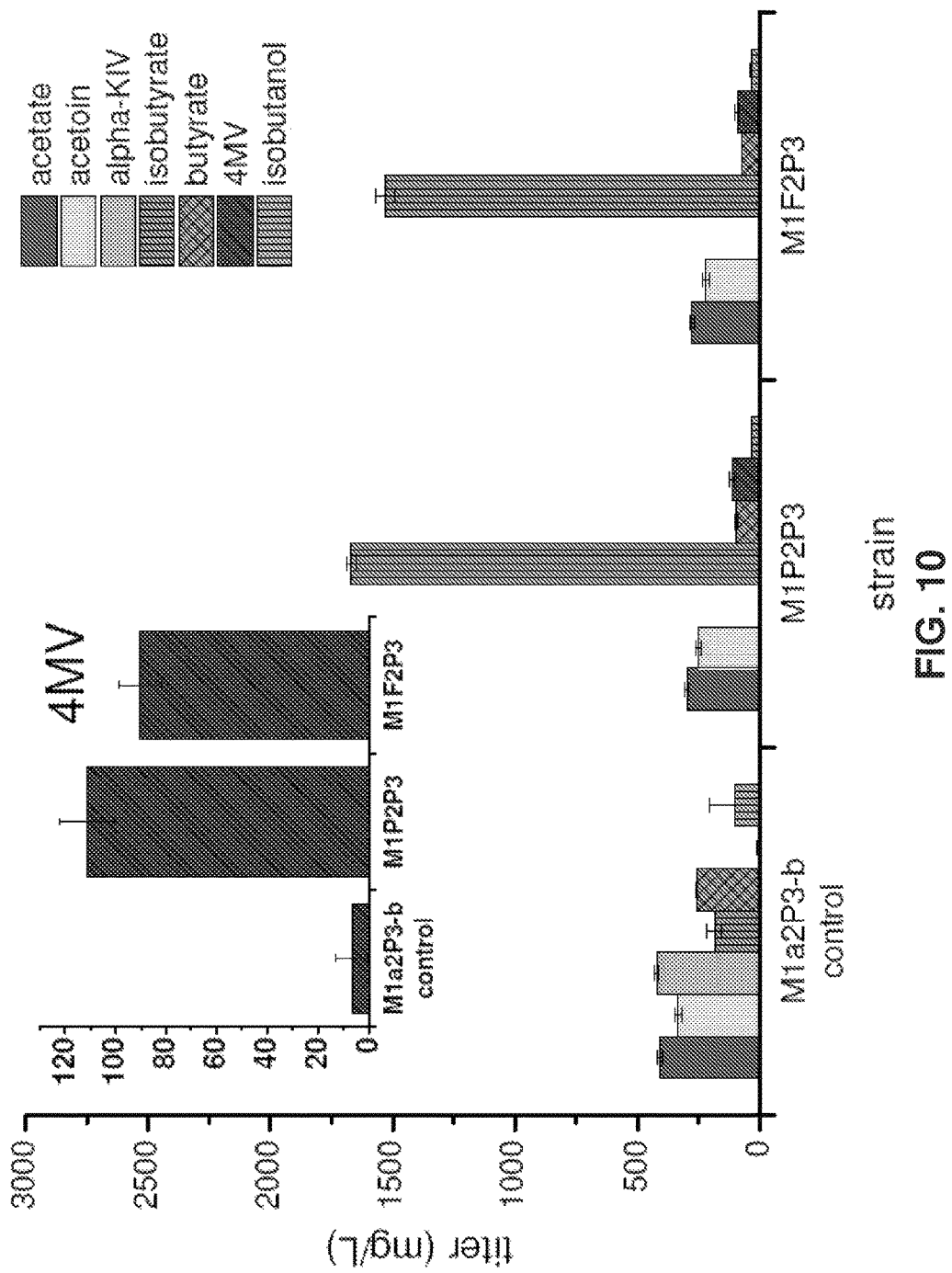
FIG. 10 shows an increasing isobutyrate flux resulting from the use of a dedicated αKIV decarboxylase and isobutyraldehyde dehydrogenase. Addition of αKIV decarboxylase kivDL1, and aldehyde dehydrogenases $puuC_{Ec}$ and $feaB_{Ec}$. (Strains M1P2P3 and M1F2P3) increases isobutyrate and 4-methyl-valerate titers to 1.5 g/L and 100 mg/L, respectively.

Multiple module combinations were used to explore the activities of the two *E. coli* aldehyde dehydrogenases selected for the final oxidation of isobuturaldehyde to isobutyrate. While Zhang et al. utilized the decarboxylase KivD, Atsumi et al. described a secondary ability of *B. subtilis* AlsS to decarboxylate α-KIV. Efforts to streamline Module 1 by expressing only alsS, ilvC, and ilvD revealed that AlsS decarboxylase and native aldehyde dehydrogenase activity were sufficient for production of up to 1.39±0.13 g/L isobutyrate (quantified by LC after 48 hours) for a strain overexpressing alsS-ilvCD. When alsS-ilvCD expression was coupled to expression of Module 2 and 3 genes, isobutyrate titers dropped to 48±5 mg/L and no 4-methyl-valerate was observed (FIG. 8). The time profile of intermediates for the alsS-ilvCD strain revealed a buildup of over 1 g/L α-KIV before appreciable isobutyrate was generated late in the culture (FIG. 9). The addition of kivD and either *E. coli* aldehyde dehydrogenase puuC or feaB to Module 1 with expression of Modules 2(pct) and 3, led to production of 4-methyl-valerate from glucose with titers up to 111±11 mg/L with puuC and 90±9 mg/L with feaB (FIG. 10).

Figure 3:
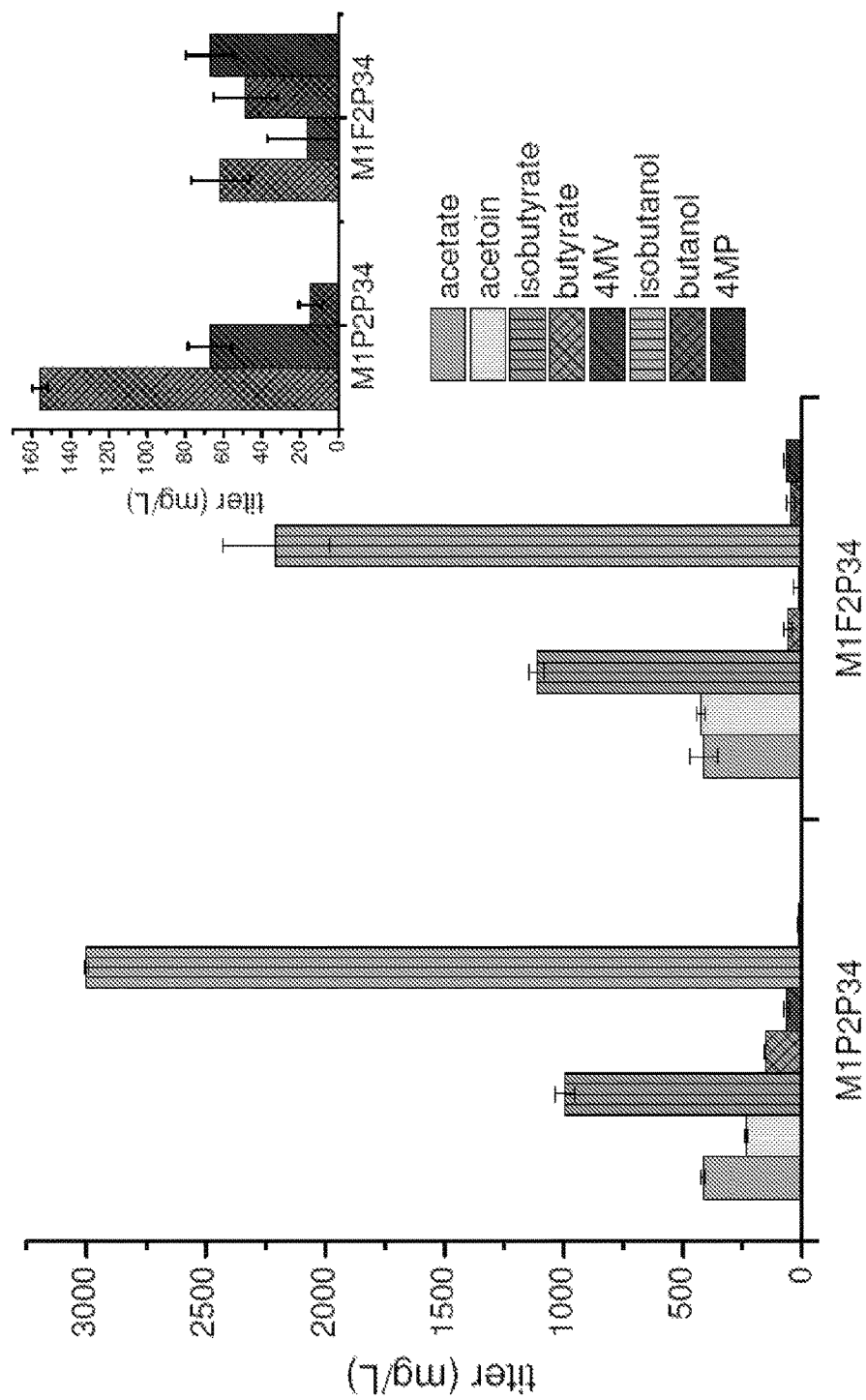
FIG. 3 shows that with the addition of Module 4, it is evident that the aldehyde dehydrogenase PuuC has activity not only on isobutyraldehyde, but also on butyraldehyde and 4-methylvaleraldehyde, preventing formation of the reduced alcohol products. The aldehyde dehydrogenase $FeaB_{Ec}$ appears to have activity on isobutyraldehyde while allowing reduction of butyraldehyde and 4-methyl-valeraldehyde.

Module 1 with puuC led to higher 4-methyl-valerate titers when coupled to Modules 2 and 3, but it was possible that one or both aldehyde dehydrogenases could have activity on the 4-methyl-valeraldehyde intermediate preventing reduction to 4-methyl-1-pentanol when Module 4 was added to give the full pathway from glucose. Both dehydrogenases were used for alternate versions of the full pathway; the feaB-expressing strain (Strain M1F2P34) produced 4-methyl-1-pentanol (67±13 mg/L) while the puuC-expressing strain (Strain M1P2P34) produced 4-methyl-valerate (67-11 mg/L) (FIG. 3A). Additionally the puuC-expressing strain produced more butyrate (156±4 mg/L) and less butanol (15±6 mg/L) than the feaB- expressing strain (62±15 mg/L butyrate, 49±17 mg/L butanol). The overall product profile suggested puuC has activity on medium-chain aldehydes preventing their reduction to alcohols. While 4-methyl-1-pentantol is produced from glucose using the feaB construct, the dominant products are actually isobutyrate (1113±34 mg/L) and isobutanol (2205±225 mg/L) (FIG. 3A), suggesting there were possible bottlenecks in the initial strain M1F2P34. Without Module 4 expression, isobutyrate reached a high titer (1532±40 mg/L) with little isobutanol produced (36±3 mg/L), suggesting that the isobutanol observed with the full pathway came from $Car_{Ni}$ activity on the large isobutyrate pool (FIG. 10, FIG. 3A).

Figure 24A:
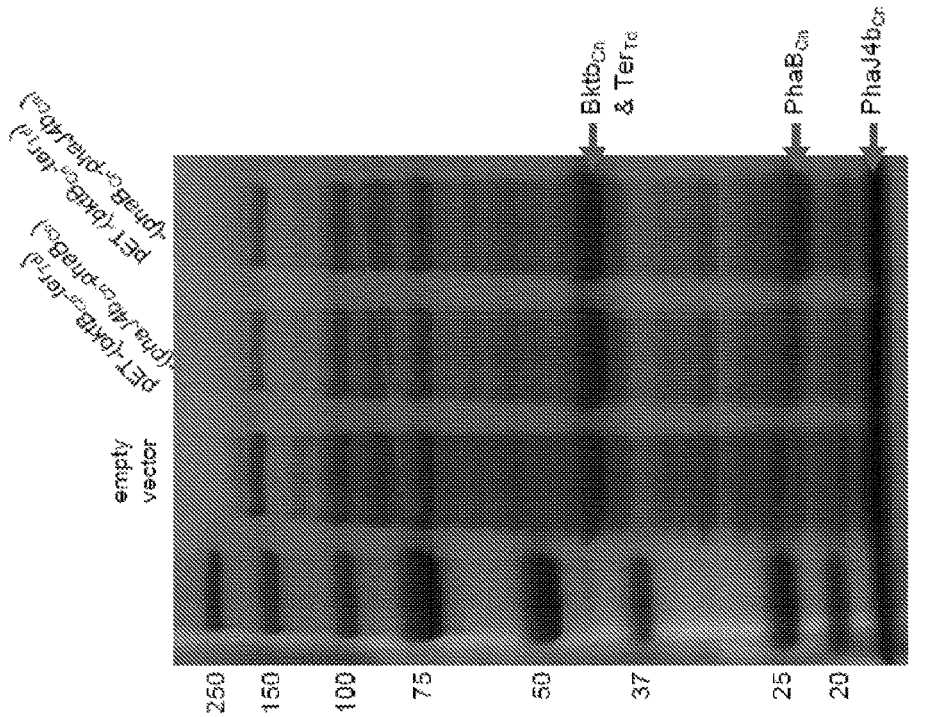
FIG. 24A shows results from strains containing various plasmid constructs that were made for expression of Module 3 genes with Module 2P (pct$_{Me}$) to help improve expression of potential rate limiting enzymes. Cultures were fed 1% glucose and 10 mM isobutyrate and product titers were measured at 48 hours. The initial two-plasmid construct used in screening phaJ and ter homologs, M3Sc-TdCn, contained pET-ter$_{Td}$-(bktB$_{Cn}$-pct$_{Me}$) and pCDF-(phaJ4b$_{Cn}$-phaB$_{Cn}$). M3Sc-TdCn produced 257±33 mg/L of 4MV and 208±14 mg/L butyrate. The Module 3 genes were re-cloned in operons in plasmid pET-(bktB$_{Cn}$-ter$_{Td}$)-(phaJ4b$_{Cn}$-phaB$_{Cn}$) to be used in constructs expressing the full 4-methyl-1-pentanol pathway. Strain M2P3a was constructed by transforming MG1655(DE3) endA recA with pET-(bktB$_{Cn}$-ter$_{Td}$)-(phaJ4b$_{Cn}$-phaB$_{Cn}$) and pCDF-pct$_{Me}$. The 4-methyl-valerate and butyrate titers of M2P3a were 61% and 97% of those observed for M3Sc-TdCn, respectively. By simply swapping the order of phaJ4b$_{Cn}$ and phaB$_{Cn}$ in their synthetic operon to make pET-(bktB$_{Cn}$- ter$_{Td}$)-(phaB$_{Cn}$-phaJ4b$_{Cn}$) in Strain M2P3b the 4-methyl-valerate titer increases to 120% of the level observed in Strain M3Sc-TdCn.

New plasmid constructs were made to reorganize genes onto plasmids by module (Tables 4 and 6). It was anticipated that operon construction could reduce enzyme expression, especially for genes in the second position, but it was unknown if the effect would be detrimental to overall production without knowledge of the rate limiting enzyme (Lim 2011). Two Module 3 plasmid variants were tested to explore whether $PhaB_{Re}$ activity could become limiting when expressed from an operon used in the new constructs (FIG. 24A). The variant with $phaB_{Re}$ in the first position of a two gene operon generated higher titers, supporting the theory that $phaB_{Re}$ could be the limiting activity within Module 3. Comparison of $phaB_{Cn}$ expression from the two operon variants by SDS-PAGE confirmed higher $phaB_{Cn}$ expression when placed in the first position (FIG. 24B). Additionally, operon variants for $alsS_{Bs}$ and $ilvC_{Ec}$ expression were tested to examine if better balancing of flux between Module 1 and the native acetyl-CoA pathway could improve 4MP production (FIG. 24A). Placing $alsS_{Bs}$ in the second position while using the new plasmid constructs (Strain M1F(IA)2I34) increased 4 methyl-pentanol titers (168±31 mg/L) while reducing isobutyrate (290±24 mg/L) and isobutanol (1046±45 mg/L) titers.

Figure 18A:
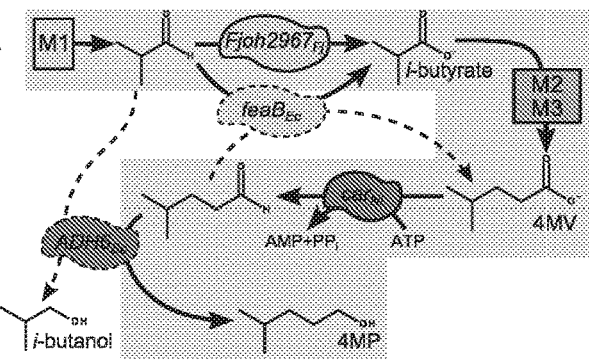
FIG. 18A depicts key reactions involving aldehydes can generate futile cycles (aldehyde dehydrogenase feaB$_{Ec}$ with the carboxylic acid reductase car$_{Ni}$) or byproduct shunts (alcohol dehydrogenase ADH6$_{Sc}$). The desired pathway route is shown in bold arrows within the shaded box. Undesired reactions are shown with dashed arrows. Enzymes with insufficient selectivity have dashed outlines.
Figure 18B:
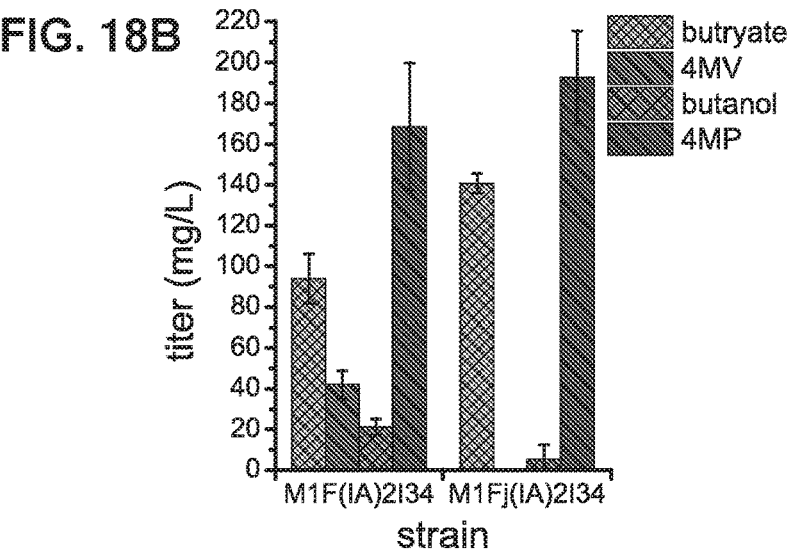
FIG. 18B shows that when feaB$_{Ec}$ (Strain M1F(IA)2I34) was replaced with the isobutyraldehyde specific aldehyde dehydrogenase Fjoh2967$_{Fj}$ in Strain M1Fj(IA)2I34 4-methyl-valerate titers were reduced and 4-methyl-1-pentanol titers were increased.
Figure 18C:
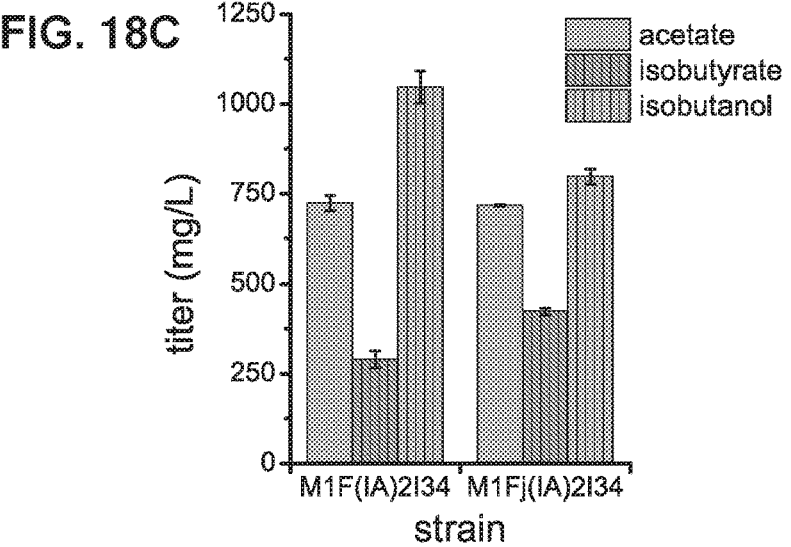
FIG. 18C shows that Strain M1Fj(IA)2I34 (Fjoh2967$_{Fj}$) produced lower isobutanol and higher isobutyrate titers relative to strain M1F(IA)2I34 (feaB$_{Ec}$).
Figure 24C:
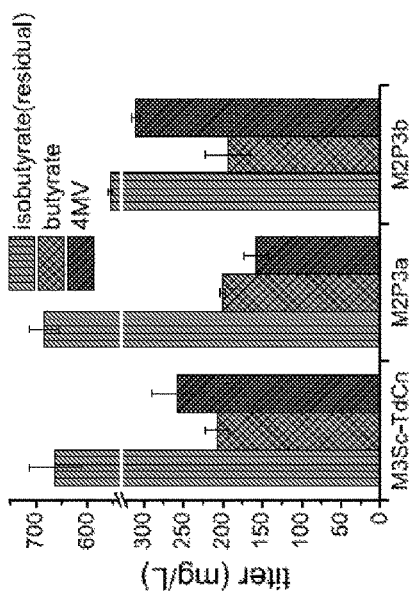
FIG. 24C presents results from an effort to balance flux between acetyl-CoA and isobutyryl-CoA. New constructs were made containing the full pathway using feaB$_{Ec}$ and the isobutyryl-CoA synthetase ibuA$_{Rp}$. Strains M1F(AI)2I34 and M1F(IA)2I34 expressed the first Module 1 gene, alsS$_{Bs}$, in either the first or second position of a two gene operon, respectively. The expected lower alsS$_{Bs}$ expression in Strain M1F(IA)2I34 led to decreases in isobutyrate and isobutanol byproducts and increased 4-methyl-1-pentanol.
Figure 24B:
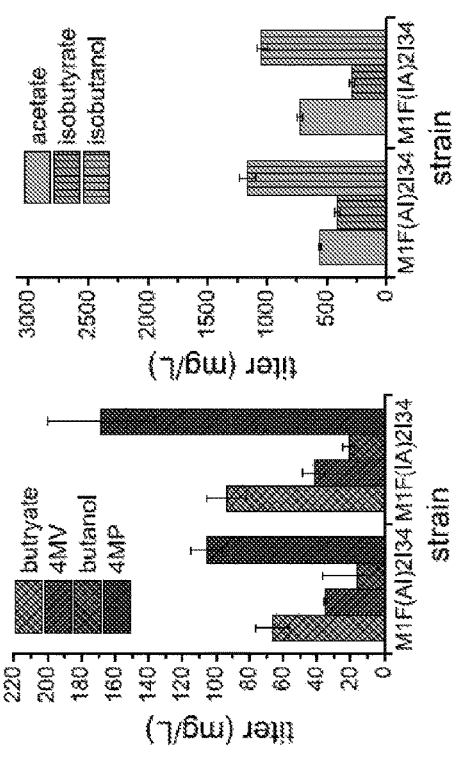
FIG. 24B shows increased phaB$_{Cn}$ expression from the phaB$_{Cn}$-phaJ4b$_{Cn}$ operon as confirmed by expression of pET-(bktB$_{Cn}$-ter$_{Td}$)-(phaJ4b$_{Cn}$-phaB$_{Cn}$) and pET-(bktB$_{Cn}$-ter$_{Td}$)-(phaB$_{Cn}$-phaJ4b$_{Cn}$) plasmids in the production strain MG1655(DE3) endA recA. Lysate from the construct expressing pET-(bktB$_{Cn}$-ter$_{Td}$)-(phaB$_{Cn}$-phaJ4b$_{Cn}$) contains a significantly higher PhaB$_{Cn}$ concentration when visualized by SDS-PAGE. Molecular weights of the Module 3 proteins are: BktB$_{Cn}$, 42.5 KD, Ter$_{Td}$, 43.8 KD, PhaB$_{Cn}$, 26.4 KD, and PhaJ4b$_{Cn}$, 16.9 KD.

Based on available in vitro data and the presence of 4 methyl-valerate (42±7 mg/L) even for improved Strain M1F(IA)2I34, it was possible that $FeaB_{Ec}$ could be oxidizing 4-methyl-valeraldehyde into 4 methyl-pentanol creating a futile cycle with $Car_{Ni}$ (FIG. 18A, FIG. 24C). An aldehyde dehydrogenase, Fjoh2967Fj from *Flavobacterium johnsonaie* had been found to prefer an isobutyraldehyde substrate over other aldehyde substrates when tested in vitro (Yamanaka 2002). Replacing $feaB_{Ec}$ with $Fjoh2967_{Fj}$ in Strain M1Fj(IA)2I34 led to increased 4 methyl-pentanol (193±23 mg/L, 0.033±0.005 mol/mol glucose) and elimination of detectable 4-methyl-valerate (FIG. 18B). Isobutyrate titers (424±9 mg/L, 0.084±0.004 mol/mol glucose) were increased and isobutanol titers (797±7 mg/L, 0.187±0.006 mol/mol glucose) were reduced (FIG. 18C).

Figure 25:
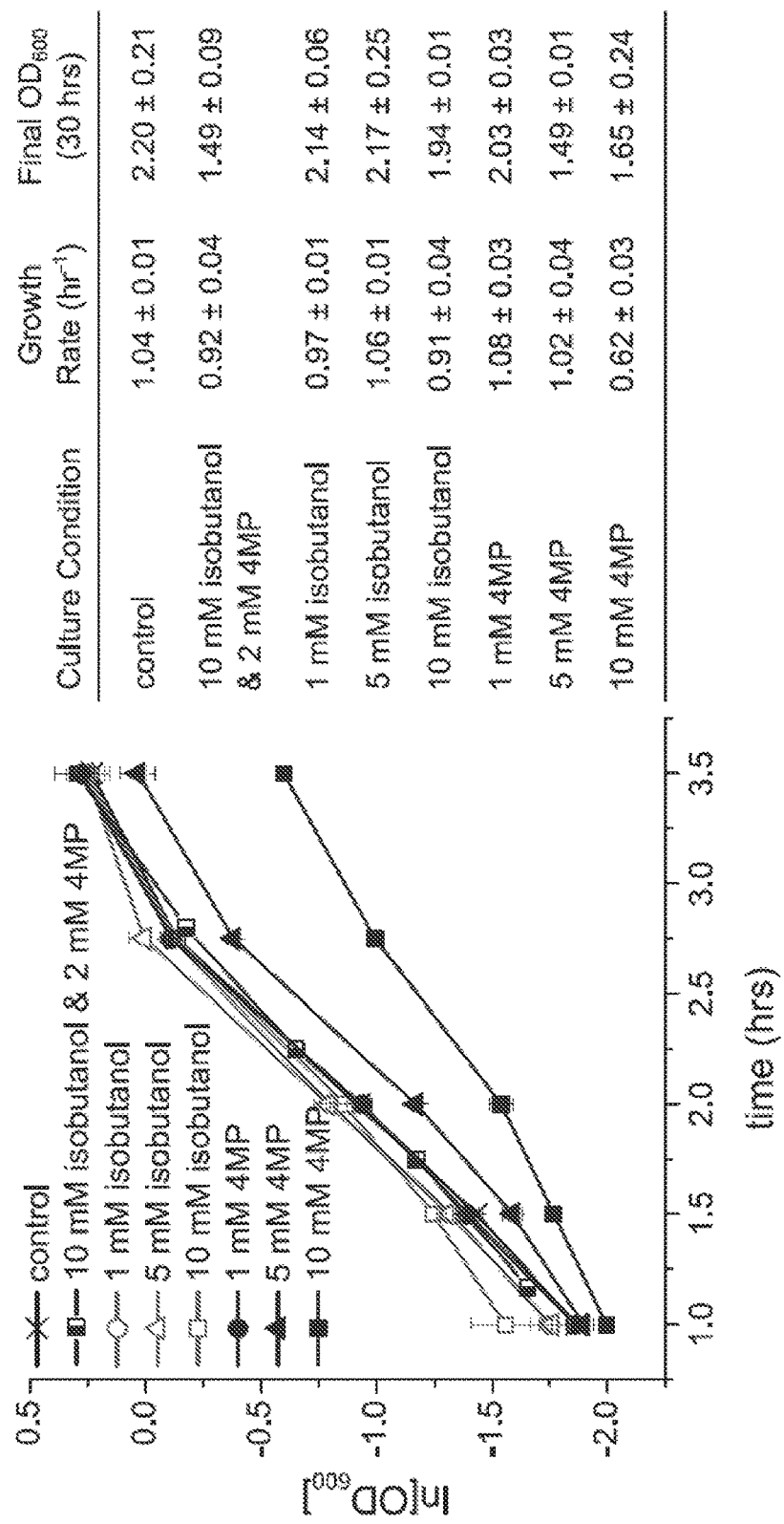
FIG. 25 shows the relative toxicity of isobutanol and 4-methyl-1-pentanol on MG1655(DE3) endA recA. MG1655(DE3) endA recA was cultured in an LB medium with 1.2% glucose and varying concentrations of isobutanol or 4-methyl-1-pentanol (1 mM (74 mg/L), 5 mM (370 mg/L), or 10 mM (741 mg/L) isobutanol or 1 mM (102 mg/L), 5 mM (511 mg/L), or 10 mM (1022 mg/L) 4-methyl-1-pentanol). The exponential growth rate was unchanged by 4-methyl-1-pentanol concentrations exceeding those observed in final titers (193±23 mg/L) for the high producing Strain M1Fj(IA)2I34. The highest 4-methyl-1-pentanol concentration (10 mM, 1022 mg/L) did lead to a reduction in growth rate of 40%. The highest concentration of isobutanol, 10 mM (741 mg/L), led to a reduction in the growth rate of 10%. While 4-methyl-1-pentanol is more toxic than isobutanol at equimolar concentrations, it is also significantly more hydrophobic. The solubility of 4-methyl-1-pentanol in water (7.4 g/L) is an order of magnitude below that of isobutanol (70 g/L)[6]. If higher titers of 4-methyl-1-pentanol are achieved, in situ gas stripping or simple phase separation could potentially be used to extract 4-methyl-1-pentanol from the culture medium (Lee 1994).

In order to examine if alcohol toxicity could be limiting product titers, toxicities of the dominant byproduct isobutanol and desired product 4-methyl-pentanol were assayed through exogenous addition of alcohols to the growth medium at concentrations from 1-10 mM. Isobutanol and 4MP concentrations up to 5 mM did not inhibit the exponential growth rate (FIG. 25). A combination of 10 mM (741 mg/L) isobutanol and 2 mM (204 mg/L) 4 methyl-pentanol (comparable to titers observed for Strain M1Fj(IA)2I34) only reduced the exponential growth rate by 10%, the same reduction observed with 10 mM isobutanol alone. While endogenously produced alcohols may be involved in alternative toxicity mechanisms, this result suggests that current titers are likely not limited by product toxicity.

Balancing Upstream Pathway Flux.

Based on results from expressing the full pathway (FIG. 3A), Strain M1F2P34 (Table 3) was modified to improve the balance of flux between the Module 1 and endogenous PDH branches of the pathway (FIG. 1). The modified design was based on the hypothesis that lower alsS expression, the first committed step in Module 1, reduces flux to isobutyrate and increases the acetyl-CoA:isobutyryl-CoA ratio. Strains M1(AI)2P34 and M1(IA)2P34 have reorganized operon constructions moving Module 3 genes onto pETDuet-1 and creating two variant operons for expression of the Module 1 genes $alsS_{Bs}$ and $ilvC_{Ec}$ on pCDFDuet-1 (Table 3). The first variant in Strain M1(AI)2P34 maintained the $alsS_{Bs}$-$ilvC_{Ec}$ gene order used in Strain M1F2P24. The second variant, used in Strain M1(IA)2P34, also aimed to reduce $alsS_{Bs}$ expression by switching the order to $ilvC_{Ec}$-$alsS_{Bs}$. A second set of strains, M1(AI)2I34 and M1(IA)2I34, were constructed using the ATP-dependent isobutyryl-CoA ligase, $ibuA_{Rp}$, in place of $pct_{Me}$ in order to decouple isobutyrate activation from the acetyl-CoA pool (Table 3). The constructs with $alsS_{Bs}$ in the second position. M1(IA)2P34 and M1(IA)2I34, produced more 4-methyl-1-pentanol, 103±13 mg/L and 115±26 mg/L respectively (FIG. 11A). 4-methyl-1-pentanol titers were improved by a factor of 1.7 over Strain M1F2P34. Isobutyrate and isobutanol titers were reduced by a factor of 0.35 and 0.13 for Strain M1(IA)2I34 and 0.12 and 0.29 for Strain M1(IA)2P34 respectively. Interestingly, Strain M1(AI)2I34 (with $alsS_{Bs}$ in the first position) produced more acetate and less isobutyrate and isobutanol than Strain M1(IA)2I34.

Figure 11A:
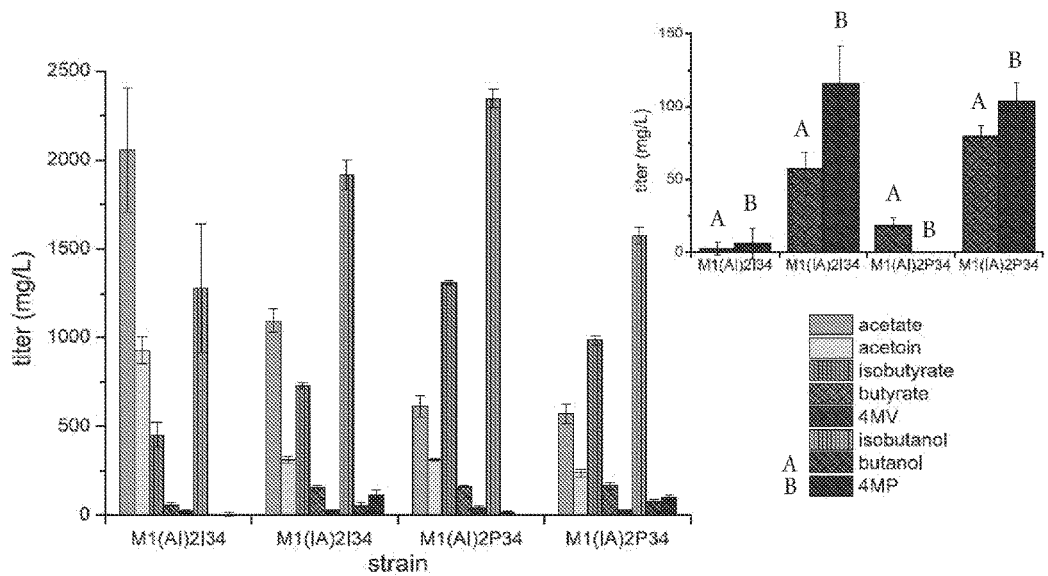
FIG. 11A shows that due to reduced expression in some embodiments by genes in the second position of two-gene polycistronic operons, the genes alsS$_{Bs}$ and ilvC$_{Ec}$ were cloned in both operon permutations and paired with both Module 2 activators pct$_{Me}$ and ibuA$_{Rp}$. Comparison of Strains M1(AI)2P34 and M1(IA) 2P24 reveals the expected trend of reduced isobutyrate and isobutanol titers and increased 4-methyl-1-pentanol production when alsS$_{Bs}$ is in the second position (Strain M1(IA) 2P34). Strains with the ATP-dependent activator ibuA$_{Rp}$ do display the expected 4-methly-1-pentanol titer increase with alsS$_{Bs}$ in the second position, but isobutyrate and isobutanol titers are also higher. It is possible that ATP depletion under conditions of high isobutyrate flux leads to reduced final titers.
Figure 11B:
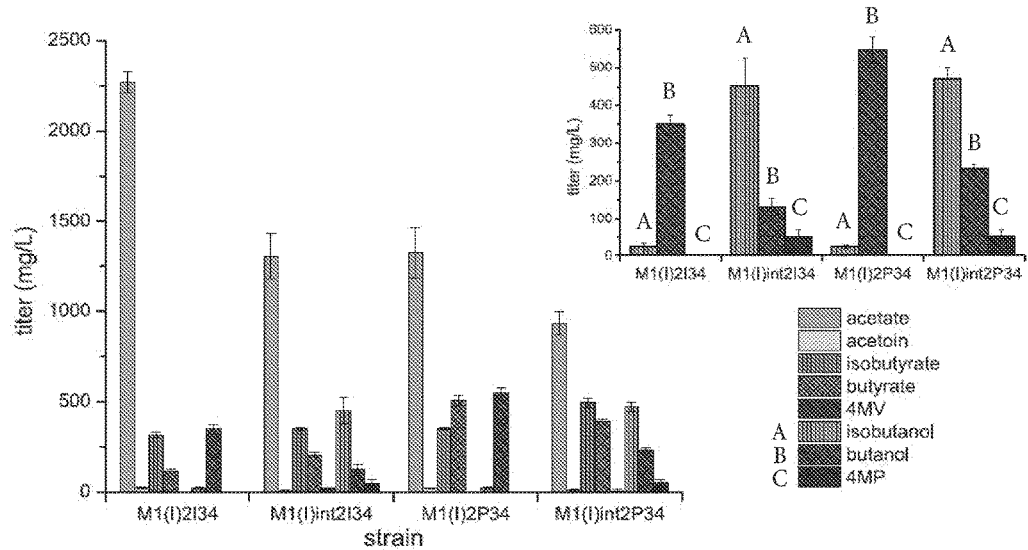
FIG. 11B shows that to further reduce flux to isobutyrate and isobutanol alsS$_{Bs}$ was integrated into the genome of MG1655(DE3) endA recA. Complementary plasmids containing only ilvC$_{Ec}$, ilvD$_{Ec}$, and one of the two Module 2 activators pct or ibuA were cloned. Strains M1(I)2I34 and M1(I)2P34, which do not express alsS$_{Bs}$, produce butyrate and butanol with a low level of isobutyrate as expected. The endogenous valine biosynthesis pathway is still capable of producing αKIV which is decarboxylated by kivD$_{Ll}$ in these strains. 4-methyl-valerate and 4-methyl-1-pentanol were not observed, presumably due to low flux to isobutyrate. When the same plasmid constructs were put in the MG1655(DE3) endA recA lacZYA::tetR-P$_{tet}$-alsS$_{Bs}$ background (Strains M1(I)int2I34 and M1(I)int2P24) isobutyrate and isobutanol were produced with reduced butanol and small 4-methyl-1-pentanol titers. In some embodiments, the integrated alsS$_{Bs}$ was necessary for 4-methyl-1-pentanol production and significantly reduced isobutanol byproduct formation from over 1.5 g/L to less than 0.5 g/L.

While Strains M1(IA)2I34 and M1(IA)2P34 favorably altered the product profile, titers of isobutyrate and isobutanol remained high, suggesting further reduction of alsS, may achieve significantly improved 4-methyl-1-pentanol titers. To achieve lower expression a tetR-$P_{tet}$-$alsS_{Bs}$ cassette containing an anhydrotetracycline (aTc) inducible promoter in front of $alsS_{Bs}$ was integrated into the lacZYA locus of MG1655(DE3) endA recA. Complimentary pCDFDuet-1 constructs without $alsS_{Bs}$ were made and transformed with the remaining pathway plasmids in either MG1655(DE3) endA recA for Strains M1(I)2P34 and M1(I)2I34 or MG1655(DE3) endA recA lacZYA::tetR-$P_{tet}$-$alsS_{Bs}$ for Strains M1(I)int2P34 and M1(I)int2I34. At 72 hours, Strains M1(I)2P34 and M1(I)2I34 without $alsS_{Bs}$ expression had produced 351±8 mg/L and 319±18 mg/L isobutyrate respectively. Minimal acetoin and isobutanol were observed (FIG. 11B). Butanol was produced at up to 546±35 mg/L (M1(I) 2P34) without observable 4-methyl-1-pentanol production suggesting some level of $alsS_{Bs}$ expression may be required in some embodiments to generate the desired product. Strains M1(I)int2P34 and M1(I)int2I34 with aTc induction produced close to 0.5 g/L isobutanol but only 53±17 mg/L and 48±22 mg/L of 4-methyl-1-pentanol respectively (FIG. 11B). The product profiles indicated that even with reduced Module 1 flux, carbon-chain extension was still limited.

Improving Module 3 Gene Expression.

Figure 12:
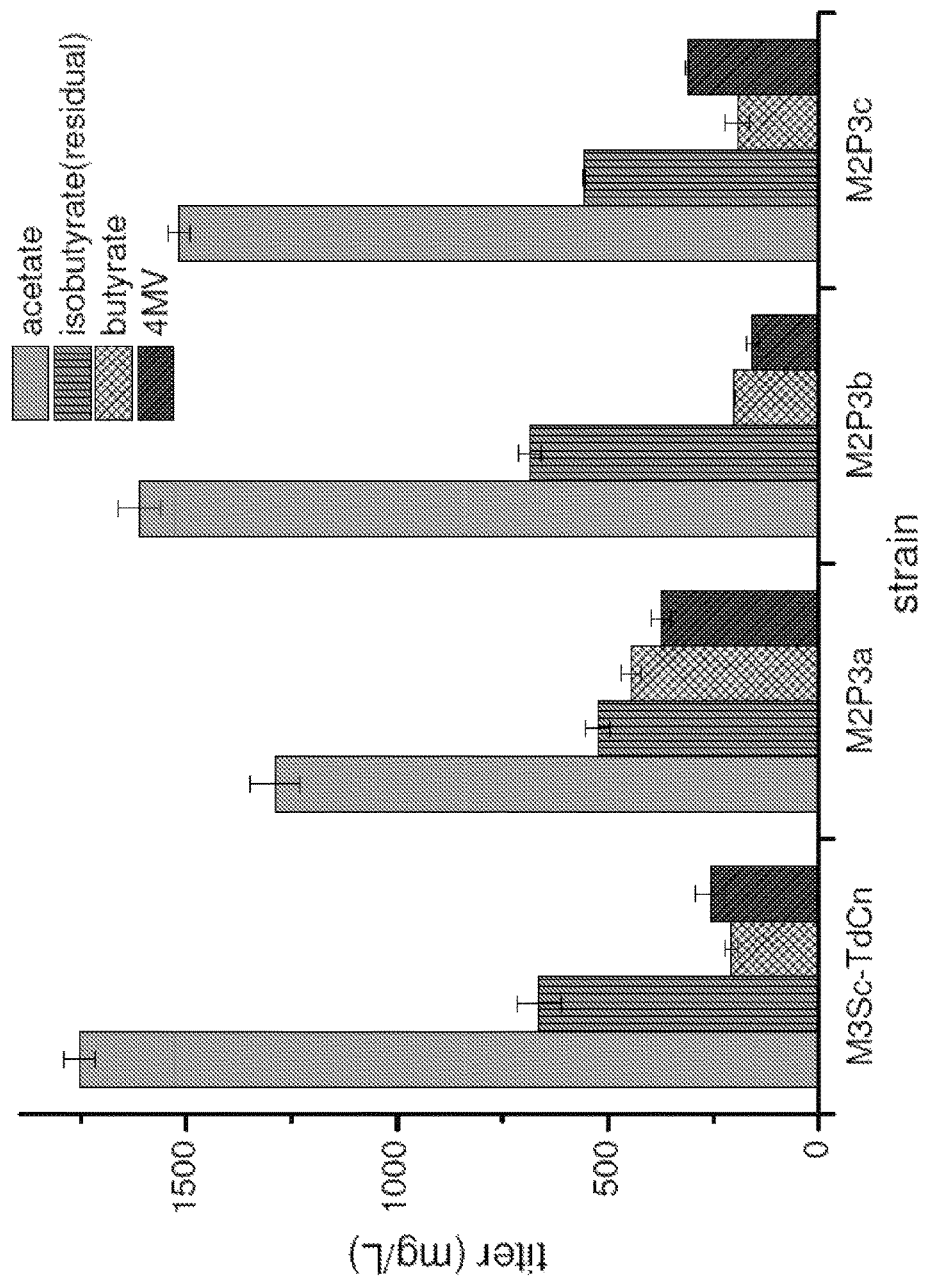
FIG. 12 depicts optimization of Module 3 gene expression through modifying the plasmid construction. Multiple plasmid constructs were made for expression of Module 3 genes with Module 2P (pctMe) to help improve expression of potential rate limiting enzymes. Cultures were supplemented with 1% glucose and 10 mM isobutyrate, and product titers were measured at 48 hours. The initial two plasmid construct used in screening phaJ and ter homologs. M3Sc-TdCn, contained pET-ter$_{Td}$-(bktB$_{Cn}$-pct$_{Me}$) which has both inserts cloned out of frame from the built-in ribosome binding sites (RBSs) and start codons of pETDuet-1. That pETDuet-1 construct was recloned to make pET-(bktB$_{Cn}$-pct$_{Me}$)-ter$_{Td}$ with both inserts in frame with the RBSs and start codons of the plasmid. The new plasmid was used in Strain M2P3a. Strain M2P3a showed a 114% increase in butyrate and 45% increase in 4-methyl-valerate titers over Strain M3Sc-Td$_{Cn}$ indicating reduced expression of at least one key enzyme in Strain M3Sc-Td$_{Cn}$. The Module 3 genes were re-cloned in operons in plasmid pET-(bktB$_{Cn}$-ter$_{Td}$)-(phaJ4b$_{Cn}$-phaB$_{Cn}$) to be used in constructs expressing the full 4-methyl-1-pentanol pathway. Strain M2P3b was constructed by transforming MG1655(DE3) endA recA with pET-(bktB$_{Cn}$-ter$_{Td}$)-(phaJ4b$_{Cn}$-phaB$_{Cn}$) and pCDF-pct$_{Me}$. Butyrate and 4-methyl-valerate titers of M2P3b fall to 45% and 42% of those observed for M2P3a, respectively. By swapping the order of phaJ4b$_{Cn}$ and phaB$_{Cn}$ in their synthetic operon to make pET-(bktB$_{Cn}$-ter$_{Td}$)-(phaB$_{Cn}$-phaJ4b$_{Cn}$) in Strain M2P3c, the 4-methyl-valerate titer increased to 83% of the level observed in Strain M2P3a where all Module 3 genes were under control of independent promoters.

One hypothesis for the low flux towards 4-methyl-1-pentanol was a potential rate limiting enzyme(s) from Module 3. The original pET-ter$_{Td}$-(bktB$_{Cn}$-pct$_{Me}$) plasmid used in ter/phaJ screening (Strain M3Sc-Td$_{Cn}$) had both ter$_{Td}$ and the bktB$_{Cn}$-pct$_{Me}$ operon cloned with additional RBSs out of frame with the pETDuet-1 plasmid RBSs and start codons for MCS-1 and MCS-2 (Table 4). The plasmid was recloned utilizing the built-in RBSs and start codons to produced pET-(bktB$_{Cn}$-pct$_{Me}$)-ter$_{Td}$ used in strain M2P34a (Table 3). The recloned plasmid produced 114% more butyrate 444±24 mg/L) and 45% more 4-methyl-valerate (373±24 mg/L) in cultures supplemented with 10 mM isobutyrate and 1% glucose, indicating that improved enzyme expression of Module 3 enzymes can increase flux to 4-methyl-valerate (FIG. 12).

In creating strains with the full 4-methyl-1-pentanol pathway, Module 3 genes were consolidated into operons on pET-(bktB$_{Cn}$-ter$_{Td}$)-(phaJ4b$_{Cn}$-phaB$_{Cn}$) (Table 3). It was anticipated that operon construction could reduce enzyme expression, especially in the second position, but it was unknown how detrimental this reduction would be to Module 3 flux. When Strain M2P34b (pET-(bktB$_{Cn}$-ter$_{Td}$)-(phaJ4b$_{Cn}$-phaB$_{Cn}$) and pCDF-pctMe) was grown under the above conditions it produced 45% of the butyrate and 42% of the 4-methyl-1-pentanol observed with Strain M2P34a (FIG. 12). In order to test if phaB$_{Cn}$ expression became limiting in the Strain M2P34b, a new operon was constructed swapping the order of phaJ4b$_{Cn}$ and phaB$_{Cn}$ which was used in Strain M2P34c. The 4-methyl-valerate titer from Strain M2P34c improved over Strain M2P34b to 83% (310-±5 mg/L) of the 4-methyl-valerate produced by Strain M2P34a. The new pET-(bktB$_{Cn}$-ter$_{Td}$)-(phaJ4b$_{Cn}$-phaB$_{Cn}$) plasmid was selected for Module 3 expression.

Figure 23A:
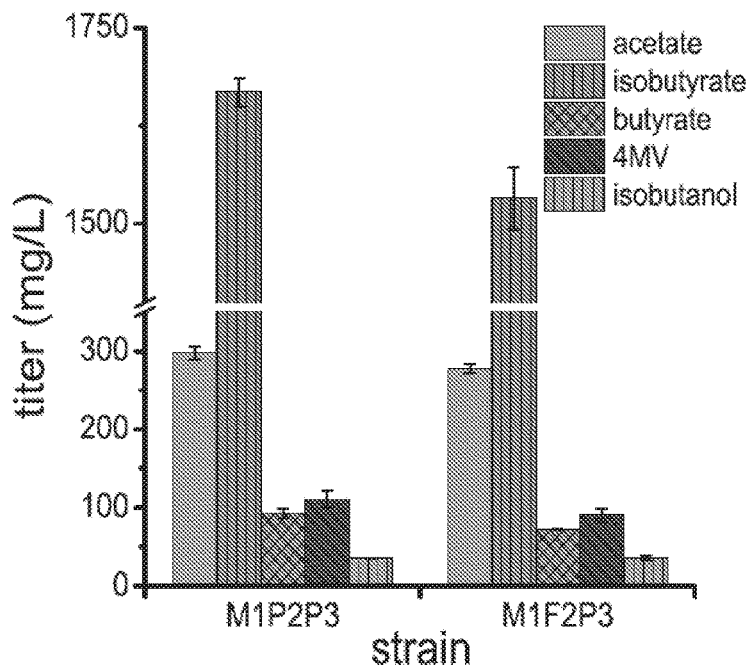
FIG. 23A shows results from combining valine biosynthesis to α-ketoisovalerate (αKIV) with expression of αKIV decarboxylase kivD$_{Ll}$, and aldehyde dehydrogenases puuC$_{Ec}$ and feaB$_{Ec}$ (Strains M1P2P3 and M1F2P3, respectively) produces 1.668±0.018 g/L of isobutyrate and 111±11 mg/L of 4MV (M1P2P3) or 1.532±0.40 g/L of isobutyrate and 90±9 mg/L of 4-methyl-valerate (M1F2P3).
Figure 23B:
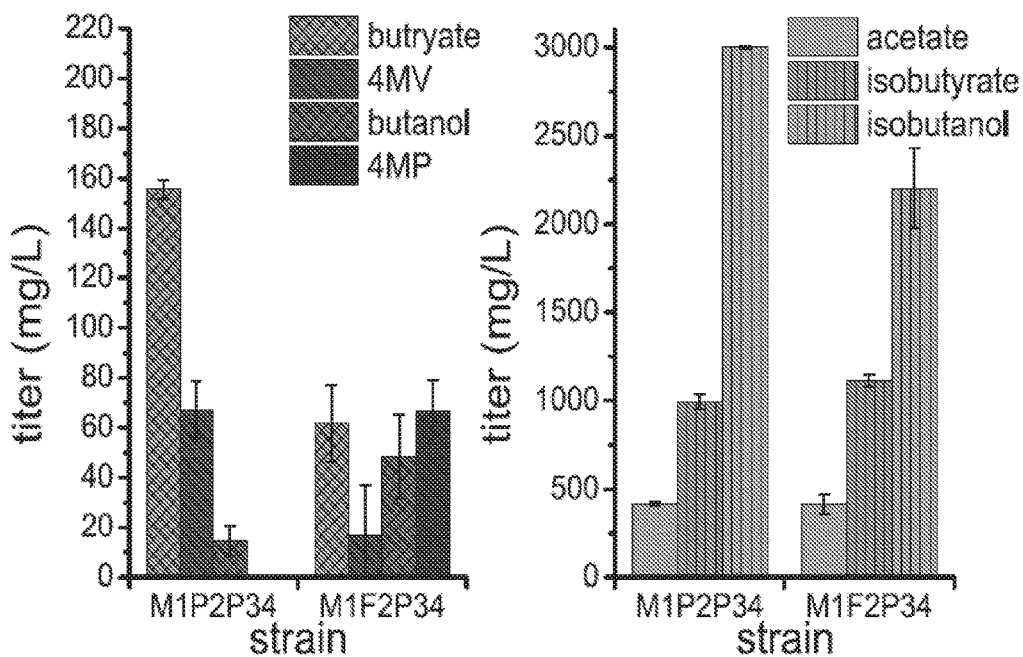
FIG. 23B shows extended acid and alcohol products are produced from initial full pathway strains M1P2P34 (puuC$_{Ec}$) and M1F2P34 (feaB$_{Ec}$) using the pct$_{Me}$ activator showed 4-methyl-1-pentanol production only when the feaB$_{Ec}$ aldehyde dehydrogenase was used. Titers of acetate, isobutyrate, and isobutanol for the same strains show relatively low acetate titers for strains utilizing the transferase activator pct$_{Me}$ with large isobutyrate and isobutanol titers from Module 1 flux overflow.

Three strains with only Modules 2 and 3 expressed in different constructs were compared to examine the effect of the position of the dehydrogenase phaB$_{Cn}$ in the operon. Shake flask cultures were grown with glucose and isobutyrate supplementation. When Strain M2P3a (pET-(bktB$_{Cn}$-ter$_{Td}$)-(phaJ4b$_{Cn}$-phaB$_{Cn}$), pCDF-pct$_{Me}$) was grown under the above conditions, it produced 97% of the butyrate and 61% of the 4-methyl valerate observed with the original Strain M3Sc-TdCn used in phaJ/ter screening (FIG. 23). In an attempt to increase phaB$_{Cn}$ expression over that in Strain M2P34a, a new operon was constructed for Strain M2P34b by swapping the order of phaJ4b$_{Cn}$ and phaB$_{Cn}$. The 4-methyl valerate titer from Strain M2P34b was improved to 120% of that observed for Strain M3Sc-Td$_{Cn}$. Butyrate titers remained equal within error. The new pET-(bktB$_{Cn}$-ter$_{Td}$)-(phaB$_{Cn}$-phaJ4b$_{Cn}$) plasmid was used for Module 3 expression subsequently.

The high isobutyrate and isobutanol titers relative to acetate in Strain M1F2P34 also suggested that flux between the two upstream branches of the pathway may have been unbalanced. Strain M1F2P34 was modified in order to improve the balance of flux between the Module 1 and endogenous PDH branches of the pathway (FIG. 17). The modified design is based on the hypothesis that lower alsS$_{Bs}$ expression, the first committed step in Module 1, reduces flux to isobutyrate and increases the acetyl-CoA:isobutyryl-CoA ratio. Two new strains were constructed which contained one of two pCDFDuet-1 constructs in addition to pACYC-(car$_{Ni}$-sfp$_{Bs}$)-ADH6$_{Sc}$, pCOLA-feaBEc-kivD$_{Ll}$ and pET-(bktB$_{Cn}$-ter$_{Td}$)-(phaB$_{Cn}$-phaJ4b$_{Cn}$) plasmids (Table 4). Both pCDFDuet-1 variants contained an ibuA$_{Rp}$-ilvD$_{Ec}$ operon in one multiple cloning site (MCS). The first variant, containing an alsS$_{Bs}$-ilvC$_{Ec}$ operon in the second MCS, completed Strain M1F(AI)2I34 (Table 6). The second variant, Strain M1F(IA)2I34, contained an ilvC$_{Ec}$-alsS$_{Bs}$ operon designed to reduce alsS$_{Bs}$ expression by putting alsS in the lower expressing second position of the operon. As hypothesized, Strain M1(IA)2I34 produced more 4-methyl-1-pentanol, 168±31 mg/L, than the M1(AI)2I34 variant, 106±10 mg/L (FIG. 18B). Isobutyrate (290±24 mg/L) and isobutanol (1046±45 mg/L) titers were lower for Strain M1F(IA)2I34 than for Strain M1F(AI)2I34 (isobutyrate 417±22 mg/L, isobutanol 1163±71 mg/L).

Identification of Alternative Enzymes for Aldehyde Oxidation and Reduction.

Figure 13:
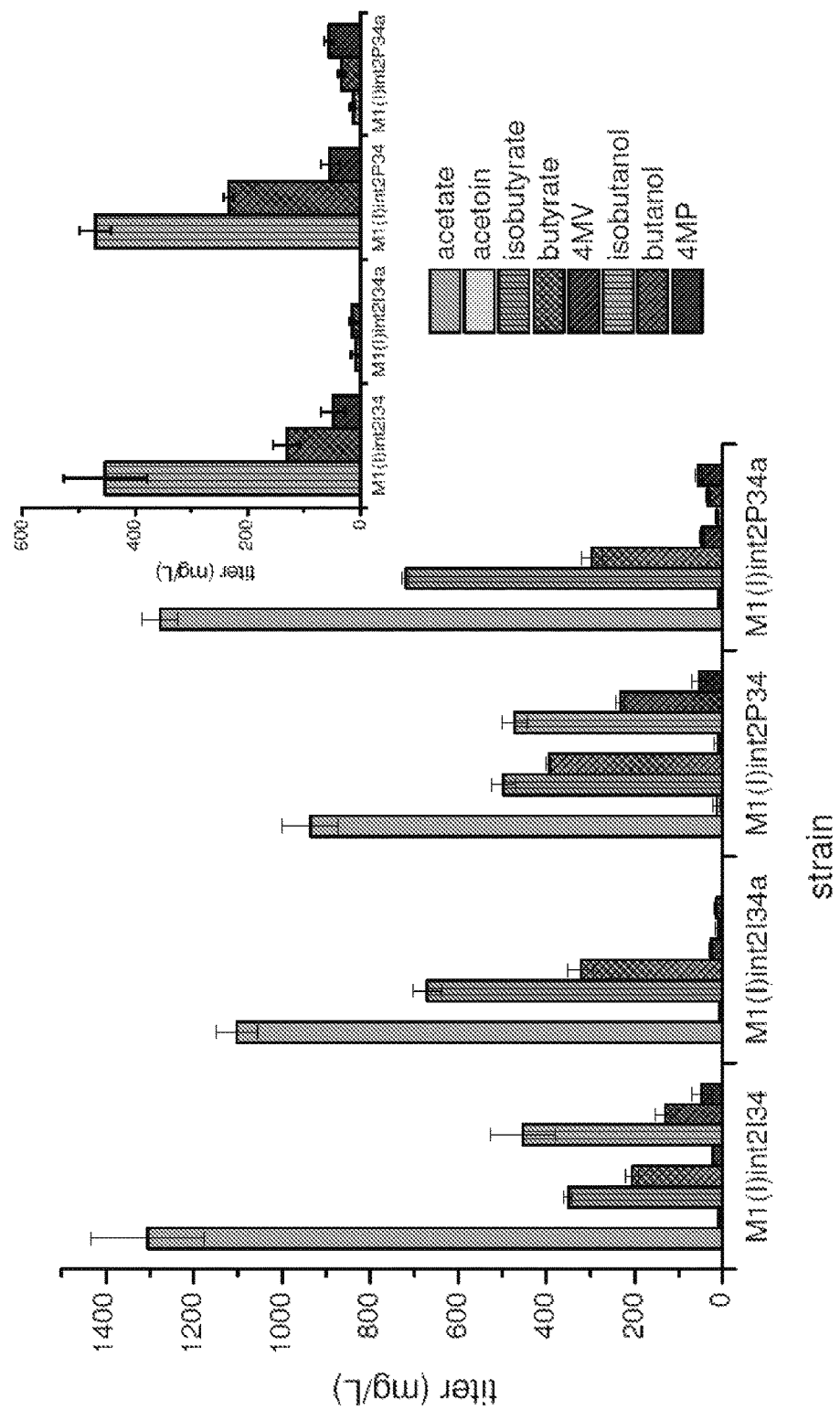
FIG. 13 depicts the product profile dependence in some embodiments on alcohol dehydrogenase ADH6$_{Sc}$. Strains expressing ADH6$_{Sc}$ (M1(I)int2I34 and M1(I)int2P34) and not expressing ADH6$_{Sc}$ (M1(I)int2I34a and M1(I)int2P34a) were compared to explore the ability of endogenous E. coli aldehyde reductase activity to generate the desired 4-methyl-1-pentanol final product. In some embodiments, isobutanol production was found to be dependent on ADH6$_{Sc}$ expression even though in vitro results had revealed a preference for longer chain substrates similar to 4-methylvaleraldehye. The 4-methyl-1-pentanol titer appeared to be independent of ADH6$_{Sc}$ expression when pct$_{Me}$ was used as the isobutyrate activator, but in some embodiments no 4-methyl-1-pentanol was observed without ADH6$_{Sc}$ for strains using ibuA$_{Rp}$.
Figure 14:
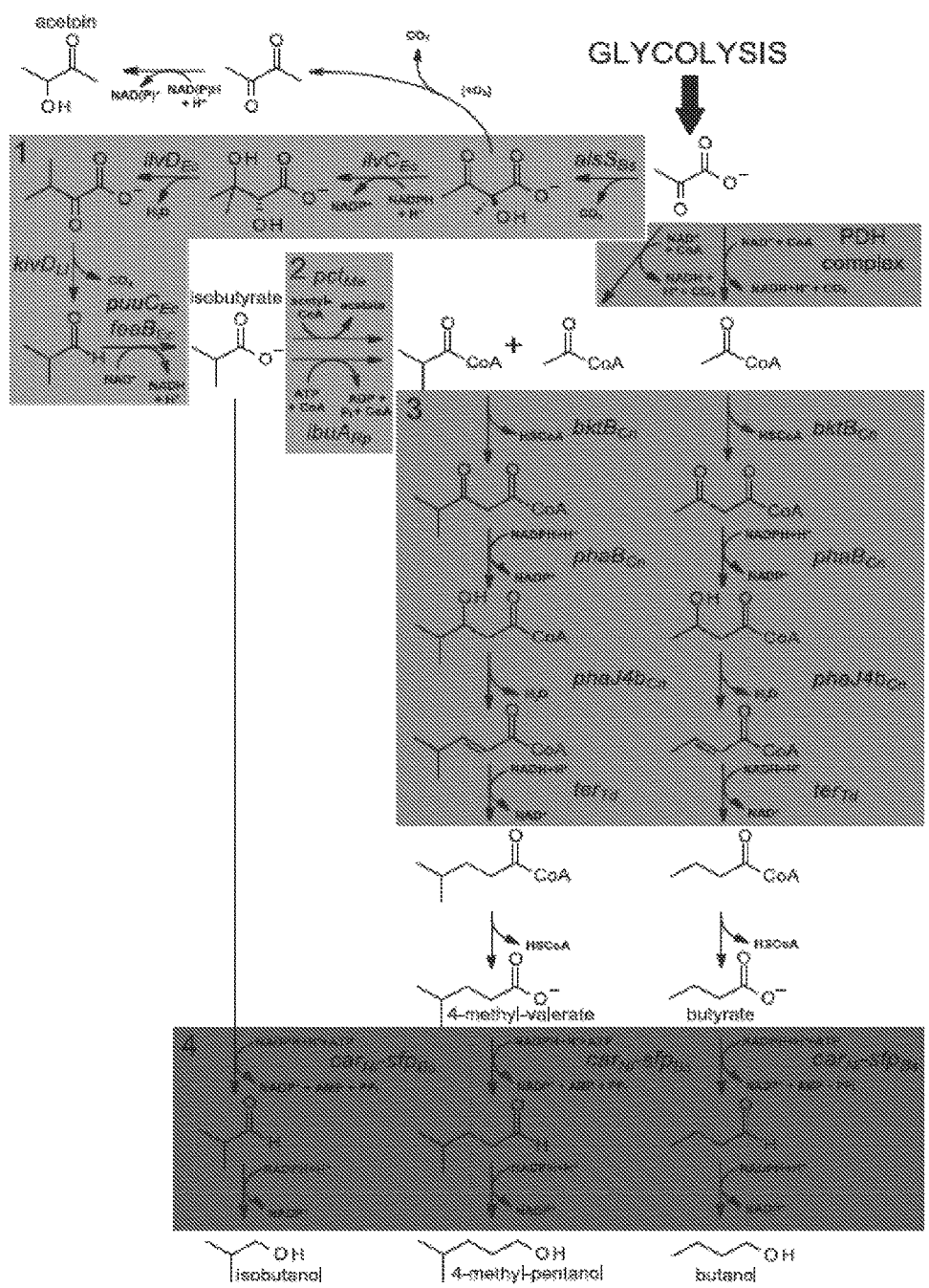
FIG. 14 schematically presents non-limiting embodiments of the modules of the full 4-methyl-1-pentanol pathway described herein. Module 1 ("1") in some embodiments comprises B. subtilis acetolactate synthase alsS$_{Bs}$, Escherichia coli acetohydroxy acid isomeroreductase ilvC$_{Ec}$ and dihydroxy acid dehydratase ilvD$_{Ec}$, Lactococcus lactis α-ketoisovalerate decarboxylase kivD$_{Ll}$, and Escherichia coli aldehyde dehydrogenases puuC$_{Ec}$ or feaB$_{Ec}$. Module 2 ("2") in some embodiments comprises one of two isobutyrate activators Megasphaera elsdenii propionyl-CoA transferase pct$_{Me}$ or Rhodopseudomonas palustris isobutyryl-CoA ligase ibuA$_{Rp}$.

Some embodiments of the pathway design described herein successfully rely on endogenous thioesterase activity to generate free acid for reduction by Car$_{Ni}$. Other work has demonstrated that native E. coli alcohol dehydrogenase activity has been sufficient for production of primary alcohols (Atsumi). Endogenous activity was examined to determine if it could be used without ADH6$_{Sc}$ overexpression to produce 4-methyl-1-pentanol. When 10 mM 4-methyl-valerate was supplied to Strain M4a (expressing only car$_{Ni}$-sfp$_{Bs}$) all 10 mM was converted to 4-methyl-1-pentanol within 14 hours (Table 3). Clearly some endogenous enzyme could reduce 4-methyl-valeraldehyde to 4-methyl-1pentanol. When ADH6$_{Sc}$ was removed from full pathway Strains M1(I)int2P34 and M1(I)int2I34 to create Strains M1(I) int2P34a and M1(I)int2I34a, 4-methyl-1-pentanol titers were reduced and isobutanol byproduct titers dropped to nearly undetectable levels (FIG. 13). This result indicated that an aldehyde reductase may be necessary in some embodiments with the full pathway and that isobutanol production predominantly resulted from reduction of isobutyraldehyde by ADH6$_{Sc}$.

Figure 15:
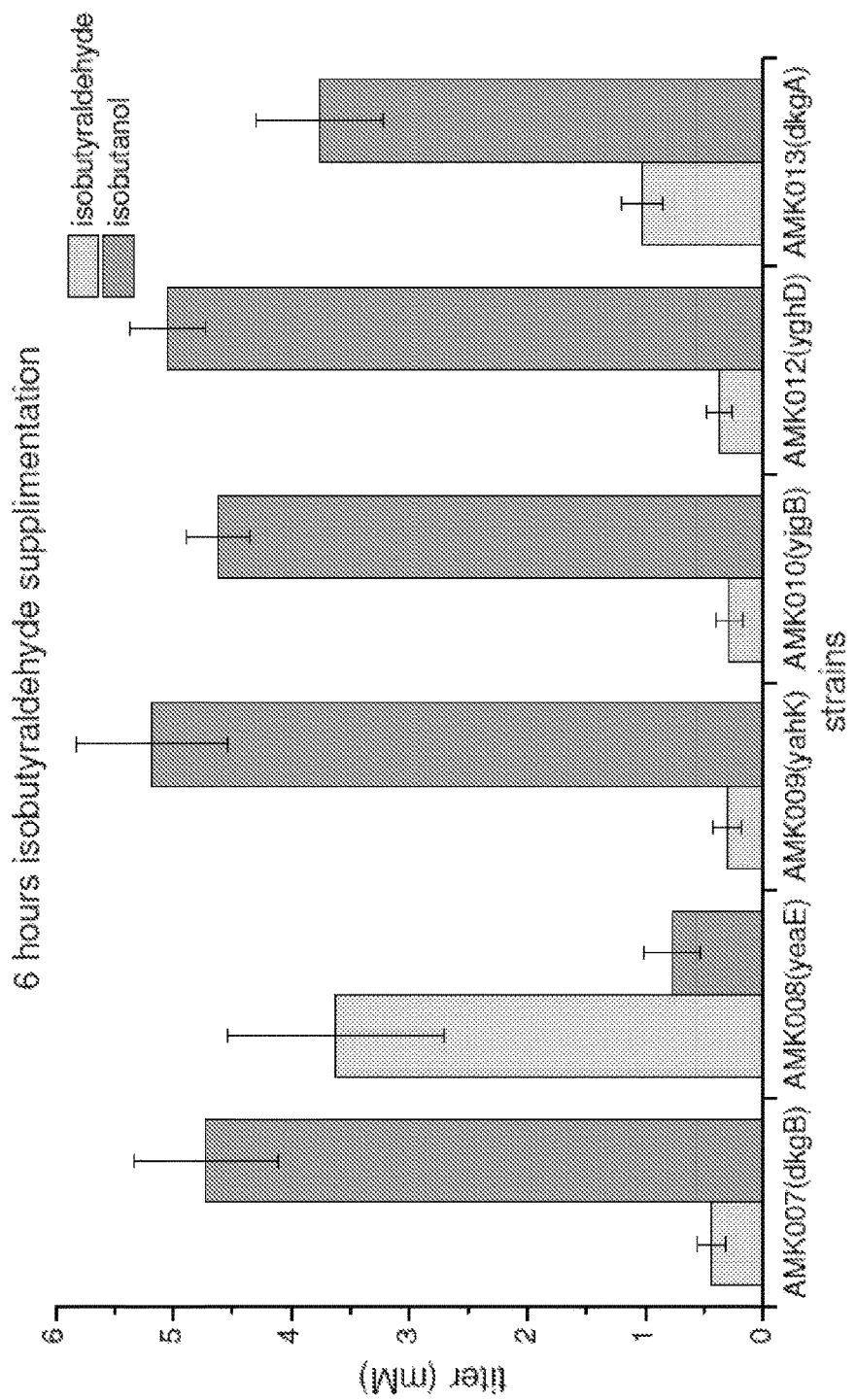
FIG. 15 shows isobutyraldehyde and isobutanol production by the strain MG1655(DE3) endA-recA-dkgB-yeaE-yahK-yjgB-yqhD-dkgA-yqhC- transformed with pACYC-car$_{Ni}$-sfp$_{Bs}$ and with pETDuet-1 containing each of the genes shown in parentheses. Strains were grown on LB supplemented with 5 mM isobutyraldehyde. In some embodiments, expression of all the aldo-keto reductases, except for yeaE, showed rapid reduction of isobutyraldehyde to isobutanol.
Figure 16A:
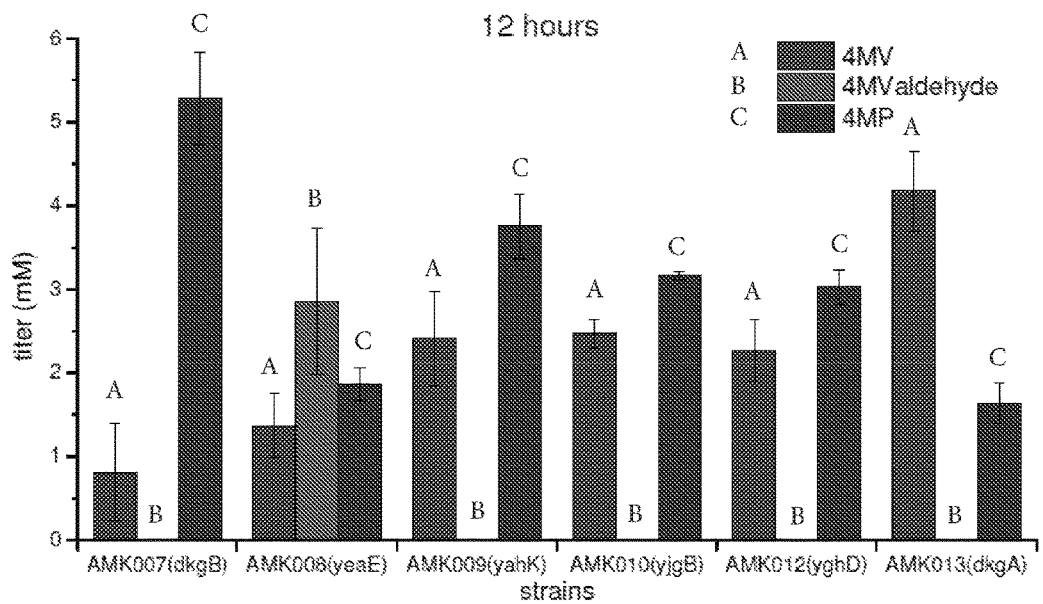
FIG. 16A and FIG. 16B shows results using the same strains as described in FIG. 15 but grown in LB supplemented with 5 mM 4-methyl-valerate which is converted by CarNi to 4-methyl-valeraldehyde. Variation in car$_{Ni}$ expression led to varying rates of 4-methyl-valerate conversion to 4-methyl-valeraldehyde, but in some embodiments all strains except the strain overexpressing yeaE completely reduced all aldehyde produced to alcohol. While some aldehyde built up by the 12 hour time point as depicted in FIG. 16A, by 24 hours no aldehyde was detected and significant conversion to 4-methyl-1-pentanol was observed and depicted in FIG. 16B. The same host strain containing empty pETDuet-1 without an aldo-keto reductase expressed showed minimal conversion to 4-methyl-1-pentanol in the same time period.
Figure 16B:
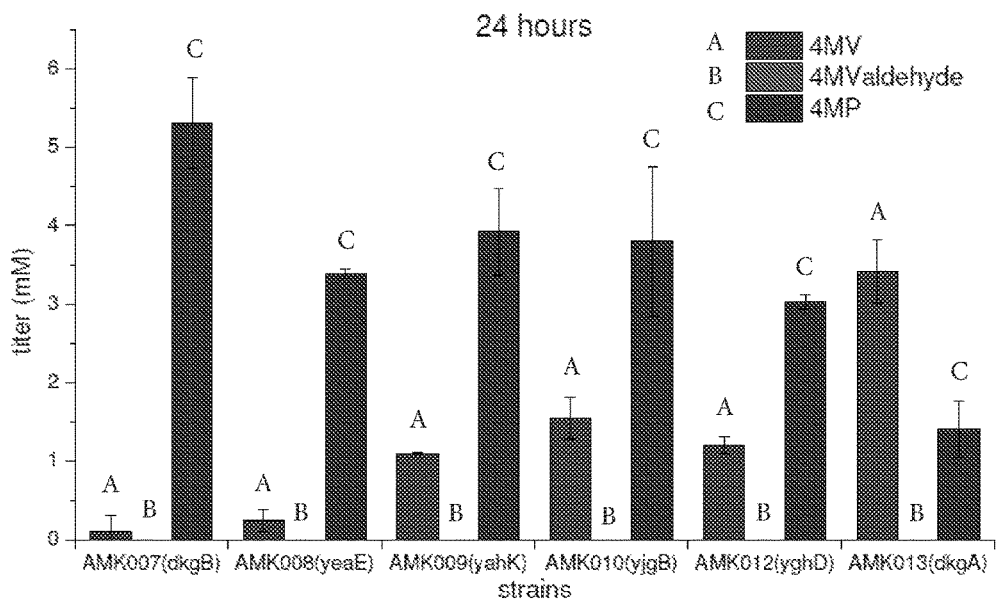

Together, these results suggested that an alternative reductase, possibly native to E. coli, could be used to improve pathway selectivity for 4-methyl-1-pentanol over isobutanol. YeaE$_{Ec}$, a native E. coli aldo-keto reductase, was selected as an alternative to ADH6$_{Sc}$ due to confirmed activity on medium-chain aldehydes while having relatively low activity on isobutyraldehyde (Aditya) (FIGS. 15 and 16).

A second reaction of focus was the oxidation of isobutyraldehyde to isobutyrate in Module 1. Native E. coli genes were screened for this reaction, and the aldehyde dehydrogenases puuC$_{Ec}$ and feaB$_{Ec}$ were initially selected. While Strain M1P2P3 expressing puuC$_{Ec}$ produced the highest 4-methyl-valerate titers, when Module 4 was added no 4-methyl-1-pentanol was observed. It is likely that puuC$_{Ec}$ can oxidize 4-methyl-valeraldehyde faster than reduction by ADH6$_{Sc}$ creating a futile cycle between 4-methyl-valerate and 4-methyl-valeraldehyde. Strain M1F2P34 with feaB$_{Ec}$ did produce 4-methyl-1-pentanol, but it is possible that feaB$_{Ec}$ still diverts flux back to 4-methyl-valerate wasting ATP. Indeed in vitro data suggests feaB$_{Ec}$ may have high activity on 4-methyl-valeraldehyde (Rodriguez-Zavala 2009). In some embodiments, a new aldehyde dehydrogenase from Flavobacterium johnsoniae (Fjoh_2967) is selected because it was documented to have strong preference for isobutyraldehyde in vitro (Yamanaka 2002).

Figure 19A:
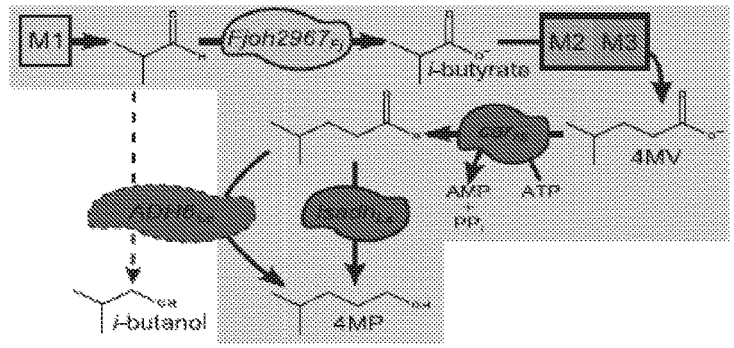
FIG. 19A depicts the desired pathway reactions to 4-methyl-1-pentanol are indicated by bold arrows with the byproduct shunt to isobutanol indicated by the dashed arrow. High activity of Adh6p$_{Sc}$ on isobutyraldehyde diverts isobutyrate flux to isobutanol. The Lsadh$_{Ls}$ alcohol dehydrogenase's selectivity for 4-methyl-valeraldehyde greatly reduces flux to the isobutanol shunt.
Figure 19B:
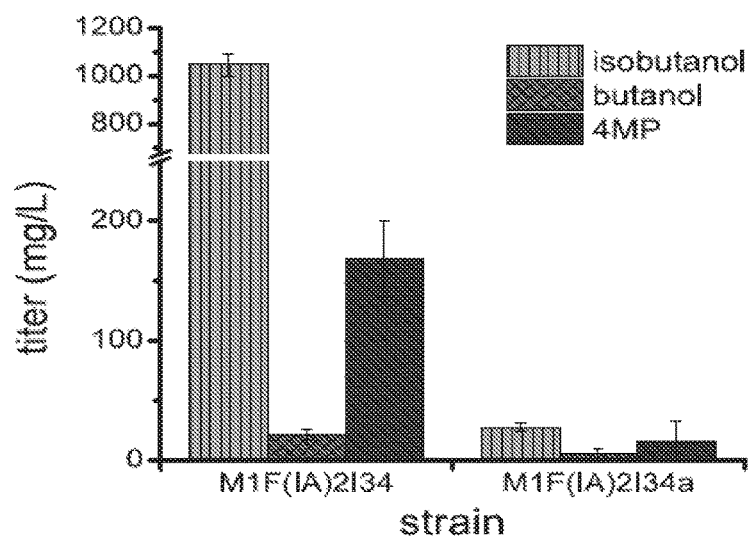
FIG. 19B shows the alcohol profile of Strain M1F(IA)2I34 expressing feaB$_{Ec}$ and ADH6$_{Sc}$ contains 168±31 mg/L of 4MP but is dominated by 1.046±45 g/L of isobutanol. The M1F(IA)2I34a control without ADH6$_{Sc}$ expression produces low to undetectable levels of all three alcohols.
Figure 19C:
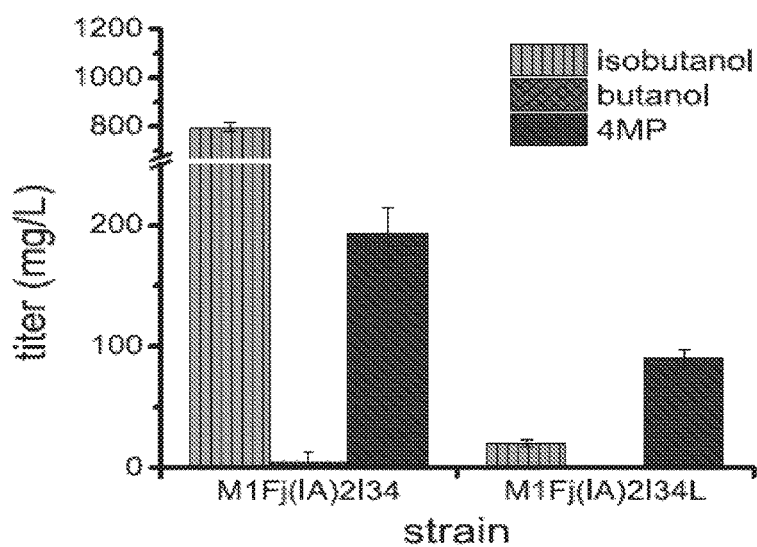
FIG. 19C Replacing feaB$_{Ec}$ with Fjoh2967$_{Fj}$ in Strain M1Fj(IA)2I34 reduces isobutanol (797±20 mg/L) and increases 4MP (192±23 mg/L) marginally. Replacing ADH6$_{Sc}$ with lsadh$_{Ls}$ greatly enhanced alcohol selectivity producing 90±7 mg/L 4MP with only 20±5 mg/L isobutanol.
Figure 20A:
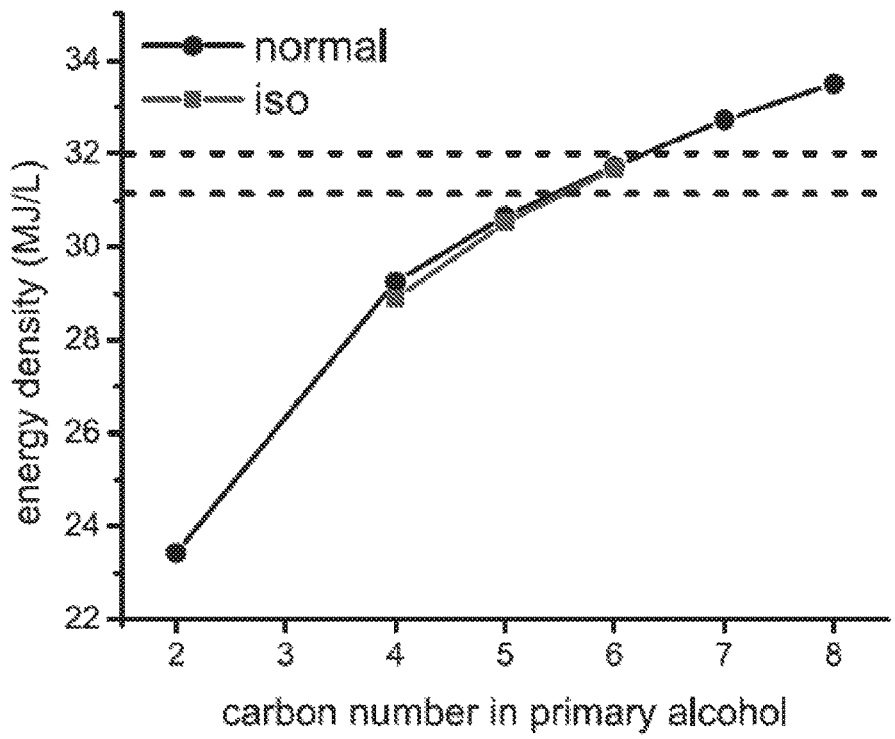
FIG. 20A shows energy densities (calculated from density (Bachmann 2010; Weeks 2011; Prather 2008) and heat of combustion data[4]) of normal and select iso isomers of primary alcohols from C2-C8 are shown. The black dotted line indicates the energy density of a traditional gasoline blend and the blue dotted line indicates the energy density of an E10 (10% ethanol) blend.
Figure 20B:
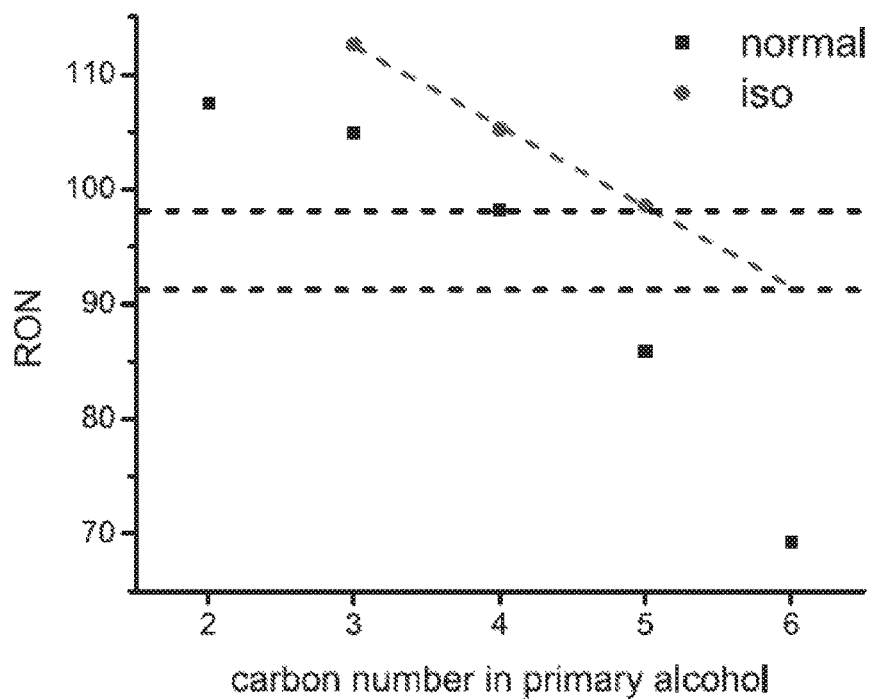
FIG. 20B shows RONs, which indicate how controllably a fuel burns in spark-ignition engines, are shown for normal and select iso isomers of primary alcohols from C2-C6 (adapted data). The black dotted line indicates the RON for a traditional gasoline blend and the blue dotted line indicates the RON for an E10 blend. The red dotted line indicates a linear extrapolation of iso branched alkanes up to a C6 isomer. Based on the extrapolation and measured value for n-hexanol, it is likely that the RON of 4-methyl-1-pentanol lies between 80 and 90.

With knowledge of the specificity of Car$_{Ni}$ for 4-methyl-valerate over isobutyrate, the continued high isobutanol titers suggested Adh6p$_{Sc}$ was converting the isobutyraldehyde intermediate to isobutanol (FIG. 19A). Removing ADH6s, from Strain M1F(IA)2I34 produced Strain M1F (IA)2I34a, which generated an isobutanol titer of 27±3 mg/L with nearly undetectable butanol and 4-methyl-pentanol titers (FIG. 19B). An alternative to ADH6$_{Sc}$ was identified from Leifsonia sp. Strain S749. The new alcohol dehydrogenase Lsadh$_{Ls}$ was hypothesized to have improved specificity for 4-methyl-valeraldehyde based on substrates that were assayed in vitro (Inoue 2005). When lsadh$_{Ls}$ was combined with the isobutyraldehyde specific dehydrogenase Fjoh2967Fj in Strain M1Fj(IA)2I34L, selective synthesis of 4-methyl-1-pentanol was achieved over other alcohol byproducts (FIG. 19C). Isobutanol titers were reduced to 21±3 mg/L, similar to those observed with the no alcohol dehydrogenase control. 4-methyl-pentanol was produced at 90±7 mg/L (0.016±0.001 mol/mol glucose) making up 81% of all alcohol products. The dominant byproducts were the 4-methyl-1-pentanol precursors acetate (592±34 mg/L, 0.177±0.010 mol/mol glucose) and isobutyrate (1128±34 mg/L, 0.229±0.002 mol/mol glucose), suggesting that byproduct shunts were reduced and further improvement could be made by relieving a downstream rate limitation in Module 2, 3, or 4 (FIG. 26). While 4-methyl-1-pentanol titers were lower with Lsadh$_{Ls}$, SDS-PAGE analysis of Lsadh$_{Ls}$ confirmed strong overexpression in E. coli (FIG. 26C). The reduction in titer is likely due to the change from an NADPH-dependent dehydrogenase (Adh6p$_{Sc}$) to an NADH-dependent dehydrogenase (Lsadh$_{Ls}$) under the aerobic conditions used. The ratio of NADH/NAD+ has been observed to be lower than that of NADPH/NAD+ under similar culture conditions (Tseng 2009).

Discussion

Recent efforts to develop pathways to microbially produced liquid fuels have led to the demonstration of a wide range of biofuel products. Modifications of natural pathways have generally led to either lighter or heavier biofuels than the medium-branched-chain structures found in gasoline. Development of microbial pathways for chemical synthesis have moved beyond upregulation of native pathways to include transfer and modification of heterologous pathways to new hosts and modified termination of native host pathways. Only a small number of truly de novo pathway designs have been published and most use isolated heterologous enzymes acting on their cognate substrates (Moon 2009; Niu 2003; Hansen 2009; Martin 2013). Engineered pathways to liquid fuels, in particular, have predominantly relied on entirely natural (ethanol, butanol, isoprenoid) or terminally modified natural pathways (fatty acid synthesis, amino acid αKAE, isoprenoid). Herein, enzymes from a variety of organisms and metabolic pathways were combined to build a novel pathway built on the framework of a reverse β-oxidation cycle. This work moves beyond modification of natural pathways by successfully demonstrating synthesis of a C6 branched alcohol via an extended de novo pathway which maintains selectivity while utilizing multiple naturally occurring enzymes outside their native pathway contexts. In order to avoid the inefficiency of αKAE, valine biosynthesis was coupled to extension by a de novo reverse β-oxidation pathway constructed from components of two different PHA pathways of C. necator and the trans-enoyl-reductase, ter, of T. denticola. Addition of reductases car$_{Ni}$ and ADH6$_{Sc}$ led to production of the target compound 4-methyl-1-pentanol. The pathway design described herein relies in some embodiments on endogenous thioesterase activity to produce the free acid substrate 4-methyl-valerate for Car$_{Ni}$. With higher pathway flux, a dedicated thioesterase with specificity for 4-methyl-valeryl-CoA could further direct flux to the desired product. 4-methyl-valerate titers from glucose and isobutyrate have been shown previously to be increased by selecting thioesterases with improved substrate preference.

While one set of Modules has been presented herein, alternate chemistries could be substituted for or combined with the selected modules to create new pathways to the same or alternate products. For example, an isobutyryl-CoA mutase or branched α-keto-acid decarboxylase route could be used to generate the isobutyryl-CoA precursor in place of Modules 1 and 2 (Bachmann 2010; Weeks 2011; Cracan 2010). Similarly, a FAS route could be substituted for Module 3 to generate the longer saturated acid substrate for Module 4 (Howard 2013). Using this design, individual alternative modules or module combinations can be directly compared to the existing pathway in vivo. In addition, entirely new classes of branched products (e.g., aldehydes, alkanes) could be made by using different Module 4 enzymes.

For the presented pathway, an iterative screening approach identified the enzymes catalyzing conversion of the downstream 4-methyl-valeraldehyde and upstream isobutyraldehyde intermediates as key components controlling selectivity of the pathway. The initial Module 4 alcohol dehydrogenase selected, Adh6p$_{Sc}$, proved to be highly active, but non-selective in the full pathway context. Module 4 displayed high activity on our desired substrate, but in vivo results with the full pathway suggested this module had a broad substrate range. Persistent high isobutanol titers from strains expressing Modules 1-4 suggested that Module 4 enzymes were interacting with isobutyrate and/or isobutyraldehyde. In vitro and in vivo data from Module 4 testing implicated the alcohol dehydrogenase, Adh6p$_{Sc}$, as the non-selective enzyme (FIG. 2, FIG. 19). By replacing Adh6p$_{Sc}$ with the isobutyraldehyde specific and NADH-dependent alcohol dehydrogenase, Lsadh$_{Ls}$, pathway selectivity and overall cofactor utilization were improved.

As with alcohol dehydrogenase candidates, we initially selected aldehyde dehydrogenases previously validated for an isobutyraldehyde substrate in an engineered pathway. Two endogenous enzymes, PuuC$_{EC}$ and FeaB$_{Ec}$, were previously identified as the most effective E. coli aldehyde dehydrogenases for isobutyraldehyde oxidation to isobutyrate (Zhang 2011). Of the two E. coli aldehyde dehydrogenases, FeaB$_{EC}$ proved to successfully synthesize 4-methyl-1-pentanol from glucose in Strain M1F2P34 expressing Modules 1, 2, 3, and 4 (FIG. 18B). Based on in vitro data one may predict PuuC$_{Ec}$ to function more effectively because its k$_{cat}$/K$_m$ is more consistent across substrate lengths while the k$_{cat}$/K$_m$ of FeaB$_{Ec}$ actually increases by an order of magnitude between propionaldehyde and hexanaldehyde substrates (Rodriguez-Zavala 2006; Jo 2008). In vivo results disproved this prediction with only FeaB$_{Ec}$ producing 4-methyl-1-pentanol (FIG. 18A). The better performance of FeaB$_{Ec}$ in the context of the full pathway may be explained by reported Km values for the two dehydrogenases. FeaB$_{EC}$ has Km values below 100 µM for relevant substrates while the Km values for PuuC$_{Ec}$ are 1 mM. PuuC$_{Ec}$ and FeaB$_{Ec}$ were tested in strains expressing ADH6$_{Sc}$. Like FeaB$_{Ec}$, Adh6p$_{Sc}$ has reported Km values for relevant substrates in the 100-200 µM range (Larroy 2002). Adh6p$_{Sc}$ was observed to have kcat values (100 sec−1) an order of magnitude higher than values observed for FeaB$_{EC}$ and PuuC$_{Ec}$ (10 sec−1) for related aliphatic aldehydes. Together these observed kinetics support the hypothesis that Adh6p$_{Sc}$ out-competes PuuC$_{Ec}$ and FeaB$_{Ec}$ for the isobutyraldehyde substrate. Isobutyraldehyde and reducing equivalents are diverted to isobutanol, lowering 4-methyl-1-pentanol titers (FIG. 23). Strain M1P2P34 with PuuC$_{Ec}$ produces significantly more isobutanol than Strain M1F2P34 with FeaB$_{Ec}$, as expected based on observed Km values.

In addition, in vitro data suggested that even though FeaB$_{Ec}$ functioned as an isobutyraldehyde dehydrogenase, it may also favor a 4-methyl-valeraldehyde substrate. The potential futile cycle created by activity on 4-methyl-valeraldehyde was avoided by using the isobutyraldehyde specific dehydrogenase Fjoh2967Fj from Flavobacterium johnsonaie (Yamanaka 2002). Replacing feaB$_{Ec}$ with Fjoh2967Fj led to increased isobutyrate and eliminated detectable 4-methyl valerate production (FIG. 18). Combining more selective alcohol and aldehyde dehydrogenases led to a highly selective overall pathway with the major byproduct being overflow of the upstream intermediate isobutyrate (FIG. 24). Together the results from alcohol and aldehyde dehydrogenase selection highlight the importance of considering both high activity and required selectivity when utilizing retro-biosynthetic screening. Proposing potential upstream pathways is required to identify intermediates which could have cross-reactivity with downstream enzymes.

The general route of the pathway described herein to 4-methyl-1-pentanol has the potential to reach energy yields equivalent to ethanol fermentation. Dugar and Stephanopoulos have outlined the importance of balancing reducing equivalents generated and consumed in a recombinant pathway if it is desired to reach theoretical yields (Dugar 2011). Using the 4-methyl-1-pentanol pathway enzymes described herein, the overall reaction can be written as:

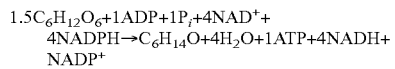

The reducing equivalents of the pathway are balanced, but are contained in different cofactors. One would expect to achieve up to 82% of the theoretical maximum yield using the current enzymes (Dugar 2011). If alternative enzymes are identified or engineered to accept NADH in place of the NADPH the pathway could achieve its theoretical maximum under anaerobic fermentation. The maximum pathway energy efficiency ($\eta^P$) can be calculated using the degrees of reductance and pathway stoichiometry for a glucose substrate and 4-methyl-1-pentanol product. Maximum pathway energy efficiency for the αKAE pathway and the presented CoA-dependent pathway are 75% and 100%, respectively. Accounting for cofactor requirements, the adjusted pathway energy efficiencies ($\eta^{P,G}_{CI}$) are 24% and 45% for the αKAE and CoA pathways, respectively. If alternative enzymes are identified or engineered to accept NADH in place of NADPH, maximum pathway yields could be achieved under anaerobic fermentation. The maximum adjusted efficiency values for these pathway architectures then become 28% (αKAE) and 100% (CoA). The yield calculations highlight how the rational design approach described herein leads to a pathway architecture with high yield potential unlike inherently limited pathways utilizing modification of amino acid synthesis.

The modular implementation of the pathway allows for in vivo evaluation of groups of pathway components even if direct in vitro assays for individual enzymes are impractical. With the desired CoA intermediates of the β-oxidation pathway (Module 3) not readily available, a dehydratase/reducatase combination was identified by isolating Modules 2 and 3 and generating the intermediates in vivo. A similar technique was used to identify a suitable Module 4 carboxylic acid reductase ($car_{Ni}$) and a minimal Module 1 enzyme set for production of isobutyrate ($alsS_{Bs}$-$ilvCD_{Ec}$). Combining Modules 2, 3, and 4 validated the selectivity of Car in vivo. Coupling Modules 1, 2, and 3 helped identify the kinetic limitation of relying on the decarboxylase activity of $alsS_{Bs}$ and led to the incorporation of a dedicated decarboxylase (kivD) and aldehyde dehydrogenase (feaB, puuC). Completion of the pathway to 4-methyl-1-pentanol by Module 4 expression revealed PuuC's activity on 4-methyl-valeraldehyde, leading to selection of FeaB as the isobutyraldehyde dehydrogenase. Pathway modules allowed for improved efficiency of pathway construction by enabling parallel in vivo screens of pathway components.

Module screening also helped refine hypotheses about product profiles for the full pathway. Results from Strains M1F2P3, designed for 4-methyl-1-valerate production from glucose, and M1(IA)2P34, designed for 4-methyl-1-pentanol production from glucose, indicated excessive flux from Module 1 generating acetoin (from acetolactate), isobutyrate, and isobutanol. The sharp increase in isobutanol titers with Module 4 present suggested observed isobutanol comes from reduction of either isobutyrate overflow by $Car_{Ni}$ or isobutyraldehyde by $ADH6_{Sc}$. Additionally, acetate titers for both strains expressing Module 1 were greatly reduced over those observed from Strain M2P34 when fed isobutyrate. These observations were combined to form two hypotheses: reducing expression of Module 1 enzymes may improve the balance of pyruvate flux between isobutyrate and acetyl-CoA and modification of Module 4 activity may lead to a reduction in isobutanol byproduct formation while still being sufficient for 4-methyl-1-pentanol production. Reshuffling of operon order and integration of the acetolactate synthase gene $alsS_{Bs}$ under an independent aTc inducible promoter showed that Module 1 flux could be modulated resulting in equal or higher titers of 4-methyl-1-pentanol with greatly reduced isobutanol formation (FIG. 11A and FIG. 11B). Since in vitro activity data for $Car_{Ni}$ makes significant reduction of isobutyrate by $Car_{Ni}$ unlikely in vivo, $ADH6_{Sc}$ was removed from Module 4 in an attempt to reduce isobutanol from isobutyraldehyde while relying on endogenous activity to reduce 4-methyl-valeraldehyde (FIG. 2). Without $ADH6_{Sc}$ isobutanol titers dropped to minimally detectable levels supporting the hypothesis that isobutanol was generated from the isobutyraldehyde intermediate.

These results highlight that while the overall pathway framework can lead to a redox neutral pathway to 4-methyl-1-pentanol, unbalanced and promiscuous enzyme activity can create inefficiencies. It was hypothesized that addressing the cross-reactivity of two enzymes acting on aldehyde intermediates would result in improving flux to 4-methyl-1-pentanol. As stated above. $ADH6_{Sc}$ is expressed for 4-methyl-valeraldehyde reduction, but it also reduces isobutyraldehyde so that it cannot be entirely oxidized to isobutyrate. Both carbon precursor and reducing equivalents are wasted by this reaction. Analogously, while $feaB_{EC}$ is expressed in Module 1 to oxidize isobutyraldehyde, it is likely that it also has activity on 4-methyl-valeraldehyde cycling the penultimate intermediate back to 4-methyl-valerate. Repeated reduction by $Car_{Ni}$ consumes additional ATP. In some embodiments, the alcohol dehydrogenase $ADH6_{Sc}$ was replaced by the aldo-keto reductase $yeaE_{Ec}$ and $feaB_{Ec}$ was replaced by F. johnsoniae aldehyde dehydrogenase Fjoh_2967 because these enzymes may have improved selectivity for the desired substrates of each reaction.

This work has identified a novel pathway for the synthesis of the branched medium-chain length alcohol 4-methyl-1-pentanol. The pathway architecture was selected to create a redox neutral pathway with the potential to reach theoretical yields on glucose. The highest titers (193=23 mg/L) were achieved with Strain M1Fj(IA)2I34 which expresses both $Fjoh2967_{Fj}$ and $ADH6_{Sc}$. Selectivity was achieved by replacing $ADH6_{Sc}$ with $lsadh_{Ls}$ in Strain M1Fj(IA)2I34L. The 90±7 mg/L of 4-methyl-1-pentanol produced by M1Fj(IA)2I34L represented 81% of observed alcohol products. In comparison, of the 9 alcohols generated in the previous demonstration of microbial 4-methyl-1-pentanol synthesis using α-KAE, 4-methyl pentanol (202.4±1.1 mg/L) makes up 14% of the total alcohol product (Zhang 2008). High potential efficiency and selectivity make our CoA pathway a preferred candidate for future engineering. Currently, the major byproducts of the CoA-dependent route are the acids acetate, isobutyrate, and butyrate (FIG. 26). It is expected that a combination of tuning thioesterase/transferase activities of the host to selectively cleave the longer 4-methyl-valeryl-CoA intermediate and relieving Module 3 rate limitations will further enhance titers. Ultimately, screening or engineering for NADH-dependent enzymes should produce a high yielding fermentative pathway. Pathways described herein can also be adapted to produce other branched medium-chain products by testing new downstream modules. Finally, the pathway design approach described herein can be useful for creation of new metabolic pathways which rely on long de novo routes. Using retro-biosynthetic screening within a proposed pathway framework allows exploration of diversity using a small number of assays while constraining enzyme space to a chemical route which is maximally efficient for a given product. Modular pathway design allowed for identification of component enzymes and helped to identify pathway limitations pointing the way towards selection of enzymes with improved selectivity and alternative gene expression architectures. Additional enzyme screening and pathway engineering could lead to improved titers and yields.

Materials and Methods

Bacterial Strains: *E. coli* MG655(DE3) ΔendA ΔrecA described previously (HCT10)(Tseng 2010) was the host strain for most production experiments, alcohol toxicity experiments, and protein expression analysis using cell lysates. *E. coli* MG1655(DE3) ΔendA ΔrecA lacZYA::tetR-Ptet-alsS was used for controlling Module 1 flux in select experiments where noted. *E. coli* DH10B (Invitrogen, Carlsbad, Calif.) and ElectroTen-Blue (Stratagene, La Jolla, Calif.) were used in plasmid cloning transformations and for plasmid propagation. *E. coli* BL21Star(DE3) (Life Technologies. Grand Island, N.Y.) was used for expression of car$_{Ni}$ for purification. (See Tables 1 & 2 for strain details)

Plasmids: A codon optimized version of *S. cerevisiae* ADH6 was purchased from DNA 2.0 (Menlo Park, Calif.), and codon optimized versions of *N. iowensis* car and *B. subtilis* sfp were purchased from GenScript (Piscataway, N.J.). *C. acetobutylicum* adhE, *T. denticola* ter and *E. gracilis* ter were purchased from GenScript (Piscataway, N.J.) as described previously (Tseng et al. 2012). *Leifsonia* sp. Strain S749 lsadh was purchased as a codon optimized GeneArt String from Life Technologies (Grand Island N.Y.). All other genes were amplified from gDNA. *B. subtilis* PY79, *E. coli* MG1655, *P. putida* KT2440, *C. necator* (formerly *R. eutropha*) H16, *M. elsdenii*, *R. palustris* CGA009, *P. syringae* DC3000, *C. acetobutylicum* ATCC824, and *S. oneidensis* MR-1 gDNA were prepared using the Wizard Genomic DNA purification Kit (Promega. Madison, Wis.). *P. aeruginosa* PAO1-LAC (ATCC#47085), *F. johnsoniae* (ATCC#17061), and *V. parahaemolyticus* EB 101 (ATCC#17802) gDNA were purchased from American Type Culture Collection (Manassas, Va.). Custom oligonucleotide primers were purchased (Sigma-Genosys, St. Louis, Mo.) for PCR amplification of genes from gDNA using either Phusion High-Fidelity DNA polymerase (Finnzymes, Thermo Scientific Molecular Biology) or Q5 High-Fidelity DNA polymerase (New England Biolabs, Ipswich, Mass.). Synthetic operons were constructed using a modified Splice by Overlap Extension (SOE) PCR method.

The compatible vector set pETDuet-1, pCDFDuet-1, pACYCDuet-1, and pCOLADuet-1 was used to express single genes or synthetic operons under control of a T7lac promoter and individual ribosome binding sites. Plasmids were constructed using standard molecular biology techniques with restriction enzymes and T4 DNA ligase purchased from New England Biolabs. Ligation products in pETDuet-1, pACYCDuet-1, and pCOLADuet-1 were used to transform *E. coli* DH10B and pCDFDuet-1 products were used to transform *E. coli* ElectroTen-Blue. Propagated constructs were purified using a QIAprep Miniprep Kit (Qiagen, Valencia, Calif.) and agarose gel fragments were purified using a Zymoclean Gel DNA Recovery Kit (Zymo Research, Irvine, Calif.). Completed constructs were cotransformed into *E. coli* MG1655(DE3) ΔendA ΔrecA. (See Table 4 for detailed plasmid description)

Splice by Overlap Extension: Initial PCR products with homologous ends were added to a PCR mixture without additional primers and cycled through a standard PCR cycle 4 times with annealing temperatures set at 6° C. above, 3° C. above, and at the designed melting temperature for the homology. The upstream primer for the upstream gene and the downstream primer for the downstream gene in the designed operon were then added to amplify the full length product. A standard PCR method using the annealing temperature for the primer pair was used for final amplification.

Culture Conditions: For all experiments, triplicate seed cultures were grown from isolated colonies at 30° C. overnight in 3 ml LB medium in a 14 ml culture tube on a rotary shaker at 250 rpm. All production cultures were inoculated with 1% inoculom from overnight seed culture and grown at 30° C. on a rotary shaker at 250 rpm. Cultures were induced with 0.5 mM IPTG when cultures reached mid-exponential phase with OD600 values 0.5-1.0.

For production of 4-methyl-valerate from glucose and isobutyrate, seed cultures were used to inoculate 50 ml of LB supplemented with 1% glucose and either 10 or 15 mM isobutyrate at a 1% inoculum volume in 250 ml shake flasks. For production of 4-methyl-valerate and 4-methyl-pentanol from glucose. LB medium supplemented with 1.2% glucose was used. Samples were taken 48 hours post induction, except for initial experiments with strains M1F2F34 and M1P2P34 when samples were taken at 72 hours post induction.

For production of 4-methyl-pentanol from glucose and isobutyrate, seed cultures were used to inoculate 3 ml of LB supplemented with 1% glucose and 10 mM isobutyrate at a 1% inoculum volume in 50 ml screw-capped glass tubes. Samples were taken 48 hours post induction.

For production of 4-methyl-valerate from glucose, seed cultures were used to inoculate 50 ml of LB supplemented with 1.2% glucose at a 1% inoculum volume in 250 ml shake flasks. Samples were taken at 48 and 72 hours.

For production of 4-methyl-pentanol from glucose, seed cultures were used to inoculate 3 ml of LB supplemented with 1.2% glucose at a 1% inoculum volume in 50 ml screw-capped glass tubes. Cultures were grown to mid-exponential phase with the screw-caps left loose and caps were tightened after induction. Samples were taken 72 hours post induction. For strains using the MG1655(DE3) endA recA lacZYA::tetR-Ptet-alsS$_{Bs}$ host anhydrotetracycline was added at 25, 125, or 250 ng/mL concomitantly with IPTG.

Genome Integration: The landing pad integration method developed by Kuhlman et al. was adapted for integration of the alsS$_{Bs}$ gene into the genome of MG1655(DE3) ΔendA ΔrecA. An aTc inducible promoter and the alsS$_{Bs}$ gene were integrated into the lacZYA locus leaving the native transcriptional terminator downstream of the integration.

For assessing toxicity of isobutanol and 4MP, an MG1655 (DE3) ΔendA ΔrecA seed culture was grown overnight in LB medium. Duplicate 3 ml cultures in LB+1.2% glucose+ alcohol were inoculated to an initial OD600 of 0.1. Cultures were contained in the same 50 ml screw-cap tubes used in production experiments. Cultures contained 1 mM isobutanol, 5 mM isobutanol, 10 mM isobutanol, 1 mM 4MP, 5 mM 4MP, 10 mM 4MP, or no alcohol. Growth was monitored by optical density and the growth rate was calculated from a linear regression of the natural log of the OD600 values for the 1.5, 2, and 2.5 hour post-inoculation time points.

Relative Activity Assay for Purified his-Car: An overnight culture of BL21 Star (DE3) (Invitrogen) harboring pET/His-Car-RBS2-Sfp was used as 10% (v/v) inoculum in 2 L of LB Broth. The culture was incubated at 30° C. and 250 rpm, and expression was induced using a final concentration of 1 mM IPTG at OD 0.6. Cells were harvested after 20 hours using centrifugation and resuspended in a buffer containing 50 mM Tris-HCl pH 8.0, 300 mM NaCl, and 10% glycerol. Cells were subsequently lysed using sonication. The supernatant was collected and applied to a column containing Ni-NTA resin (Qiagen). Affinity chromatography was performed using step-wise increasing concentrations of imidazole. Fractions containing purified His6-Car were dialyzed overnight at 4° C. into 50 mM Tris-HCl pH 7.5, 50 mM NaCl, 1 mM DTT, and 10% glycerol. Dialyzed enzyme was then flash frozen using liquid nitrogen and stored at −80° C. The activity of His-Car on various substrates was determined by changes in absorbance at 340 nm for up to 5 minutes in 96-well microplates using a plate reader (Tecan Infinite F200 Pro). Reactions were prepared as follows: 100 mM Tris-HCl pH 7.5, 10 mM MgCl2, 0.6 mM NADPH, 1 mM ATP, 224 nM His-Car, and 50 mM pH neutralized acid substrate. Changes in absorbance at 340 nm were detected using a filter. All substrates were assayed in triplicate. For $K_M$ and $V_{max}$ determinations, substrates were assayed at 5 different concentrations.

SDS-PAGE Analysis: E. coli MG1655(DE3) ΔendA ΔrecA was transformed with empty pETDuet-1, pET-(bkt-BCn-terTd)-(phaBCn-phaJ4bCn), pET-(bktBCn-terTd)-(phaJ4bCn-phaBCn) pACYC-(carNi-sfpBs)-ADH6Sc, or pACYC-(carNi-sfpBs)-lsadhLs. Single colonies from plates of each transformation were grown overnight in 3 ml of LB with appropriate antibiotic. Shake flask cultures (250 ml flasks) containing 50 ml LB+0.6% glucose were inoculated at 1% inoculum from overnight LB cultures and incubated with agitation at 30° C. and 250 rpm. Shake flasks were induced with 0.5 mM IPTG OD600 values between 0.5 and 0.6.

Five and a half hours after induction 7 ml of each culture were sampled and pelleted by centrifugation. Cell pellets were resuspended in 1 ml of 10 mM Tris-HCl at pH 8.0 and added to 1.7 ml microcentrifuge tubes containing 500 ul of 0.1 mm diameter glass beads (Scientific Industries, Inc. Disruptor Beads, SI-BG01). Samples were then vortexed for 10 minutes.

After lysis, samples were pelleted by centrifugation (6,000 g, 4° C., 10 min) and the supernatant was removed as soluble lysate. Total protein was quantified by a previously described Bradford assay method using Bio-Rad Protein Assay Dye Reagent (Cat #500-0006) (Zor 1996). A Bio-Rad 10% Mini-PROTEAN TGX gel (Cat #456-1034) was run using the Mini-PROTEAN Tetra Cell electrophoresis set up. Bio-Rad Precision Plus Protein All Blue Standard (Cat #161-0373) and 10 μg of total protein for each sample was loaded on the gel. After running at 200 volts for 33 minutes, the gel was washed with deionized water before staining with Bio-Rad Bio-Safe Coomassie Stain (Cat #161-0786).

Metabolite Analysis: Culture samples were pelleted by centrifugation and supernatant was removed for HPLC analysis with an Agilent 1200 series instrument with a refractive index detector. Analytes were separated using the Aminex HPX-87H anion exchange column (Bio-Rad Laboratories, Hercules, Calif.) with a 5 mM Sulfuric acid mobile phase at 35° C. and a flowrate of 0.6 ml/min. Commercial standards of glucose, alpha-ketoisovalerate, acetate, acetoin, isobutyrate, butyrate, isobutanol, butanol, 4-methly-valerate, and 4-methyl-pentanol were used for quantification of experimental samples by linear interpolation of external standard curves.

Pathway Yield Calculations: Yield calculations were computed as outlined in Dugar and Stephanopoulos (Duggar 2011). An explanation for the specific pathways cited in the current work follows. The maximum molar yield on an energy basis, $Y^E$, is calculated as the ratio of the degree of reductance of glucose, 24, over the degree of reductance of the product. The degree of reductance of 4MP is 36 giving a $Y^E$ of 0.67 mol 4-methyl-1-pentanol/mol glucose. The stoichiometric yield of each pathway, Y, is calculated by dividing the moles of product generated per mole of substrate. The maximum pathway energy efficiency is calculated as:

$$\gamma^P = \frac{\text{degree of reductance}_{prod} \cdot n_{prod}}{\text{degree of reductance}_{glu} \cdot n_{glu}} \cdot 100 = \frac{Y}{Y^E} \cdot 100$$

where n is the number of moles of product or substrate used in a given pathway.

In order to account for required NADPH generation and regeneration of excess NADH reducing equivalents, the stoichiometric pathway balance, $v_1$, can be coupled to the system of equations below:

—CH₂O−aNADPH+bProduct+cATP+dNADH+eCO2    $v_1$:

—CH₂O+2NADPH+CO2    $v_2$:

—CH₂O−⅓ATP−⅓NADH+CH₈/₃O (glycerol)    $v_3$:

Here a, b, c, d, and e are the pathway stoichiometric coefficients normalized by the number of glucose carbons consumed in the pathway. By matching the equation rates, different pathway yields can be calculated for each proposed pathway. If both NADPH cofactor generation and NADH regeneration through a glycerol sink (used as a potential regeneration route for a commercial production yeast strain) are considered, then an adjusted pathway yield, $Y_{CI}^{P,G}$, can be calculated as described in Dugar and Stephanopoulos (Dugar 2011).

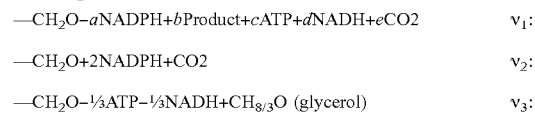

The adjusted molar pathway yield, $Y_{CI}^{P,G}$ can be divided by the maximum molar yield, $Y^E$, to find the adjusted energy efficiency.

$$\eta_{CI}^{P,G} = \frac{Y_{CI}^{P,G}}{Y^E} \cdot 100$$

The pathway coefficients for the αKAE pathway to 4-methyl-1-pentanol are: a=0.167, b=0.083, c=0333, d=0.667, and e=0.5. For the presented CoA-dependent 4MP pathway the coefficients are: a=0.333, b=0.111, c=0.111, d=0.333 and e=0.333.

Strains Used in Module 3 Screening and Plasmid Construct Comparison

Table 1 presents strains expressing 24 combinations of phaJ and ter genes shown in the top section with names indicating Module 3 screen ("M3Sc") followed by abbreviations for the organisms from which the ter and phaJ homologs were derived. "M3Sc-Ca" was used to confirm that the *C. acetobutylicum* hbd and crt genes did not produce branched products.

```
Codon Optimized Gene Sequences:
S. cerevisiae ADH6 (SEQ ID NO: 1):
ATGAGCTACCCGGAAAAGTTCGAGGGTATTGCTATTCAGTCCCATGA

GGACTGGAAGAACCCGAAGAAAACCAAGTATGATCCGAAGCCGTTCT

ACGACCACGACATCGACATCAAAATCGAAGCGTGCGGCGTGTGCGGT

AGCGATATCCACTGCGCAGCGGGCCACTGGGGTAACATGAAAATGCC

ACTGGTGGTGGGCCATGAGATTGTCGGTAAGGTGGTGAAACTGGGCC

CGAAGAGCAACAGCGGCCTGAAAGTTGGTCAGCGTGTGGGTGTTGGT

GCGCAAGTCTTTAGCTGTTTGGAATGTGATCGCTGTAAGAACGATAA

TGAACCGTATTGCACGAAGTTTGTTACCACCTATTCGCAACCTTATG

AGGATGGTTACGTCAGCCAAGGCGGTTATGCAAACTATGTGCGCGTT

CACGAGCACTTCGTTGTGCCGATTCCGGAGAATATCCCGAGCCATCT

GGCAGCACCGCTGCTGTGTGGCGGTCTGACGGTCTACTCCCCGCTGG

TCCGCAATGGTTGCGGTCCGGGCAAGAAAGTGGGCATTGTTGGTCTG

GGTGGCATCGGTTCTATGGGCACGTTGATTTCGAAGGCCATGGGTGC

GGAGACTTACGTCATCTCTCGTTCTAGCCGCAAACGTGAGGACGCGA

TGAAGATGGGTGCCGATCACTACATTGCGACCCTGGAAGAGGGTGAC

TGGGGCGAGAAATACTTTGACACCTTCGATCTGATTGTTGTGTGCGC

GAGCAGCCTGACGGATATTGACTTTAACATTATGCCAAAAGCCATGA

AAGTCGGTGGCCGCATCGTTTCCATTAGCATCCCTGAACAGCACGAG

ATGCTGAGCCTGAAGCCGTACGGTCTGAAGGCAGTTAGCATTAGCTA

CAGCGCTCTGGGCTCCATCAAAGAACTGAATCAGCTGCTGAAATTGG

TGAGCGAAAAAGACATCAAGATCTGGGTTGAAACCCTGCCGGTGGGT

GAGGCAGGTGTCCACGAGGCCTTTGAGCGTATGGAAAAAGGCGATGT

GCGTTATCGTTTCACCCTGGTTGGTTACGATAAAGAATTCAGCGAC

N. iowensis car (SEQ ID NO: 2):
ATGGCTGTGGACTCGCCGGATGAACGCCTGCAACGCCGTATCGCCCA

ACTGTTTGCCGAAGATGAACAAGTGAAAGCTGCCCGCCCGCTGGAAG

CAGTTAGCGCGGCCGTCTCTGCACCGGGTATGCGTCTGGCTCAGATC

GCAGCTACGGTGATGGCTGGTTATGCGGATCGTCCGCGGCGGGCCA

GCGTGCTTTCGAACTGAATACCGATGACGCAACCGGCCGTACCAGCC

TGCGTCTGCTGCCGCGTTTTGAAACCATTACGTACCGCGAACTGTGG

CAGCGTGTCGGCGAAGTGGCAGCTGCGTGGCATCACGACCCGGAAAA

CCCGCTGCGTGCGGGTGATTTTGTGGCCCTGCTGGGCTTCACCAGCA

TTGATTATGCAACGCTGGATCTGGCTGACATCCATCTGGGTGCGGTT

ACCGTGCCGCTGCAAGCGAGCGCGGCGGTGTCCCAACTGATTGCAAT

CCTGACCGAAACGAGTCCGCGCCTGCTGGCGTCCACCCCGGAACATC

TGGATGCTGCGGTGGAATGCCTGCTGGCAGGCACCACGCCGGAACGT

CTGGTGGTTTTCGATTATCACCCGGAAGATGACGATCAGCGCGCCGC

ATTTGAAAGTGCGCGTCGCCGTCTGGCAGATGCAGGTTCCCTGGTGA

TCGTTGAAACCCTGGACGCGGTGCGTGCGCGTGGCCGTGATCTGCCG

GCTGCGCCGCTGTTTGTCCCGGATACCGACGATGACCCGCTGGCGCT

GCTGATTTATACGTCAGGTTCGACCGGCACGCCGAAAGGTGCCATGT

ACACCAATCGTCTGGCCGCAACGATGTGGCAGGGCAACTCAATGCTG

CAAGGCAACAGCCAACGCGTTGGCATTAACCTGAATTATATGCCGAT

GAGTCATATTGCGGGTCGTATCTCCCTGTTCGGCGTGCTGGCGCGTG

GCGGCACCGCATACTTTGCTGCGAAATCAGACATGAGCACCCTGTTT

GAAGATATTGGCCTGGTTCGCCCGACCGAAATCTTTTTCGTTCCGCG

TGTCTGTGACATGGTGTTTCAGCGCTATCAAAGCGAACTGGATCGCC

GTTCTGTCGCTGGTGCGGATCTGGACACCCTGGACCGCGAAGTGAAA

GCGGATCTGCGTCAGAATTACCTGGGCGGTCGCTTCCTGGTTGCAGT

CGTGGGCTCGGCTCCGCTGGCCGCAGAAATGAAAACGTTTATGGAAA

GCGTGCTGGACCTGCCGCTGCATGATGGTTATGGCAGTACCGAAGCC

GGCGCATCCGTTCTGCTGGATAACCAGATCCAACGTCCGCCGGTCCT

GGACTATAAACTGGTCGATGTGCCGGAACTGGGTTACTTTCGCACGG

ATCGTCCGCACCCGCGTGGCGAACTGCTGCTGAAAGCAGAAACCACG

ATTCCGGGTTATTACAAACGCCCGGAAGTTACGGCGGAAATCTTTGA

TGAAGACGGCTTCTATAAAACCGGCGATATTGTGGCCGAACTGGAAC

ATGACCGCCTGGTTTACGTGGATCGTCGTAACAATGTTCTGAAACTG

TCCCAGGGCGAATTTGTGACCGTTGCGCACCTGGAAGCTGTGTTCGC

GAGCAGCCCGCTGATCCGTCAAATTTTTATCTATGGTAGTTCCGAAC

GCAGTTACCTGCTGGCCGTCATTGTGCCGACCGATGACGCACTGCGT

GGCCGCGATACCGCTACGCTGAAAAGCGCTCTGGCGGAATCTATTCA

GCGTATCGCCAAAGACGCAAATCTGCAACCGTATGAAATTCCGCGCG

ATTTTCTGATCGAAACCGAACCGTTCACGATTGCCAATGGCCTGCTG

AGCGGTATCGCAAAACTGCTGCGCCCGAACCTGAAAGAACGTTATGG

TGCGCAGCTGGAACAAATGTACACCGACCTGGCTACGGGCCAGGCAG

ATGAACTGCTGGCCCTGCGCCGTGAAGCTGCGGATCTGCCGGTGCTG

GAAACCGTTAGCCGTGCCGCAAAAGCGATGCTGGGTGTGGCAAGCGC

GGATATGCGTCCGGACGCACATTTTACCGATCTGGGCGGTGACAGCC

TGTCTGCACTGAGTTTTTCCAACCTGCTGCACGAAATCTTCGGTGTT

GAAGTCCCGGTGGGTGTTGTCGTGTCTCCGGCAAACGAACTGCGTGA

TCTGGCGAATTATATTGAAGCCGAACGCAACAGTGGCGCAAAACGTC
```

```
CGACCTTCACGTCAGTGCATGGCGGTGGCTCGGAAATTCGTGCTGCG
GATCTGACCCTGGACAAATTTATCGATGCACGCACGCTGGCCGCAGC
TGATTCTATTCCGCACGCCCCGGTGCCGGCACAGACCGTTCTGCTGA
CGGGTGCGAATGGCTATCTGGGTCGTTTCCTGTGCCTGGAATGGCTG
GAACGCCTGGATAAAACCGGCGGCACCCTGATTTGTGTTGTCCGTGG
TAGCGACGCGGCGGCGGCACGTAAACGTCTGGATTCAGCCTTTGATA
GCGGCGATCCGGGCCTGCTGGAACATTATCAGCAACTGGCAGCACGT
ACCCTGGAAGTGCTGGCAGGCGATATTGGTGACCCGAACCTGGGCCT
GGATGACGCGACCTGGCAGCGTCTGGCAGAAACGGTCGATCTGATTG
TGCATCCGGCAGCTCTGGTGAATCACGTTCTGCCGTACACCCAGCTG
TTTGGCCCGAACGTGGTTGGCACCGCGGAAATTGTGCGCCTGGCTAT
CACCGCGCGTCGTAAACCAGTGACCTATCTGTCTACGGTTGGCGTCG
CAGATCAGGTTGACCCGGCTGAATACCAAGAAGATAGCGATGTGCGT
GAAATGTCTGCGGTGCGTGTCGTGCGCGAAAGCTATGCCAACGGTTA
CGGCAATTCTAAATGGGCTGGTGAAGTGCTGCTGCGCGAAGCGCATG
ATCTGTGCGGTCTGCCGGTGGCAGTTTTTCGTTCAGATATGATTCTG
GCACACTCGCGCTATGCTGGTCAGCTGAATGTCCAAGATGTGTTCAC
CCGTCTGATTCTGTCACTGGTTGCTACGGGCATCGCGCCGTATTCGT
TTTACCGCACCGATGCAGACGGTAACCGTCAGCGCGCCCATTACGAT
GGTCTGCCGGCAGATTTCACCGCGGCGGCGATTACGGCGCTGGGTAT
CCAGGCCACCGAAGGCTTTCGCACGTATGATGTGCTGAATCCGTATG
ATGACGGTATTAGTCTGGACGAATTTGTTGATTGGCTGGTCGAATCC
GGCCATCCGATTCAGCGTATCACGGATTATTCAGACTGGTTTCACCG
CTTCGAAACCGCCATCCGTGCACTGCCGGAAAAACAGCGTCAAGCCA
GCGTGCTGCCGCTGCTGGATGCATACCGTAACCCGTGTCCGGCCGTT
CGCGGTGCAATTCTGCCGGCTAAAGAATTTCAGGCTGCGGTCCAAAC
CGCGAAAATTGGCCCGGAACAGGATATTCCGCACCTGAGTGCCCCGC
TGATTGATAAATACGTGTCTGACCTGGAACTGCTGCAACTGCTGTAA

B. subtilis sfp (SEQ ID NO: 3):
ATGAAAATCTATGGCATTTACATGGATCGTCCGCTGAGTCAGGAAGA
AAACGAACGCTTTATGACCTTCATCAGCCCGGAAAAACGTGAAAAAT GCCGTCGCTTTTATCATAAAGAAGATGCACACCGCACGCTGCTGGGC
GATGTGCTGGTTCGTAGCGTGATCTCTCGCCAGTATCAGCTGGATAA
ATCTGATATTCGTTTCAGTACCCAGGAATACGGTAAACCGTGTATTC
CGGATCTGCCGGATGCACATTTTAATATCAGCCACTCTGGCCGCTGG
GTTATTGGTGCGTTCGATTCTCAGCCGATTGGTATCGATATTGAAAA
AACGAAACCGATCAGTCTGGAAATTGCCAAACGTTTCTTTAGCAAAA
CCGAATATTCTGATCTGCTGGCAAAAGATAAAGATGAACAGACGGAT
TACTTTTACCATCTGTGGAGTATGAAAGAATCTTTTATCAAACAGGA
AGGCAAAGGTCTGAGCCTGCCGCTGGATAGTTTTAGCGTGCGCCTGC
ATCAGGATGGCCAGGTTTCTATCGAACTGCCGGATTCTCACAGTCCG
TGCTATATTAAAACCTACGAAGTTGATCCGGGCTATAAAATGGCCGT
TTGTGCGGCCCACCCGGATTTCCCGGAAGATATTACGATGGTGAGCT
ACGAAGAACTGCTGTAA L. sp. Strain S749 lsadh (SEQ ID NO: 4):
ATGGCCCAGTATGATGTTGCAGATCGTAGCGCAATTGTTACCGGTGG
TGGTAGCGGTATTGGTCGTGCAGTTGCACTGACCCTGGCAGCAAGCG
GTGCAGCAGTTCTGGTTACCGATCTGAATGAAGAACATGCACAGGCA
GTTGTTGCAGAAATTGAAGCAGCCGGTGGTAAAGCAGCAGCACTGGC
TGGTGATGTGACCGATCCGGCATTTGGTGAAGCAAGCGTTGCCGGTG
CAAATGCACTGGCACCGCTGAAAATTGCAGTTAATAATGCAGGTATT
GGTGGTGAAGCCGCAACCGTTGGTGATTATTCACTGGATAGCTGGCG
TACCGTTATTGAAGTTAATCTGAATGCCGTGTTTTATGGTATGCAGC
CGCAGCTGAAAGCAATGGCAGCAAATGGTGGTGGTGCCATTGTTAAT
ATGGCAAGCATTCTGGGTAGCGTTGGTTTTGCAAATAGCAGCGCCTA
TGTTACCGCAAAACATGCACTGCTGGGCCTGACACAGAATGCAGCCC
TGGAATATGCAGCAGATAAAGTTCGTGTTGTTGCCGTTGGTCCGGGT
TTTATTCGTACACCGCTGGTTAAGCAAATCTGAGCGCAGATGCCCT
GGCATTTCTGGAAGGTAAACATGCCCTGGGTCGTCTGGGTGAACCGG
AAGAAGTTGCAAGCCTGGTTGCCTTTCTGGCAAGTGATGCAGCAAGC
TTTATTACCGGTAGCTATCATCTGGTTGATGGTGGTTATACCGCACA
GTAA
```

TABLE 1

Strains used in Module 3 Screening and Plasmid Construct Comparison

| Host strain | Plasmid 1 | Plasmid 2 | Strain name |
| --- | --- | --- | --- |
| MG1655(DE3) endA recA | pET-ter$_{Td}$-(bktB$_{Cn}$-pct$_{Me}$) | pCDF-phaJ4b$_{Cn}$-phaB$_{Cn}$ | M3Sc-TdCn |
| | | pCDF-phaJ4$_{Pa}$-phaB$_{Cn}$ | M3Sc-TdPa4 |
| | | pCDF-phaJ4$_{Ps}$-phaB$_{Cn}$ | M3Sc-TdPs |
| | | pCDF-phaJ1$_{Pa}$-phaB$_{Cn}$ | M3Sc-TdPa1 |
| | pET-ter$_{Vp}$-(bktB$_{Cn}$-pct$_{Me}$) | pCDF-phaJ4b$_{Cn}$-phaB$_{Cn}$ | M3Sc-VpCn |
| | | pCDF-phaJ4$_{Pa}$-phaB$_{Cn}$ | M3Sc-VpPa4 |
| | | pCDF-phaJ4$_{Ps}$-phaB$_{Cn}$ | M3Sc-VpPs |
| | | pCDF-phaJ1$_{Pa}$-phaB$_{Cn}$ | M3Sc-VpPa1 |

TABLE 1-continued

Strains used in Module 3 Screening and Plasmid Construct Comparison

| Host strain | Plasmid 1 | Plasmid 2 | Strain name |
|---|---|---|---|
| | pET-ter$_{Sc}$-(bktB$_{Cn}$-pct$_{Me}$) | pCDF-phaJ4b$_{Cn}$-phaB$_{Cn}$ | M3SC-SoCn |
| | | pCDF-phaJ4$_{Pa}$-phaB$_{Cn}$ | M3Sc-SoPa4 |
| | | pCDF-phaJ4$_{Ps}$-phaB$_{Cn}$ | M3Sc-SoPs |
| | | pCDF-phaJ1$_{Pa}$-phaB$_{Cn}$ | M3Sc-SoPa1 |
| | pET-ter$_{Eg}$-(bktB$_{Cn}$-pct$_{Me}$) | pCDF-phaJ4b$_{Cn}$-phaB$_{Cn}$ | M3Sc-EgCn |
| | | pCDF-phaJ4$_{Pa}$-phaB$_{Cn}$ | M3Sc-EgPa4 |
| | | pCDF-phaJ4$_{Ps}$-phaB$_{Cn}$ | M3Sc-EgPs |
| | | pCDF-phaJ1$_{Pa}$-phaB$_{Cn}$ | M3Sc-EgPa1 |
| | pET-ter$_{Pa}$-(bktB$_{Cn}$-pct$_{Me}$) | pCDF-phaJ4b$_{Cn}$-phaB$_{Cn}$ | M3Sc-PaCn |
| | | pCDF-phaJ4$_{Pa}$-phaB$_{Cn}$ | M3Sc-PaPa4 |
| | | pCDF-phaJ4$_{Ps}$-phaB$_{Cn}$ | M3Sc-PaPs |
| | | pCDF-phaJ1$_{Pa}$-phaB$_{Cn}$ | M3Sc-PaPa1 |
| | pET-ter$_{Ps}$-(bktB$_{Cn}$-pct$_{Me}$) | pCDF-phaJ4b$_{Cn}$-phaB$_{Cn}$ | M3Sc-PsCn |
| | | pCDF-phaJ4$_{Pa}$-phaB$_{Cn}$ | M3Sc-PsPa4 |
| | | pCDF-phaJ4$_{Ps}$-phaB$_{Cn}$ | M3Sc-PsPs |
| | | pCDF-phaJ1$_{Pa}$-phaB$_{Cn}$ | M3Sc-PsPa1 |
| | pET-ter$_{Td}$-(bktB$_{Cn}$-pct$_{Me}$) | pCDF-hbd$_{Ca}$-crt$_{Ca}$ | M3Sc-Ca |

Pentanol Pathway Strains for Evaluating Car$_{Ni}$ Specificity

Three plasmid strains for pentanol production are described in Table 2. All strains contained a plasmid for upregulation of the threonine biosynthesis pathway for production of the propionyl-CoA precursor α-ketobutyrate (pCOLA-thrAfrBC$_{EC}$-ilvAfr$_{Cg}$). Each Module 3 plasmid was paired with either the car$_{Ni}$-sfp$_{Bs}$-ADH6$_{Sc}$ or adhE$_{Ca}$ Module 4 plasmid.

TABLE 2

Pentanol Pathway Strains for Evaluating Car$_{Ni}$ Specificity

| Host strain | Plasmid 1 | Plasmid 2 | Plasmid 3 | Strain name |
|---|---|---|---|---|
| MG1655(DE3) endA recA | pCOLA-thrA$^{fr}$BC$_{Ec}$-ilvA$^{fr}$$_{Cg}$ | pET-(bktB$_{Cn}$-ter$_{Td}$)-(phaJ4b$_{Cn}$-phaB$_{Cn}$) | pACYC-(car$_{Ni}$-sfp$_{Bs}$)-ADH6$_{Sc}$ | M1Pr3Cn4csA |
| | | | pACYC-adhE$_{Ca}$ | M1Pr3Cn4aE |
| | | pET-(bktB$_{Cn}$-ter$_{Td}$)-(crt$_{Ca}$-hbd$_{Ca}$) | pACYC-(car$_{Ni}$-sfp$_{Bs}$)-ADH6$_{Sc}$ | M1Pr3Ca4csA |
| | | | pACYC-adhE$_{Ca}$ | M1Pr3Ca4aE |

Strains Used for Module and Full Pathway Evaluation

Host strains and plasmids are listed in Table 3. Strain names indicate the modules present in the strain, i.e. M1F2P34 includes "M" for modules, "1F" for Module 1 with feaB$_{Ec}$, "2P" for Module 2 with pct$_{Me}$, "3" for Module 3 and "4" for Module 4. Strains with "( )" contain abbreviations for operon structure indicating the order of alsS$_{Bs}$ and ilvC$_{Ec}$ with "int" indicating strains with alsS$_{Bs}$ integrated in the genome under an aTc inducible promoter. Strains that were found to be key strains in some embodiments are indicated in bold.

TABLE 3

Strains used for Module and Full Pathway Evaluation

| Host strain | Plasmid 1 | Plasmid 2 | Strain name |
|---|---|---|---|
| MG1655(DE3) endA recA | pET-(bktB$_{Cn}$-pct$_{Me}$)-ter$_{Td}$ | pCDF-phaJ4b$_{Cn}$-phaB$_{Cn}$ | M2P3a |
| | pET-(bktB$_{Cn}$-ter$_{Td}$)-(phaJ4b$_{Cn}$-phaB$_{Cn}$) | pCDF-pct$_{Me}$ | M2P3b |
| | pET-(bktB$_{Cn}$-ter$_{Td}$)-(phaB$_{Cn}$-phaJ4b$_{Cn}$) | pCDF-pct$_{Me}$ | M2P3c |

| Host strain | Plasmid 1 | Plasmid 2 | Plasmid 3 | Strain name |
|---|---|---|---|---|
| MG1655(DE3) endA recA | pACYC-(car$_{Ni}$-sfp$_{Bs}$)-ADH6$_{Sc}$ | — | — | M4 |
| | pACYC-(car$_{Ni}$-sfp$_{Bs}$)-ADH6$_{Sc}$ | pET-ter$_{Td}$-(bktB$_{Cn}$-pct$_{Me}$) | pCDF-phaJ4b$_{Cn}$-phaB$_{Cn}$ | M2P34 |
| | pACYC-(alsS$_{Bs}$-ilvCD$_{Ec}$) | — | — | M1a |
| | pACYC-(alsS$_{Bs}$-ilvCD$_{Ec}$) | pET-ter$_{Td}$-bktB$_{Cn}$-pct$_{Me}$ | pCDF-pnaJ4b$_{Cn}$-phaB$_{Cn}$ | M1a2P3-a |
| | pET-(bktB$_{Cn}$-pct$_{Me}$)- | pCDF-(ilvD$_{Ec}$-ter$_{Td}$) | pCOLADuet-1 | M1a2P3-b |

TABLE 3-continued

Strains used for Module and Full Pathway Evaluation

| | (phaJ4$_{Cn}$-phaB$_{Cn}$) | (alsS$_{Bs}$-ilvC$_{Ec}$) | pCOLA-kivD$_{Ll}$-feaB$_{Ec}$ | M1F2P3 |
|---|---|---|---|---|
| | | | pCOLA-kivD$_{Ll}$-puuC$_{Ec}$ | M1P2P3 |

| Host strain | Plasmids 1, 2, & 3 | Plasmid 4 | Strain name |
|---|---|---|---|
| MG1655(DE3) | pET-(bktB$_{Cn}$-pct$_{Me}$)-(phaJ4b$_{Cn}$-phaB$_{Cn}$) | pCOLA-kivD$_{Ll}$-feaB$_{Ec}$ | M1F2P34 |
| endA recA | pCDF-(ilvD$_{Ec}$-ter$_{Td}$)-(alsS$_{Bs}$-ilvC$_{Ec}$) | pCOLA-kivD$_{Ll}$-puuC$_{Ec}$ | M1P2P34 |
| | pACYC-(car$_{Ni}$-sfp$_{Bs}$)-ADH6$_{Sc}$ | | |
| | pET-(bktB$_{Cn}$-ter$_{Td}$)-(phaJ4b$_{Cn}$-phaB$_{Cn}$) | pCDF-(pct$_{Me}$-ilvD$_{Ec}$)-(alsS$_{Bs}$-ilvC$_{Ec}$) | M1(AI)2P34 |
| | pCOLA-kivD$_{Ll}$-feaB$_{Ec}$ | pCDF-(pct$_{Me}$-ilvD$_{Ec}$-)-(ilvC$_{Ec}$-alsS$_{Bs}$) | M1(IA)2P34 |
| | pACYC-(car$_{Ni}$-sfp$_{Bs}$)-ADH6$_{Sc}$ | pCDF-(ibuA$_{Rp}$-ilvD$_{Ec}$)-(alsS$_{Bs}$-ilvC$_{Ec}$) | M1(AI)2I34 |
| | | pCDF-(ibuA$_{Rp}$-ilvD$_{Ec}$)-(ilvC$_{Ec}$-alsS$_{Bs}$) | M1(IA)2I34 |
| | | pCDF-(pct$_{Me}$-ilvD$_{Ec}$)-(ilvC$_{Ec}$) | M1(I)2P34 |
| | | pCDF-(ibuA$_{Rp}$-ilvD$_{Ec}$)-(ilvC$_{Ec}$) | M1(I)2I34 |
| MG1655(DE3) | pET-(bktB$_{Cn}$-ter$_{Td}$)-(phaJ4b$_{Cn}$-phaB$_{Cn}$) | pCDF-(pct$_{Me}$-ilvD$_{Ec}$)-(ilvC$_{Ec}$) | M1(I)int2P34 |
| endA recA | pCOLA-kivD$_{Ll}$-feaB$_{Ec}$ | pCDF-(ibuA$_{Rp}$-ilvD$_{Ec}$)-(ilvC$_{Ec}$) | M1(I)int2I34 |
| lacZYA::tetR-P$_{ter}$-alsS$_{Bs}$ | pACYC-(car$_{Ni}$-sfp$_{Bs}$)-ADH6$_{Sc}$ | | |
| MG1655(DE3) | pET-(bktB$_{Cn}$-ter$_{Td}$)-(phaJ4b$_{Cn}$-phaB$_{Cn}$) | pCDF-(pct$_{Me}$-ilvD$_{Ec}$)-(ilvC$_{Ec}$) | M1(I)int2P34a |
| endA recA | pCOLA-kivD$_{Ll}$-feaB$_{Ec}$ | pCDF-(ibuA$_{Rp}$-ilvD$_{Ec}$)-(ilvC$_{Ec}$) | M1(I)int2I34a |
| lacZYA::tetR-P$_{ter}$-alsS$_{Bs}$ | pACYC-(car$_{Ni}$-sfp$_{Bs}$) | | |

| Host strain | Plasmid 1 | Plasmid 2 | Plasmid 3 | Strain name |
|---|---|---|---|---|
| MG1655(DE3) | pET-(bktB$_{Cn}$-ter$_{Td}$)- | pCOLA-kivD$_{Ll}$-feaB$_{Ec}$ | pCDF-(pct$_{Me}$-ilvD$_{Ec}$)- | M1(I)int2P34a-3p |
| endA recA | (phaB$_{Cn}$-phaJ4b$_{Cn}$) | | (ilvC$_{Ec}$-car$_{Ni}$-sfp$_{Bs}$) | |
| lacZYA::tetR-P$_{ter}$-alsS$_{Bs}$ | | | pCDF-(ibuA$_{Rp}$-ilvD$_{Ec}$)- | M1(I)int2I34a-3p |
| | | | (ilvC$_{Ec}$-car$_{Ni}$-sfp$_{Bs}$) | |

Plasmid Construct Descriptions

Cloning strategies for all plasmids used in the current work are outlined in Table 4.

TABLE 4

Plasmid Construction

| Name | Description | Primers | Notes |
|---|---|---|---|
| pET-ter$_{Td}$-(bktB-pct) | T. denticola ter in MCS-1 (BamHI/NotI) and operon containing R. eutropha bktB and M. elsdenii pct in MCS-2 (BglII/XhaI) | | Tseng et al. Controlled biosynthesis of odd-chain fuels and chemicals via engineered modular metabolic pathways. PNAS 2012. bktB is cloned out of frame with MCS-2 RBS and built in start codon pct is preceeded by ggttagccttgcgctcgagaggagaattc RBS sequence New tar homologs cloned into existing pET-bktB-pct backbone |
| pET-ter$_{Vp}$-(bktB-pct) | V. porahaemolyticus ter in MCS-1 (NcoI/NotI) and operon containing R. eutropha bktB and M. elsdenii pct in MCS-2 (BglII/XhoI) | terVp_Up1: ATATAGGATCCGATGATCATCAAACCTAGAATTCG<br>terVp_Dn2: ATATAGCCGGCCGCTTAGATTTGAATGAAGTCTGTTTCTAC | |
| pET-ter$_{So}$-(bktB-pct) | S. oneidensis ter in MCS-1 (NcoI/NotI) and operon containing R. eutropha bktB and M. elsdenii pct in MCS-2 (BglII/XhoI) | terSo_Up1: ATATAGGATCCGATGATTATCAAACCCAAAATTCG<br>terSo_Dn2: ATATAGCCGGCCGCTTAAAGCTCAATCACTCCAACTC | |
| pET-ter$_{Eg}$-(bktB-pct) | E. gracilis ter in MCS-1 (BamHI/NotI) and operon containing R. eutropha bktB and M. elsdenii pct in MCS-2 (BglII/XhoI) | | E. gracilis ter subcloned from pET-ter$_{Eg}$-adhE from Tseng et al. into pET-bktB-pct backbone between BamHI/NotI sites. |
| pET-ter$_{Pa}$-(bktB-pct) | P. aeruginosa ter in MCS-1 (NcoI/NotI) and operon containing R. eutropha bktB and M. elsdenii pct in MCS-2 (BglII/XhoI) | terPa_Up2: ATATAGGATCCGATCATCAAACCGCGCGT<br>terPa_Dn2: ATATACTTAAGTTACTGGATCCAGGTTGGCGAT final GCC alanine codon removed to generate primer without secondary structure | |
| pET-ter$_{Pp}$-(bktB-pct) | P. putida ter in MCS-1 (NcoI/NotI) and operon containing R. eutropha bktB and M. elsdenii pct in MCS-2 (BglII/XhoI) | terPp_Up1: ATATAGGATCCCATGGCCATTCATTCATCCTA<br>terPp_Dn1: ATATACTTAAGTTACAGCTCGACGCAGTC | |
| pCDF-phaJ4b$_{Re}$-phaB | R. eutropha phaJ4b MCS-1 (NcoI/AflIII) and R. eutropha phaB (with NdeI site silently mutated out) in MCS-2 (NdeI/XhoI) | phaJ4bRe_Up1: ATATACCATGGCCATGAAGACCTACGAGAACATCG<br>phaJ4bRe_Dn1: ATATAGCCGGCCGCCTTATG phaJ4bRe was amplified from a pCDF-phaB-phaJ4b construct created by Hsien-Chung Tseng where phaJ4b had been cloned from gDNA into MCS-2 (BglII/XhoI). | |
| pCDF-phaJ4$_{Ps}$-phaB | P. syringae phaJ4 in MCS-1 (NcoI/NotI) and R. eutropha phaB (with NdeI site silently mutated out) in MCS-2 (NdeI/XhoI) | phaJ4Ps_Up1: ATATACCATGGGGATGCCTTTGTACCCGTCG<br>PhaJ4Ps_Dn1: ATATAGCCGGCCGCTTACGAAACACAACGTCAAAG | |
| pCDF-phaJ4$_{Pa}$-phaB | P. aeruginosa phaJ4 in MCS-1 (NcoI/NotI) and R. eutropha phaB (with NdeI site silently mutated out) in MCS-2 (NdeI/XhoI) | phaJ4Pa_Up1: ATATACCATGGGGATGCCATTCTACCCGTAG<br>phaJ4Pa_Dn1: ATATAGCCGGCCGCTCAGACGAAGCAGAGGCT | phaB has NdeI site mutated by quick-change PCR as used in Martin et al. It was subcloned from the pET-bktB-phaB construct using NdeI/XhoI restriction sites. |

TABLE 4-continued

Plasmid Construction

| Name | Description | Primers | Notes |
|---|---|---|---|
| pCDF-phaJ$_{Pa}$-phaB | P. aeruginosa phaJ1 in MCS-1 (BamHI/NotI) and R. eutropha phaB (with NdeI site silently mutated out) in MCS-2 (BglII/AvrII) | Tseng et al. Controlled biosynthesis of odd-chain fuels and chemicals via engineered modular metabolic pathways. PNAS 2012. | Both genes cloned with RBS's inserted after RE site and not inframe with plasmid RBS's. |
| pACVC-(alsS-ilvC-ilvD) | operon containing B. subtilis alsS and E. coli ilvC and ilvD in MCS-2 (BglII/AvrII) | alsS_up1: AAAAAAGATCTCATGACAAAAGCAACAAAAGA<br>alsS_dn1: GGTGATTCCTGCTAGAGAGCTTTCGTTTTCAT<br>ilvC_up1: CACGAGGAATCACC<br>ilvC_dn1: CATACTTTATTTACTCCCAGTTAACCCGCAACAG<br>ilvD_up1: CTGGGAGTAAATAAAGTATG<br>ilvD_dn1: AAAAAGACGTCTTAACCCCCAGTT | The RBS infront of ilvC contains the native 14 bp upstream of ilvC start codon cacgaggaatcacc and the RBS in front of ilvD contains the native 17 bp upstream of ilvD start codon ctgggagtaaataaagt |
| pET-(bktB-pct)-(phaJ4b-phaB) | operon containing R. eutropha bktB and M. elsdenii pct in MCS-1 (BamHI/NotI) and operon containing R. eutropha phaJ4b and phaB in MCS-2 (BglII/AvrII) | bktB_up4: AAAAAGGATCCGATGACGCGTGAAGTG<br>bktB_dn4: AAAAAGCGGCCGCTTATTTTTCAGTCCCA<br>pct_dn4: AAAAAGCGGCCGCTTATTTTTCAGTCCCA<br>phaJ4B_up4: taagtataagaaggagatacat<br>phaB_dn4: AAAAACCTAGGTCAGCCATGTGC | pct RBS sequence: ggttagcctgcgtccgagagggagaattc<br>phaB RBS sequence: taagtataagaaggagatacat operons amplified from pET-(bktB-pct)-(phaJ4b-phaB-ter) plasmid |
| pET-(bktB-ter)-(phaJ4b-phaB) | operon containing R. eutropha bktB and T. denticola ter in MCS-1 (BamHI/NotI) and operon containing R. eutropha phaJ4b and phaB in MCS-2 (BglII/AvrII) | bktB_terSOE_up1: AAAAAGGATCCGATGACGCGTGAAGTG<br>bktB_terSOE_dn1: CAATCATTATATCTCCTTCTTCAGATACGCTCGAAG<br>ter_up4: AAGAAGGAGATATAATGATTGTGAAACCGATG<br>ter_dn4: AAAAAGCGGCCGCTCAAATACGGTCAAGCGTTC | ter RBS sequence: aaaagaaggagatata bktB-ter operon cloned into pET-(phaJ4b-phaB) backbone |
| pCDF-(ilvD-ter)-(alsS-ilvC) | operon containing E. coli ilvD and T. denticola ter in MCS-1 (BamHI/NotI) and an operon containing B. subtilis alsS and E. coli ilvC in MCS-2 (BglII/AatII) | ilvD_ilvDSOE_up1: AAAAAGGATCCGATGCCTAAGTACCGTTCC<br>ilvD_dn4: CAATCATTATATCTCCTTCTTTAACCCCCAGTTC<br>ter_up4: AAGAAGGAGATATAATGATTGTGAAACCGATG<br>ter_dn4: AAAAAGCGGCCGCTCAAATACGGTCAAGCGTTC | The RBS infront of ilvC contains the native 14 bp upstream of ilvC start codon cacgaggaatcacc and the RBS in front of ter is the 14 bp sequence aagaaggagtata ilvD-ter operon cloned into pCDF-alsS-ilvC |
| pCDF-(ilvD-ter)-(ilvC-alsS) | operon containine M. elsdenii pct and E. coli ilvD in MCS-1 (BamHI/NotI) and an operon containing E. coli ilvC and B. subtilis alsS in MCS-2 (BglII/AatII) | ilvC_up5: TTTTTAGATCTATGGCTAACTACTTCAATAC<br>ilvC_dn5: CACCCTCACTCCTTATTAACCCGCAACAG<br>alsS_up5: TAAGGAGTGAGGGTGATGACAAAAGCAACAAA<br>alsS_dn5: TTTTTGACGTCCTAGAGAGCTTTCGTTTT | alsS RBS sequence: taaggagtgagggtg ilvC-alsS operon cloned into pCDF-(ilvD-ter) backbone |
| pCDF-(pct-ilvD)-(alsS-ilvC) | operon containing E. coli ilvD and pct and E. coli ilvD in MCS-1 (BamHI/NotI) and an operon containing B. subtilis alsS and E. coli ilvC in MCS-2 (BglII/AatII) | pct_ilvDSOE_up1: AAAAAGGATCCGATGAGAAAGTAGAAATCATTAC<br>pct_ilvDSOE_dn1: CATACTTTATTTACTCCCAGTTATTTTTCAGTCCCAT<br>ilvD_up3: CTGGGAGGAAATAAAGTATG<br>ilvD_dn3: AAAAAGCGGCCGCTTAACCCCCAGTT | ilvD RBS sequence: CTGGGAGGAAATAAAGT pct-ilvD operon cloned into pCDF-(alsS-ilvC) backbone |
| pCDF-(pct-ilvD)-(ilvC-alsS) | operon containine M. elsdenii pct and E. coli ilvD in MCS-1 (BamHI/NotI) and an operon containing E. coli ilvC and B. subtilis alsS in MCS-2 (BglII/AatII) | Same primers used to clone pct-ilvD operon as for pCDF-(alsS-ilvC)-(pct-ilvD) | pct-ilvD operon cloned into pCDF-(ilvC-alsS) backbone |
| pCDF-(ibuA-ilvD)-(alsS-ilvC) | operon containing R. palustris ibuA and E. coli ilvD in MCS-1 BglII/AatII) | ibuA_ilvDSOE_up1: AAAAAGGATCCGATGAGCAACACCCAT | ilvD RBS sequence: CTGGGAGGAAATAAAGT ibuA-ilvD operon cloned into pCDF-(alsS-ilvC) |

TABLE 4-continued

Plasmid Construction

| Name | Description | Primers | Notes |
|---|---|---|---|
| | (BamHI/NotI) and an operon containing B. subtilis alsS and E. coli ilvC in MCS-2 (BglII/AatII) | ibuA-ilvDSOE_dn1: CATACTTTATTCCTCCCAGTCAGCTGCAGAAGAA ilvD_up3: CTGGAGGAATAAAGTATG ilvD_dn3: AAAAAGCGGCCGCTTAACCCCCCAGTT | backbone |
| pCDF-(ibuA-ilvD)-(ilvC-alsS) | operon containing R. palustris ibuA and E. coli ilvD in MCS-1 (BamHI/NotI) and an operon containing E. coli ilvC and B. subtilis alsS in MCS-2 (BglII/AatII) | Same primers used to clone ibuA-ilvD operon as for pCDF-(alsS-ilvC)-(lbuA-ilvD) | ibuA-ilvD operon cloned into pCDF-(ilvC-alsS) backbone |
| pCOLA-puuC-kivD | L. lactis kivD in MCS-1 (BamHI/NotI) and E. coli puuC in MCS-2 (NdeI/XhoI) | kivD_up1: TTTTTTGGATCCGATGTATACAGTAGGAGATTACC kivD_dn1: TTTTTTGCGGCCGCTTATGATTTATTTTGTTCAG | kivD was cloned into the existing pCOLA-puuC, pCOLA-gabD, pCOLA-betB, and pCOLA-feaB plasmids |
| pCOLA-gabD-kivD | L. lactis kivD in MCS-1 (BamHI/NotI) and E. coli gabD in MCS-2 (NdeI/XhoI) | | |
| pCOLA-betB-kivD | L. lactis kivD in MCS-1 (BamHI/NotI) and E. coli betB in MCS-2 (NdeI/XhoI) | | |
| pCOLA-feaB-kivD | L. lactis kivD in MCS-1 (BamHI/NotI) and E. coli feaB in MCS-2 (NdeI/XhoI) | | |
| pACYC-(car-sfp)-ADH6 | operon containing N. lowensis car and B. subtilis sfp in MCS-1 (BamHI/AflII) and S. cerevisiae ADH6 in MCS-2 (NdeI/AatII) | sfp_up1: AAAAAAGCGGCCGCTAATAAAAGGAGATATACCATGAAAA TCTATGCATTTACAT sfp_dn1: AAATTTCTTAAGTTACACAGTTCTTCGTAGCT | car and sfp synthesized by GenScript for E. coli codon optimization. Car subcloned from puc57. sfp was amplified to add RBS upstream of start codon. car was subcloned first between BamHI/NotI and sfp with RBS was cloned after between NotI/AflII. ADH6 synthesized and codon optimized for E. coli by DNA 2.0. As subcloned the ADH6 open reading frame contains a C-terminal S-tag. |
| pACYC-(car-sfp) | operon containing N. lowensis car and B. subtilis sfp in MCS-1 (BamHI/AflII) | sfp_up1: AAAAAAGCGGCCGCTAATAAAAGGAGATATACCATGAAAA TCTATGCATTTACAT sfp_dn1: AAATTTCTTAAGTTACACAGTTCTTCGTAGCT | car and sfp synthesized by GenScript for E. coli codon optimization. Car subcloned from puc57, sfp was amplified to add RBS upstream of start codon, car was subcloned first between BamHI/NotI and sfp with RBS was cloned after between NotI/AflII. |
| pTKIP-neo-(tetR-P$_{tet}$alsS) | a DNA segment containing tetR and a tet inducible promoter upstream of B. subtilis alsS is cloned between landing pad sequence 1 and the FRT site upstream of the Kan resistance gene neo and its promoter in pTKIP-neo | Ptet_alsSSOE_up1: AAAAACCCGGAGATATTTGCTCATGAGCCC Ptet_alsSSOE_dn1: GCTAGCCCCAAAAAAACG alsS_PtetSOE_up1: GTTTTTTGGGCTAGCAATAAGGAGTGAGGGTGATG alsS_PtetSOE_dn1: AAAAAGCGGCCGCCTAGAGAGCTTTCGTTTTCATG pTKIP_up1: AAAAAGCGGCCCCGAAGTTCCTATTCTTCTAGAAAG pTKIP_dn1: AAAAACCCGGGCCTTCACCGTTTGGAC lac_op_LP_up1: | pHHD (Martin et al. 2013) was used a template for amplification of tetR with the P$_{tet}$ promoter. The tetR-Ptet fragment was linked to upstream of alsS with SOE PCR. The tetR-P$_{tet}$-alsS fragment was amplified to add XmaI and NotI sites at the 5' and 3' ends. The pTKIP-neo plasmid was amplified removing the cloning site and adding XmaI and NotI sites so that the tetR-P$_{tet}$-alsS fragment could be cloned into the vector. |

TABLE 4-continued

Plasmid Construction

| Name | Description | Primers | Notes |
|---|---|---|---|
| | | CTCGTATGTTGTGTGGAATTGTGAGCGGATAACAATTTCAC ACAGGAAACAGCTTACGGCCCCAAGGTCC lac_op_LP_dn1: GCTTATCCCGGTCGTTTATTTCGCGAATAACCCGACAAGGA ACGCCAGCCTTGCTTCAGGGATGAGG | The lac_op_LP primers were used to amplify tetA and the landing pad sites with the lac operon homology sequence underlined |

In Table 4: terVp_Up1: SEQ ID NO: 5; terVp_Dn2: SEQ ID NO: 6; terSo_Up1: SEQ ID NO: 7; terSo_Dn2: SEQ ID NO: 8; terPa_Up2: SEQ ID NO: 9; terPa_Dn2: SEQ ID NO: 10; terPp_Up1: SEQ ID NO: 11; terPp_Dn1: SEQ ID NO: 12; phaJ4bRe_Up1: SEQ ID NO: 13; phaJ4bRe_Dn1: SEQ ID NO: 14; phaJ4Ps_Up1: SEQ ID NO: 15; phaJ4Ps_Dn1: SEQ ID NO: 16; phaJ4Pa_Up1: SEQ ID NO: 17; phaJ4 Pa_Dn1: SEQ ID NO: 18; alsS_up1: SEQ ID NO: 19; alsS_dn1: SEQ ID NO: 20; ilvC_up1: SEQ ID NO: 21; ilvC_dn1: SEQ ID NO: 22; ilvD_up1: SEQ ID NO:23; ilvD_dn1: SEQ ID NO: 24; bktB_up4: SEQ ID NO: 25; pct_dn4: SEQ ID NO: 26; phaJ4b_up4: SEQ ID NO: 27; phaB_dn4: SEQ ID NO: 28; bktB_terSOE_up1: SEQ ID NO: 29; bktB_terSOE_dn1: SEQ ID NO: 30; ter_up4: SEQ ID NO: 31; ter_dn4: SEQ ID NO: 32; ilvD_up4: SEQ ID NO: 33; ilvD_dn4: SEQ ID NO: 34; ter_up4: SEQ ID NO: 35; ter_dn4: SEQ ID NO: 36; ilvC_up5: SEQ ID NO: 37; ilvC_dn5: SEQ ID NO: 38; alsS_up5: SEQ ID NO: 39; alsS_dn5: SEQ ID NO: 40; pct_ilvDSOE_up1: SEQ ID NO: 41; pct_ilvDSOE_dn1: SEQ ID NO: 42; ilvD_up3: SEQ ID NO: 43; ilvD_dn3: SEQ ID NO: 44; ibuA_ilvDSOE_up1: SEQ ID NO: 45; ibuA_ilvDSOE_dn1: SEQ ID NO: 46; ilvD_up3: SEQ ID NO: 47; ilvD_dn3: SEQ ID NO: 48; kivD_up1: SEQ ID NO: 49; kivD_dn1: SEQ ID NO: 50; sfp_up1: SEQ ID NO: 51; sfp_dn1: SEQ ID NO: 52; sfp_up1: SEQ ID NO: 53; sfp_dn1: SEQ ID NO: 54; Ptet_alsSSOE_up1: SEQ ID NO: 55; Ptet_alsSSOE_dn1: SEQ ID NO: 56; alsS_PtetSOE_up1: SEQ ID NO: 57; alsS_PtetSOE_dn1: SEQ ID NO: 58; TKIP_up1: SEQ ID NO:59; pTKIP_dn1: SEQ ID NO: 60; lac_op_LP_up1: SEQ ID NO: 61; lac_op_LP_dn1: SEQ ID NO: 62; pct RBS sequence: SEQ ID NO: 63; phaB RBS sequence: SEQ ID NO: 64; ter RBS sequence for plasmid pET-(bktB-ter)-(phaJ4b-phaB): SEQ ID NO: 65; ter RBS sequence for plasmid pCDF-(ilvD-ter)-(alsS-ilvC): SEQ ID NO: 66; alsS RBS sequence: SEQ ID NO: 67; ilvC RBS sequence: SEQ ID NO: 21; ilvD RBS sequence: SEQ ID NO: 68.

TABLE 5

Additional strains used for module and full pathway evaluation.
Host strains and plasmids are listed. Strain names indicate the modules present in the strain, i.e. M1F2P34 includes "M" for modules, "1F" for Module 1 with feaBEc, "2P" for Module 2 with pctMe, "3" for Module 3 and "4" for Module 4. Strains with "( )" contain abbreviations for operon structure indicating the order of alsSBs and ilvCEc, i.e. M1F(IA)2I34 indicates that it contains an ilvCEc-alsSBs operon. Key strains indicated in bold.

| Plasmid 1 | Plasmid 2 | Plasmid 3 | Strain name |
| --- | --- | --- | --- |
| pACYC-(car$_{Ni}$-sfp$_{Bs}$)-ADH6$_{Sc}$ | — | — | M4 |
| pACYC-(car$_{Ni}$-sfp$_{Bs}$)-ADH6$_{Sc}$ | pET-ter$_{Td}$-(bktB$_{Cn}$-pct$_{Me}$) | pCDF-phaJ4b$_{Cn}$-phaB$_{Cn}$ | M2P34 |
| pET-(bktB$_{Cn}$-pct$_{Me}$)-(phaJ4b$_{Cn}$-phaB$_{Cn}$) | pCDF-(ilvD$_{Ec}$-ter$_{Td}$)-(alsS$_{Bs}$-ilvC$_{Ec}$) | pCOLA-kivD$_{Ll}$-feaB$_{Ec}$ | M1F2P3 |
|  |  | pCOLA-kivD$_{Ll}$-puuC$_{Ec}$ | M1P2P3 |

| Plasmid 1 | Plasmid 2 | Plasmid 3 | Plasmid 4 | Strain name |
| --- | --- | --- | --- | --- |
| pET-(bktB$_{Cn}$-pct$_{Me}$)-(phaJ4b$_{Cn}$-phaB$_{Cn}$) | pCDF-(ilvD$_{Ec}$-ter$_{Td}$)-(alsS$_{Bs}$-ilvC$_{Ec}$) | pACYC-(car$_{Ni}$-sfp$_{Bs}$)-ADH6$_{Sc}$ | pCOLA-kivD$_{Ll}$-feaB$_{Ec}$ | M1F2P34 |
|  |  |  | pCOLA-kivD$_{Ll}$-puuC$_{Ec}$ | M1P2P34 |
| pCDF-pct$_{Me}$ | pET-(bktB$_{Cn}$-ter$_{Td}$)-(phaJ4b$_{Cn}$-phaB$_{Cn}$) | — | — | M2P3a |
|  | pET-(bktB$_{Cn}$-ter$_{Td}$)-(phaB$_{Cn}$-phaJ4b$_{Cn}$) | — | — | M2P3b |
| pET-(bktB$_{Cn}$-ter$_{Td}$)-(phaB$_{Cn}$-phaJ4b$_{Cn}$) | pACYC-(car$_{Ni}$-sfp$_{Bs}$)-ADH6$_{Sc}$ | pCOLA-kivD$_{Ll}$- feaB$_{Ec}$ | pCDF-(ibuA$_{Rp}$-ilvD$_{Ec}$)-(alsS$_{Bs}$,ilvC$_{Ec}$) | M1F(AI)2I34 |
|  |  |  | pCDF-(ibuA$_{Rp}$-ilvD$_{Ec}$)-(ilvC$_{Ec}$-alsS$_{Bs}$) | M1F(IA)2I34 |
|  | pCDF-(ibuA$_{Rp}$-ilvD$_{Ec}$)-(ilvC$_{Ec}$-alsS$_{Bs}$) | pCOLA-kivD$_{Ll}$-feaB$_{Ec}$ | pACYC-(car$_{Ni}$-sfp$_{Bs}$) | M1F(IA)2I34a |
|  |  | pCOLA-kivD$_{Ll}$-Fjoh_2967$_{Fj}$ | pACYC-(car$_{Ni}$-sfp$_{Bs}$)-ADH6$_{Sc}$ | M1Fj(IA)2I34 |
|  |  |  | pACYC-(car$_{Ni}$-sfp$_{Bs}$)-lsadh$_{Ls}$ | M1Fj(IA)2I34L |

TABLE 6

Enzymes used in all pathway variants. Enzymes are tabulated by module with their organism of origin, previously assigned activities, and function in the 4-methyl-1-pentanol pathway. Enzymes in bold were used in the two final full pathway strains M1Fj(IA)2I34 and M1Fj(IA)2I34L.

| Module | Enzyme | Organism | Assigned Activity | Observed Pathway Function |
| --- | --- | --- | --- | --- |
| 1 | AlsS$_{Bs}$ | B. subtilis | acetolactate synthase | same as assigned function: synthesis of acetolactate from two pyruvate |
|  | IlvC$_{Ec}$ | E. coli | acetohydroxy acid isomeroreductase | same as assigned function: synthesis of 2,3-dihydroxy-3-methylbutanoate from acetolactate |

TABLE 6-continued

Enzymes used in all pathway variants. Enzymes are tabulated by module with their organism of origin, previously assigned activities, and function in the 4-methyl-1-pentanol pathway. Enzymes in bold were used in the two final full pathway strains M1Fj(IA)2I34 and M1Fj(IA)2I34L.

| Module | Enzyme | Organism | Assigned Activity | Observed Pathway Function |
|---|---|---|---|---|
| | IlvD$_{Ec}$ | E. coli | dihydroxy acid dehydratase | same as assigned function: synthesis of α-ketoisovalerate (αKIV) from 2,3-dihydroxy-3-methylbutanoate |
| | KivD$_{Ll}$ | L. lactis | α-ketoisovalerate decarboxylase | same as assigned function: synthesis of isobutyraldehyde from α-ketoisovalerate (αKIV) |
| | FeaB$_{Ec}$ | E. coli | phenylacetaldehyde dehydrogenase | synthesis of isobutyrate from isobutyraldehyde |
| | PuuC$_{Ec}$ | E. coli | γ-glutamyl-γ-amino-butyraldehyde dehydrogenase | synthesis of isobutyrate from isobutyraldehyde |
| | Fjoh2967$_{Fj}$ | F. johnsonaie | aldehyde dehydrogenase | synthesis of isobutyrate from isobutyraldehyde |
| 2 | Pct$_{Me}$ | M. elsdenii | propionyl-CoA transferase | synthesis of isobutyryl-CoA from isobutyrate |
| | IbuA$_{Rp}$ | R. palustris | isobutyryl-CoA ligase | synthesis of isobutryl-CoA from isobutyrate |
| 4 | Car$_{Ni}$ | N. iowensis | carboxylic acid reductase | synthesis of 4-methyl-valeraldehyde from 4-methyl-valerate (synthesis of butyraldehyde from butyrate) |
| | Sfp$_{Bs}$ | B. subtilis | 4'-phosphopantetheinyl transferase (surfactin synthetase activator) | activation of Car$_{Ni}$ |
| | Adh6p$_{Sc}$ | S. cerevisiae | alcohol dehydrogenase | synthesis of 4-methyl-pentanol from 4-methyl-valeraldehyde (synthesis of butanol and isobutanol from butyraldehyde and isobutyraldehyde) |
| | Lsadh$_{Ls}$ | L. sp. Strain S749 | alcohol dehydrogenase | synthesis of 4-methyl-pentanol from 4-methyl-valeraldehyde |

REFERENCES

Akhtar, M. K., Turner, N. J., & Jones, P. R. (2013) Proceedings of the National Academy of Sciences 110, 87-92.

Annual Energy Review 2011. Washington: Government Printing Office, 2012.

Atsumi, S., Cann, A. F., Connor, M. R., Shen. C. R., Smith, K. M., Brynildsen, M. P., Chou, K. J. Y., Hanai. T., & Liao, J. C. (2008) Metabolic Engineering 10, 305-311.

Atsumi, S., Hanai, T., & Liao. J. C. (2008) Nature 451, 86-89.

Atsumi, S. & Liao, J. C. (2008) Current Opinion in Biotechnology 19, 414-419.

Atsumi, S., Li, Z., & Liao, J. C. (2009) Applied and Environmental Microbiology 75, 6306-6311.

Atsumi, S., Wu, T.-Y., Eckl, E.-M., Hawkins, S., Buelter. T., & Liao, J. (2010) Applied Microbiology and Biotechnology 85, 651-657.

Bachmann B O. (2010) Nat Chem Biol 6, 390-393.

Bond-Watts, B. B., Bellerose, R. J., & Chang. M. C. Y. (2011) Nat Chem Biol 7, 222-227.

Chan, D. I. & Vogel, H. J. (2010) Biochemical Journal 430, 1-19.

Chao J, Rossini F D. (1965) Journal of Chemical and Engineering Data 10, 374.

Choi J-i, Lee S Y, Han K. (1998) Applied and Environmental Microbiology. 64, 4897 4903 (1998).

Contis, E. T. Foodflavors: formation, analysis, and packaging influences. in 9th International Flavor Conference. (1997) George Charalambous Memorial Symposium, Limnos, Greece: Elsevier Cracan V, Padovani D, Banerjee R. (2010). Journal of Biological Chemistry 285, 655-666.

Crosby, H. A., Pelletier, D. A., Hurst. G. B., & Escalante-Semerena, J. C. (2012) Journal of Biological Chemistry 287, 15590-15601.

De Smidt, O., Du Preez, J. C., & Albertyn, J. (2008) FEMS Yeast Research 8, 967-978.

Dehesh, K., Jones, A., Knutzon, D. S., & Voelker, T. A. (1996) The Plant Journal 9, 167-172.

Dekishima, Y., Lan, E. I., Shen, C. R., Cho, K. M., & Liao, J. C. (2013) Journal of the American Chemical Society 133, 11399-11401.

Dellomonaco, C., Clomburg, J. M., Miller, E. N., & Gonzalez. R. (2011) Nature 476, 355-359.

Dennis, D., McCoy, M., Stangl, A., Valentin, H. E., & Wu, Z. (1998) Journal of Biotechnology 64, 177-186.

Dickson R C. (2008) Journal of Lipid Research 49, 909-921.

Dugar, D. & Stephanopoulos, G. (2011) Nat Biotech 29, 1074-1078.

Ferrandez, A., Prieto, M. A., Garcia, J. L., & Diaz, E. (1997) FEBS Letters 406, 23-27.

Fontaine, L., Meynial-Salles, I., Girbal, L., Yang, X., Croux, C., & Soucaille, P. (2002) Journal of Bacteriology 184, 821-830.

Goenaga J M, Gayol A, Concha R G, Iglesias M, Resa J M. (2007) Chemical Monthly 138, 403-436.

Hales J L, Ellender J H. (1976) The Journal of Chemical Thermodynamics 8, 1177-1184.

Hansen E H, et al. (2009) Applied and Environmental Microbiology 75, 2765-2774.

Handke, P., Lynch, S. A., & Gill, R. T. (2011) Metabolic Engineering 13, 28-37.

Hoffmeister, M., Piotrowski, M., Nowitzki, U., & Martin, W. (2005) Journal of Biological Chemistry 280, 4329-4338.

Hopwood D A, Sherman D H. (1990) Annual Review of Genetics 24, 37-62.

Howard T P, et al. (2013) Proceedings of the National Academy of Sciences 110, 7636 7641.

Huang, W.-D. & Percival Zhang, Y. H. (2011) Energy & Environmental Science 4, 784-792.

Hussein N M, Asfour A-F A. (2009) Journal of Chemical & Engineering Data 54, 2948 2952.

Inoue K, Makino Y, Dairi T, Itoh N. (2006) Bioscience, Biotechnology, and Biochemistry 70, 418-426.

Inoue K. Makino Y. Itoh N. (2005) Applied and Environmental Microbiology 71, 3633 3641.

Jo, J.-E., Mohan Raj, S., Rathnasingh, C., Selvakumar, E., Jung, W.-C., & Park, S. (2008) Applied Microbiology and Biotechnology 81, 51-60.

JÖRnvall, H., Persson, B., & Jeffery, J. (1987) European Journal of Biochemistry 167, 195-201.

Kawashima. Y., Cheng. W., Mifune, J., Orita, I., Nakamura, S., & Fukui, T. (2012) Applied and Environmental Microbiology 78, 493-502.

Kim, Y., Ingram, L. O., & Shanmugam, K. T. (2008) Journal of Bacteriology 190, 3851 3858.

Kurihara, S., Oda, S., Kato, K., Kim, H. G., Koyanagi, T., Kumagai, H., & Suzuki, H. (2005) Journal of Biological Chemistry 280, 4602-4608.

Larroy, C., FernÃÃndez, M. R., GonzÃÃlez, E., ParÃ©s, X., & Biosca, J. A. (2002) Biochem. J. 361, 163-172.

Lee, S. K., Chou, H., Ham, T. S., Lee, T. S., & Keasling, J. D. (2008) Current Opinion in Biotechnology 19, 556-563.

Lennen, R. M. & Pfleger, B. F. (2013) Current Opinion in Biotechnology.

Li, T. & Rosazza, J. P. (1997) Journal of Bacteriology 179, 3482-3487.

Lichtenthaler H K, Rohmer M, Schwender J. (1997) Physiologia Plantarum 101, 643-652.

Lim H N, Lee Y, Hussein R. (2011) Proceedings of the National Academy of Sciences 108, 10626-10631.

Machado I M P, Atsumi S. (2012) Journal of Biotechnology 162, 50-56.

Magnuson, K., Jackowski, S., Rock, C. O., & Cronan, J. E. (1993) Microbiological Reviews 57, 522-542

Marcheschi R J, et al. (2012) ACS Chemical Biology 7, 689-697.

Martin, C. H., Dhamankar, H., Tseng, H.-C., Sheppard, M. J., Reisch, C. R., & Prather, K. L. J. (2013) Nat Commun 4, 1414.

McMahon M D, Prather K L J. (2014) Applied and Environmental Microbiology 80, 1042 1050.

Moon T S, Yoon S-H, Lanza A M, Roy-Mayhew J D, Prather K L J. (2009) Applied and Environmental Microbiology 75, 589-595. Nielsen, D. R., Leonard, E., Yoon, S.-H., Tseng. H.-C., Yuan, C., & Prather, K. L. J. (2009) Metabolic Engineering 11, 262-273.

Niu W, Molefe M N, Frost J W. (2003) Journal of the American Chemical Society 125, 12998-12999.

Pfeifer B A, Admiraal S J, Gramajo H, Cane D E, Khosla C. (2001) Science 291, 1790 1792.

Prather K L J, Martin C H. (2008) Current Opinion in Biotechnology 19, 468-474.

Ragauskas A J, et al. (2006) Science 311, 484-489.

Rodríguez-Zavala, J. S., Allali-Hassani, A., & Weiner, H. (2006) Protein Science 15, 1387-1396.

Shen, C. R., Lan, E. I., Dekishima, Y., Baez, A., Cho, K. M., & Liao, J. C. (2011) Applied and Environmental Microbiology 77, 2905-2915.

Steen E, et al. (2008) Microbial Cell Factories 7, 36.

Taguchi, S., Yamada, M., Matsumoto, K. i., Tajima, K., Satoh, Y., Munekata, M., Ohno, K., Kohda, K., Shimamura, T., Kambe, H., et al. (2008) Proceedings of the National Academy of Sciences 105, 17323-17327.

Torella, J. P., Ford, T. J., Kim, S. N., Chen, A. M., Way, J. C., & Silver, P. A. (2013) Proceedings of the National Academy of Sciences 110, 11290-11295.

Tseng, H.-C. & Prather, K. L. J. (2012) Proceedings of the National Academy of Sciences 109, 17925-17930.

Tseng H-C, Martin C H, Nielsen D R, Prather K L J. (2009) Applied and Environmental Microbiology 75, 3137-3145.

Tseng H-C, Harwell C, Martin C. Prather K. (2010) Microbial Cell Factories 9, 96.

Tucci S, Martin W. (2007) FEBS Letters 581, 1561-1566.

Venkitasubramanian, P., Daniels, L., & Rosazza, J. P. N. (2007) Journal of Biological Chemistry 282, 478-485.

Venkitasubramanian, P., Daniels, L., Das, S., Lamm, A. S., & Rosazza, J. P. N. (2008) Enzyme and Microbial Technology 42, 130-137.

Voelker, T. A. & Davies, H. M. (1994) Journal of Bacteriology 176, 7320-7327.

Wallner, T., Ickes, A., & Lawyer, K. (2012) in Proceedings of the FISITA 2012 World Automotive Congress (Springer Berlin Heidelberg), pp. 15-26.

Wang J, Hou T, Xu X. (2009) Journal of Chemical Information and Modeling 49, 571 581.

Wenzel S C, Müller R. (2005) Current Opinion in Biotechnology 16, 594-606.

White, S. W., Zheng, J., Zhang, Y. M., & Rock, C. O. (2005) Annual Review of Biochemistry 74, 791-831.

Withers, S. T., Gottlieb, S. S., Lieu, B., Newman, J. D., & Keasling, J. D. (2007) Applied and Environmental Microbiology 73, 6277-6283.

Yamanaka Y, Kazuoka T, Yoshida M, Yamanaka K, Oikawa T, Soda K. (2002) Biochemical and Biophysical Research Communications 298, 632-637.

Youngquist, J. T., Rose, J., & Pfleger, B. (2013) Applied Microbiology and Biotechnology 97, 5149-5159.

Zhang, K., Sawaya, M. R., Eisenberg, D. S., & Liao, J. C. (2008) Proceedings of the National Academy of Sciences. 105(52):20653-20658

Zhang, X., Li, M., Agrawal, A., & San, K.-Y. (2011) Metabolic Engineering 13, 713 722.

Zhang, K., Woodruff, A. P., Xiong, M., Zhou, J., & Dhande, Y. K. (2011) ChemSusChem 4, 1068-1070.

Zor T, Selinger Z. (1996) Analytical Biochemistry 236, 302-308.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety, particularly for the disclosure referenced herein.

The invention claimed is:

1. A cell that recombinantly expresses:
   (a) a *Cupriavidus* bktB gene;
   (b) a *Cupriavidus* phaB gene;
   (c) a *Cupriavidus* phaJ4b gene;
   (d) a *Treponema* ter gene;
   (e) a *Nocardia* car gene;
   wherein the cell produces a branched medium-chain alcohol, and
   wherein the cell is a bacterial cell or a yeast cell.

2. The cell of claim 1, wherein
   the *Cupriavidus* bktB gene is a *Cupriavidus necator* bktB gene;
   the *Cupriavidus* phaB gene is a *Cupriavidus necator* phaB gene;
   the *Cupriavidus* phaJ4b gene is a *Cupriavidus necator* phJ4b gene;
   the *Treponema* ter gene is a *Treponema denticola* ter gene; and/or
   the *Nocardia* car gene is a *Nocardia iowensis* car gene.

3. The cell of claim 1, wherein the cell further recombinantly expresses one or both of
   a gene encoding an alcohol dehydrogenase, optionally an ADH6 gene or a lsadh gene, and
   a gene encoding an aldoketo reductase, optionally a yeaE gene,
   wherein the ADH6 gene is optionally a *Saccharomyces* ADH6 gene, the lsadh gene is optionally a *Leifsonia* lsadh gene, and/or the yeaE gene is optionally an *Escherichia* yeaE gene.

4. The cell of claim 1, wherein the cell further recombinantly expresses one or more of
   a gene encoding an acetolactate synthase, optionally an alsS gene, and optionally a *Bacillus* alsS gene;
   a gene encoding an acetohydroxy acid isomeroreductase, optionally an ilvC gene, and optionally an *Escherichia* ilvC gene;
   a gene encoding a dihydroxy acid dehydratase, optionally an ilvD gene, and optionally an *Escherichia* ilvD gene;
   a gene encoding a decarboxylase, optionally a kivD gene, and optionally a *Lactococcus* kivD gene; and
   one or both of a gene encoding a phenylacetaldehyde dehydrogenase, optionally a feaB gene, and optionally an *Escherichia* feaB gene; and
   a gene encoding an aldehyde dehydrogenase, optionally a puuC gene or a fjoh2967 gene, wherein the puuC gene is optionally an *Escherichia* puuC gene and the foh2967 gene is optionally a *Flavobacterium* foh2967 gene.

5. The cell of claim 1, wherein
   (i) the cell further recombinantly expresses one or both of
      a gene encoding a propionyl-CoA transferase, optionally a pct gene, and optionally a *Megasphaera* pct gene, and
      a gene encoding an isobutyryl-CoA ligase, optionally an ibuA gene, and optionally a *Rhodopseudomonas* ibuA gene; and/or
   (ii) the cell further expresses a gene encoding a thioesterase.

6. The cell of claim 1, wherein the cell is an *Escherichia coli* or *Bacillus* sp. cell.

7. The cell of claim 5, wherein the gene encoding a thioesterase is a tesB gene or a ydiI gene.

8. The cell of claim 5, wherein one or more of bktB, phaB, phaJ4b, ter, car, ADH6, yeaE, alsS, ilvC, ilvD, kivD, feaB, puuC, pct, ibuA, tesB, lsadh, fjoh2967, and ydiI is expressed from a plasmid; and/or
   wherein at least one copy of one or more of bktB, phaB, phaJ4b, ter, car, ADH6, yeaE, alsS, ilvC, ilvD, kivD, feaB, puuC, pct, ibuA, tesB, lsadh, fjoh2967, and ydiI is integrated into the genome of the cell; and/or
   wherein expression of one or more of bktB, phaB, phaJ4b, ter, car, ADH6, yeaE, alsS, ilvC, ilvD, kivD, feaB, puuC, pct, ibuA, tesB, lsadh, fjoh2967, and ydiI is regulated by one or more inducible promoter(s).

9. The cell of claim 1, wherein the branched medium-chain alcohol is 4-methyl-1-pentanol.

10. A cell culture or supernatant collected from culturing one or more cell(s) of claim 1, optionally wherein the cell culture or supernatant contains at least 10 mg/L 4-methyl-1-pentanol.

11. A method comprising culturing the cell of claim 1 in cell culture medium, optionally wherein glucose and/or isobutyrate are added to the cell culture medium.

12. A method for producing 4-methyl-1-pentanol comprising culturing one or more cells of claim 1 to produce a cell culture or supernatant containing 4-methyl-1-pentanol, optionally wherein the 4-methyl-1-pentanol is further purified from the cell culture or supernatant.

13. A method for producing a branched medium-chain alcohol comprising recombinantly expressing in a cell:
   (a) a *Cupriavidus* bktB gene;
   (b) a *Cupriavidus* phaB gene;
   (c) a *Cupriavidus* phaJ4b gene;
   (d) a *Treponema* ter gene; and
   (e) a *Nocardia* car gene,
   wherein the cell produces the branched medium-chain alcohol, and
   wherein the cell is a bacterial cell or a yeast cell.

14. The method of claim 13, wherein
   the *Cupriavidus* bktB gene is a *Cupriavidus necator* bktB gene;
   the *Cupriavidus* phaB gene is a *Cupriavidus necator* phaB gene;
   the *Cupriavidus* phaJ4b gene is a *Cupriavidus necator* phj4b gene;
   the *Treponema* ter gene is a *Treponema denticola* ter gene; and/or
   the *Nocardia* car gene is a *Nocardia iowensis* car gene.

15. The method of claim 13, wherein the cell further recombinantly expresses one or both of
   a gene encoding an alcohol dehydrogenase, optionally an ADH6 gene or an lsadh gene, and
   a gene encoding an aldo-keto reductase, optionally a yeaE gene,
   wherein the ADH6 gene is optionally a *Saccharomyces* ADH6 gene, the lsadh gene is optionally a *Leifsonia* lsadh gene, and the yeaE gene is optionally an *Escherichia* yeaE gene.

16. The method of claim 13, wherein the cell further recombinantly expresses one or more of
   a gene encoding an acetolactate synthase, optionally an alsS gene, and optionally a *Bacillus* alsS gene;
   a gene encoding an acetohydroxy acid isomeroreductase, optionally an ilvC gene, and optionally an *Escherichia* ilvC gene;
   a gene encoding a dihydroxy acid dehydratase, optionally an ilvD gene, and optionally an *Escherichia* ilvD gene;
   a gene encoding a decarboxylase, optionally a kivD gene; and optionally a *Lactococcus* kivD gene; and
   one or both of a gene encoding a phenylacetaldehyde dehydrogenase, optionally afeaB gene, and optionally an *Escherichia* feaB gene; and a gene encoding an aldehyde dehydrogenase, optionally a puuC gene or a fjoh2967 gene, wherein the puuC gene is optionally an *Escherichia* gene and the foh2967 gene is optionally a *Flavobacterium* foh2967 gene.

17. The method of claim 13, wherein
   (i) the cell further recombinantly expresses one or both of
      a gene encoding a propionyl-CoA transferase, optionally a pct gene, and optionally a *Megasphaera* pct gene; and
      a gene encoding an isobutyryl-CoA ligase, optionally a ibuA gene, and optionally a *Rhodopseudomonas* ibuA gene; and/or
   (ii) the cell further expresses a gene encoding a thioesterase.

18. The method of claim 13, wherein the cell is an *Escherichia coli* or *Bacillus* sp. cell.

19. The method of claim 17, wherein the gene encoding a thioesterase is a tesB gene or a ydiI gene.

20. The method of claim 13, wherein
   one or more of bktB, phaB, phaJ4b, ter, car, ADH6, yeaE, alsS, ilvC, ilvD, kivD, feaB, puuC, pct, ibuA, tesB, lsadh, fjoh2967, and ydiI is expressed from a plasmid; and/or
   wherein at least one copy of one or more of bktB, phaB, phaJ4b, ter, car, ADH6, yeaE, alsS, ilvC, ilvD, kivD, feaB, puuC, pct, ibuA, tesB, lsadh, fjoh2967, and ydiI is integrated into the genome of the cell, and/or
   wherein expression of one or more of bktB, phaB, phaJ4b, ter, car, ADH6, yeaE, alsS, ilvC, ilvD, kivD, feaB, puuC, pct, ibuA, tesB, lsadh, fjoh2967, and ydiI is regulated by one or more inducible promoter(s).

21. The method of claim 13, wherein the branched medium-chain alcohol-is 4-methyl-1-pentanol.

* * * * *

UNITED STATES PATENT AND TRADEMARK OFFICE
CERTIFICATE OF CORRECTION

PATENT NO. : 10,100,335 B2
APPLICATION NO. : 14/530540
DATED : October 16, 2018
INVENTOR(S) : Prather et al.

Page 1 of 1

It is certified that error appears in the above-identified patent and that said Letters Patent is hereby corrected as shown below:

In the Claims

At Column 89, Claim 1, Line 6, "(d) a *Treponema* ter gene;" should be --(d) a *Treponema* ter gene; and--

At Column 89, Claim 2, Line 17, "phJ4b" should be --phaJ4b--

At Column 90, Claim 14, Line 40, "phj4b" should be --phaJ4b--

At Column 90, Claim 16, Line 66, "afeaB" should be --a feaB--

Signed and Sealed this
Seventeenth Day of September, 2019

Andrei Iancu
*Director of the United States Patent and Trademark Office*